(12) United States Patent
Smith

(10) Patent No.: US 6,191,124 B1
(45) Date of Patent: Feb. 20, 2001

(54) METHANOL DERIVATIVES FOR TREATMENT OF RETROVIRAL INFECTIONS ESPECIALLY HIV INFECTIONS

(75) Inventor: Herman W. Smith, Kalamazoo, MI (US)

(73) Assignee: Pharmacia & Upjohn Company, Kalamazoo, MI (US)

( * ) Notice: Under 35 U.S.C. 154(b), the term of this patent shall be extended for 0 days.

(21) Appl. No.: 09/180,809

(22) PCT Filed: Apr. 20, 1995

(86) PCT No.: PCT/US95/04444

§ 371 Date: Apr. 7, 1997

§ 102(e) Date: Apr. 7, 1997

(87) PCT Pub. No.: WO95/29922

PCT Pub. Date: Nov. 9, 1995

Related U.S. Application Data

(63) Continuation-in-part of application No. 08/236,417, filed on Apr. 29, 1994, now abandoned.

(51) Int. Cl.[7] .................. C07D 513/04; A61K 31/429

(52) U.S. Cl. .................. 514/151; 514/153; 548/151; 548/154

(58) Field of Search .................. 548/151, 154, 548/366, 368; 514/366, 368

(56) References Cited

FOREIGN PATENT DOCUMENTS 269 919    1/1994   (DE) .

OTHER PUBLICATIONS

Moog, Christiane, et al., Bicyclic imidazo derivatives, a new class of highly selective inhibitors for the human immunodeficiency virus type 1; Antiviral Research 24 (1994) 275–288.

Science, vol. 265, 1028–1029, Aug. 19, 1994.

*Primary Examiner*—Robert Gerstl
(74) *Attorney, Agent, or Firm*—James D. Darnley

(57) ABSTRACT

The present invention relates to compounds of formula (I) which are imidazo[2,1-b]benzothiazole-3-methanol and imidazo[2,1-b]thiazole-5-methanol derivatives useful for inhibiting a retrovirus in a mammalian cell infected with said retrovirus, wherein $R_1$ is —H or —$CH_3$; wherein $R_2$ is —H or —$CH_3$; or wherein $R_1$ and $R_2$ taken together are (a) formula (II), or (b) formula (III).

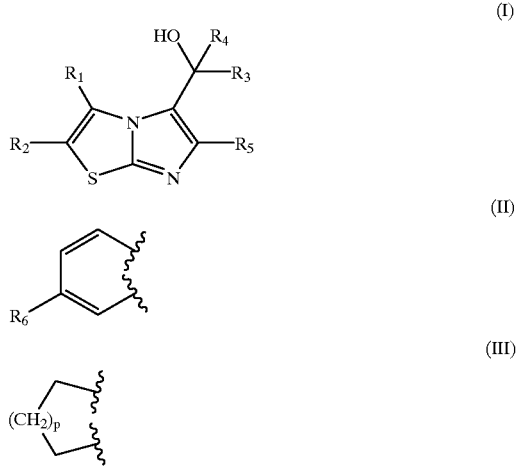

15 Claims, No Drawings

METHANOL DERIVATIVES FOR TREATMENT OF RETROVIRAL INFECTIONS ESPECIALLY HIV INFECTIONS

This application is a 371 of PCT/US95/04444 filed Apr. 20, 1995, and a C-I-P of Ser. No. 08/236,417 filed Apr. 29, 1994 now abandoned.

FIELD OF THE INVENTION

The present invention relates to compounds useful for inhibiting a retrovirus in a human cell infected with said retrovirus. More particularly, the present invention provides imidazo[2,1-b]thiazole derivatives as HIV-proteinase inhibitors.

BACKGROUND OF THE INVENTION

During the past decade, acquired immunodeficiency syndrome (AIDS) has progressed from having the status of a medical curiosity afflicting only a small number of individuals to a problem of major proportions, both medically and economically. John Saunders and Richard Storer, "New Developments in RT Inhibitors," DN&P 5(3), April 1992, pages 153–169. WHO figures reveal that more than 360,000 cases of AIDS have been reported worldwide, including nearly 175,000 cases in the U.S.A. Of these, approximately 100,000 worldwide (50,000 in the U.S.A.) were reported in the preceding 12-month period and WHO estimated over one million new infections during the first half of 1992. In the U.S.A., the number of seropositive individuals is thought to be approximately two million, and estimates suggest that 5–10 million people worldwide may be seropositive. Saunders and Storer, page 153.

Since the first description of the malady in the early part of this decade, acquired immunodeficiency disease syndrome (AIDS) and its devastating consequences have been subjects of continuous and intense coverage in both the lay and scientific press. Indeed, an edition of Scientific American was entirely devoted to AIDS (Scientific American 289, #4 (1988)), and the literature on the disease and the virus is already so vast as to defy thorough citation.

On Mar. 20, 1987, the FDA approved the use of the compound, zidovudine (AZT), to treat AIDS patients with a recent initial episode of pneumocystis carinii pneumonia, AIDS patients with conditions other than pneumocystis carinii pneumonia or patients infected with the virus with an absolute CD4 lymphocyte count of less than 200/mm$^3$ in the peripheral blood. AZT is a known inhibitor of viral reverse transcriptase, an enzyme necessary for human immunodeficiency virus replication. U.S. Pat. No. 4,724,232 claims a method of treating humans having acquired immunodeficiency syndrome utilizing 3'-azido-3'-deoxy-thymidine (azidothymidine, AZT).

Following the discovery of the anti-HIV activity of AZT, much effort has been focused on a wide variety of other dideoxynucleoside analogues in the search for superior agents. In the case of the 2',3'-dideoxy series, ddC and ddI have shown potent activity against HIV in vitro and have been evaluated in clinical trials. Saunders and Storer, page 160. The compound ddC is currently being developed by Hoffman-La Roche Co. as a potential anti-AIDS drug. Its limiting toxicity in humans is peripheral neuropathy which is reversible at low doses. Raymond R. Schinazi, Jan R. Mead and Paul M. Feorino, "Insights Into HIV Chemotherapy," AIDS Research and Human Retroviruses, Vol. 8, Number 6, 1992, pages 963–990. It has been approved by the FDA for AIDS therapy in combination with AZT. The compound ddI has also been evaluated in clinical trials. Its limiting toxicities are peripheral neuropathy and pancreatitis. It has also been shown to stimulate hepatic glycolysis leading to irreversible liver damage. Schinazi, Mead and Feorino, page 966. It has recently been approved by the FDA for the treatment of HIV-1 infections in adults and pediatric patients who are intolerant to or whose health has significantly deteriorated while on AZT treatment. Schinazi, Mead and Feorino, page 966.

Among these approved drugs, AZT is currently the only drug that has been shown to decrease the morality and frequency of opportunistic infections associated with AIDS. Schinazi, Mead and Feorino, page 963.

Human immunodeficiency virus (HIV) has long been recognized as the causative agent in AIDS, although a minority opinion to the contrary has been expressed (e.g., P. Duesberg, Proc. Natl. Acad. Sci., USA, 86:755–764 (1989)). Sequence analysis of the complete genomes from several infective and non-infective HIV-isolates has shed considerable light on the make-up of the virus and the types of molecules that are essential for its replication and maturation to an infective species. The HIV protease is essential for the processing of the viral gag and gag-pol polypeptides into mature virion proteins. L. Ratner, et al., Nature, 313:277–284 (1985); L. H. Pearl and W. R. Taylor, Nature, 329:351 (1987). HIV exhibits the same gag/pol/env organization seen in other retroviruses. L. Ratner, et al., above; S. Wain-Hobson, et al., Cell, 40:9–17 (1985); R. Sanchez-Pescador, et al., Science, 227:484–492 (1985); and M. A. Muesing, et al., Nature, 313: 450–458 (1985).

Reverse transcriptase (RT) is an enzyme unique to retroviruses that catalyzes the conversion of viral RNA into double stranded DNA. Blockage at any point during the transcription process, by AZT or any other aberrant deoxynucleoside triphosphate incapable of elongation, should have dramatic consequences relative to viral replication. Much work on the RT target is in progress based, in large measure, upon the fact that nucleosides like AZT are easily delivered to cells. However, the inefficiency of phosphorylation steps to the triphosphate, and the lack of specificity and consequent toxicity, constitute major drawbacks to use of AZT and similar nucleosides having a blocked, or missing, 3'hydroxyl group.

The T4 cell receptor for HIV, the so-called CD4 molecule, has also been targeted as an intervention point in AIDS therapy. R. A. Fisher, et al., Nature, 331:76–78 (1988); R. E. Hussey, et al., Nature, 331:78–81 (1988); and K. C. Deen, et al., Nature, 331:82–84 (1988). The exterior portion of this transmembrane protein, a molecule of 371 amino acids (sCD4) has been expressed in Chinese hamster ovary (CHO) cells and Genentech (D. H. Smith, et al., Science, 238:1704–1707 (1987)) has had a product in clinical trials since the fall of 1987. CD4 has been shown to have a narrow spectrum of activity against wild-type virus and so far has failed to control HIV infection in humans. Schinazi, Mead and Feorino, page 963. The idea behind CD4 based therapy is that the molecules can neutralize HIV by interfering with viral attachment to T4, and other cells which express CD4 on their surfaces. A variant on this theme is to attach cell toxins to CD4 for specific binding and delivery to infected cells which display glycoprotein gp-120 on their surfaces. M. A. Till, et al., Science, 242:1166–1168 (1988); and V. K. Chaudhary, et al., Nature, 335:369–372 (1988).

Another therapeutic target in AIDS involves inhibition of the viral protease (or proteinase) that is essential for processing HIV-fusion polypeptide precursors. In HIV and several other retroviruses, the proteolytic maturation of the gag and gag/pol fusion polypeptides (a process indispensable for generation of infective viral particles) has been shown to be mediated by a protease that is, itself, encoded by the pol region of the viral genome. Y. Yoshinaka, et al., Proc. Natl. Acad. Sci. USA, 82:1618–1622 (1985); Y. Yoshinaka, et al., J. Virol., 55:870–873 (1985); Y. Yoshinaka, et al., J. Virol., 57:826–832 (1986); and K. von der Helm, Proc. Natl. Acad. Sci., USA, 74:911–915 (1977). Inhibition of the protease has been shown to inhibit the processing of the HIV p55 in mammalian cell and HIV replication in T lymphocytes. T. J. McQuade, et al., Science, 247:454 (1990).

The protease (or proteinase), consisting of only 99 amino acids, is among the smallest enzymes known, and its demonstrated homology to aspartyl proteases such as pepsin and renin (L. H. Pearl and W. R. Taylor, Nature, 329: 351–354 (1987); and I. Katoh, et al., Nature, 329:654–656 (1987)), led to inferences regarding the three-dimensional structure and mechanism of the enzyme (L. H. Pearl and W. R. Taylor, above) that have since been borne out experimentally. Active HIV protease has been expressed in bacteria (see, e.g., P. L. Darke, et al., J. Biol. Chem., 264:2307–2312 (1989)) and chemically synthesized (J. Schneider and S. B. Kent, Cell, 54:363–368 (1988); and R. F. Nutt, et al., Proc. Natl. Acad. Sci., USA 85:7129–7133 (1988)). Site directed mutagenesis (P. L. Darke, et al., above); and N. E. Kohl, et al., Proc. Natl. Acad. Sci., USA, 85:4686–4690 (1988)) and pepstatin inhibition (P. L. Darke, et al., J. Biol. Chem., 264:2307–2312 (1989); S. Seelmeier, et al., Proc. Natl. Acad. Sci., USA, 85:6612–6616 (1988); C.-Z. Giam and I. Borsos, J. Biol. Chem., 263:14617–14720 (1988); and J. Hansen, et al., EMBO J., 7:1785–1791 (1988)) have provided evidence for HIV protease's mechanistic function as an aspartyl protease. A study has demonstrated that the protease cleaves at the sites expected in peptides modeled after the regions actually cleaved by the enzyme in the gag and pol precursor proteins during viral maturation. P. L. Darke, et al., Biochem. Biophys. Res. Communs., 156:297–303 (1988). X-ray crystallographic analysis of the HIV-protease (M. A. Navia, et al., Nature, 337:615–620 (1989)) and a related retroviral enzyme from Rous sarcoma virus (M. Miller, et al., Nature, 337:576–579 (1989)) reveal an active site in the protease dimer that is identical to that seen in other aspartyl proteases, thus supporting the supposition (L. H. Pearl and W. R. Taylor, above) that the HIV enzyme is active as a dimer. See also Joseph A. Martin, "Recent Advances in the Design of HIV Proteinase Inhibitors," Antiviral Research, 17 (1992) 265–278.

To date, the scientific search for a fully effective and safe means of inhibiting retroviruses in a human hosting such a virus, and thereby effectively treating diseases caused by such a virus, such as acquired immunodeficiency syndrome (AIDS), continues.

INFORMATION DISCLOSURE

Published unexamined Japanese patent application 1-319488, Dec. 25, 1989, from Nikken Chemicals Co. Ltd. describes the synthesis and antiulcer utility of tetrahydroimadazo[2,1-b]benzothiazole derivatives, including -3-methanol derivatives. Specifically disclosed are 3 formyl-2-methyl-5,6,7,8-tetrahydro[2,1-b]benzothiazole and 2-methyl-5,6,7,8-tetrahydro[2,1-b]benzothiazole-3-methanol.

Japanese patent 2-306918 (Dec. 20, 1990), from Nikken Chemicals Co. Ltd. describes imidazo[2,1-b]thiazole derivatives such as 6-methyl-5-hydroxymethanol, 5-(1-hydroxybenzyl)-6-methyl, 3,6-dimethyl-5-(1-hydroxybenzyl) derivatives.

Japanese patent 2-178289 (Jul. 11, 1990) describes imidazo[2,1-b]thiazoles for treatment of ulcers and for improvement of cerebral function.

Japanese patent 2-306917 (Dec. 20, 1990) from Nikken Chemical Co. Ltd. describes imidazo[2,1-b]thiazoles derivatives such as 3,6-dimethyl compounds which have appended 5-carboxaldehyde, 5-hydroxymethyl and 5-carboexthoxy substituents.

European patent 0 347 880 from Nikken Chemical Co. Ltd., describes imidazo[2,1-b]benzothiazoles derivatives such as: 2-methylimidazo[2,1-b]benzothiazole-3-methanol hydrochloride; 3-(1-hydroxyethyl)-2-methyl[2,1-b] benzothiazole; imidazo[2,1-b]benzothiazole-3-methanol; 3-(60-hydroxybenzyl-2-methylimidazo[2,1-b] benzothiazole; 7-methoxy-2-methylimidazo[2,1-b] benzothiazole-3-methanol; and 7-fluoro-2-methylimidazo [2,1-b]benzothiazole-3-methanol.

European patent 0 463 212 from Nikko Chemical Co. Ltd. describes imidazo[2,1-6]thiazole-5-methanol compounds including 3,6-dimethylimidazo[2,1-b]thiazole-5-methanol.

Costakis et al., Chem. Chron., 1978, 7, 171 (CA 91:20398t), describes the synthesis of 2-chloro-3-(α-phenyl) and 2-chloro-3-(α-methyl) substituted phenyl imidazo[2,1-b]benzothiazole-3-methanol derivatives as well as the corresponding 2,3-unsubstituted-6-chloro-5-(α-phenyl) and 5-(α-substituted phenyl) imidazo [2,1-b]thiazole-5-methanol derivatives.

Abigmente et al., Il Famaco Ed. Sci., 1983, 38, 533, discloses a series of 6 -methylimidazo[2,1-b]thiazole-5-carboxylic acid and 2-methylimidazo[2,1-b]benzothiazole-3-carboxylic acids, as well as their corresponding esters.

Andreani et al., Eur. J. Med. Chem. Chim. Ther., 1986, 21 451, discloses 2,3-unsubstituted and 2,3-dihydroimidazo[2, 1-b]thiazole 5-carboxylic acids and their corresponding esters.

Compton et al., J. Chem. Soc. Perkin Trans., 1, 1992, 2029, disclose the synthesis of methyl substituted (2,6-dimethyl, 2-methyl, 3-methyl-6-phenyl and 6-phenyl) imidazo[2,1-b]thiazoles synthesized by direct condensation with 2-aminothiazoles.

Robert et al., J. Heterocyclic Chem., 1979, 16, 1201, report imidazo[2,1-b]thiazole-5-methane derivative, especially 2,3-unsubstituted-methyl and -phenyl methanes.

Tisler et al. Heterocycles, 1986, 24, 279, disclose the synthesis of (imidazo[2,1-b]thiazol-5-yl)phenyl methanone derivatives.

The following references disclose various imidazo[2,1-b] thiazole-5-carboxyaldehyde and aldehyde derivatives:

European patent 0 164 635 (CA 104:224897b) disclose hydrazone derivatives having diuretic and antihypertensive activities;

Yaoxue Zazhi, 1992, 44, 517 (CA 118:212949w) disclose 6-phenyl derivatives having antiinflammatory activities;

J. Med. Chem., 1992, 35, 4634, disclose 2,3-dihydro and 2,3-unsubstituted aminoguanidine derivatives having antitumor activity;

Pharma. Acta Helv., 1992, 67, 195 (CA 117:171315u) disclose hydrazone sulfonamide compounds having diuretic activity;

Andreani et al., Coll. Czech. Chem. Commun., 1991, 56, 2436) disclose 3,6-dimethyl-5-carboxaldehyde derivatives having herbicidal activities;

O'Daley et al., *J. Chem. Soc. Perkin Trans.*, 1, 1991, 855, disclose the synthesis of 6-substituted and 3,6-disubstituted imidazothiazoles including the 3,6-dimethyl-5-carboxaldehyde;

Carloni et al., *J. Heterocyclic Chem.*, 1989, 26, 525, disclose imidazo[2,1-b]thiazole-5-carboxaldehydes, notable 6-chloro and 6-phenyl derivatives, having insecticidal activity;

Andreani et al., *Eur. J. Med. Chem.*, 1988, 23, 385 and *Il Farmaco, Ed. Sci.*, 1980, 35, 573, ibid, 1980, 35, 896, disclose 5-carboxaldehyde-6-phenyl derivatives having antitumor activity; and

*Acta. Pharma. Nord.*, 1992, 4, 93 (CA 111:208690t) discloses 6-chloro-2,3-unsubstituted-5-carboxaldehyde hydrazone derivatives having antihypertensive activity.

To the best of our knowledge, from our review, these references do not disclose the use of these compounds as HIV protease inhibitors. They are disclosed as being used or having activity as: antiulcer agents, agents for improving cerebral function, antiinflammatory, analgesic and antipyretic activity, cardiotonics, antihypertensives, antitumor activity, diuretic activity, anticonvulsant agent, immunomodulators, immunoenhancers or immunosuppressants, neoplasm inhibitors, herbicidal activity and insecticidal activity.

SUMMARY OF THE INVENTION

The present invention provides:

A compound of the formula I
wherein $R_1$ is —H or —$CH_3$;
wherein $R_2$ is —H or —$CH_3$; or
wherein $R_1$ and $R_2$ taken together are
  a) the moiety of formula II, or
  b) the moiety of formula III,
wherein p is 1 to 4 inclusive; or
wherein $R_6$ is
  a) —H,
  b) —$CH_3$,
  c) —F, or
  d) —$OCH_3$;
wherein $R_3$ is
  a) —$CH_2C_6H_5$,
  b) —$CH_2CH_2C_6H_5$,
  c) —$CH_2CH_2CH_2C_6H_5$,
  d) —$CH_2CH_2CH_2CH_2C_6H_5$,
  e) —$CH_2CH(CH_3)C_6H_5$,
  f) —$CH_2CH_2C_6H_4X$,
wherein X may occupy either the ortho, meta or para-positions and is
  i) F,
  ii) Cl,
  iii) Br,
  iv) $OCH_2R_1$,
  v) $N(CH_3)_2$,
  vi) $NHSO_2CH_2R_1$,
  vii) $SCH_3$
  viii) $NHCOCH_2R_1$, or
  ix) $NHSO_2C_6H_4X_1$,
  wherein $X_1$ is
    a. H,
    b. $CH_3$,
    c. F, or
    d. CN;
  g) —CH=CH—$C_6H_5$, (cis or trans);
  h) —C≡C—$C_6H_5$);
  i) CH=CH—$C_6H_3X_2$
  wherein $X_2$ is
    a. F,
    b. Cl,
    c. $OCH_3$, or
    d. —O—$CH_2O$;

j) $CH_2CH_2$— 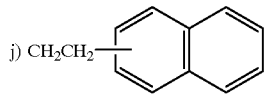

wherein $CH_2CH_2$ is appended to the 1- or 2-positions; or k) —$CH_2CH_2$— 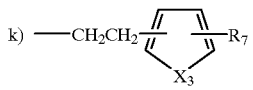

wherein
  i) —$CH_2CH_2$— is appended to the 2- or 3-positions,
  ii) $X_3$ is
    a. O,
    b. S,
    c. NH, and
    d. N—$CH_3$
  iii) $R_7$ is appended to the 4- or 5-positions and is
    a. $CH_3$, or
    b. $CH_3CH_2$;
wherein $R_4$ is —H or —$CH_3$; and
wherein $R_5$ is —H or —$CH_3$;
provided that when $R_1$ is —$CH_3$ and $R_2$ is —H or —$CH_3$, $R_3$ and $R_4$ are not —H.

The compounds of the present invention are named according to the IUPAC or CAS nomenclature system.

The compounds of formula I of the present invention inhibit retroviral proteinases and thus inhibit the replication of the virus. They are useful for treating patients infected with human immunodeficiency virus (HIV) which results in acquired immunodeficiency syndrome (AIDS) and related diseases.

More particularly, the compounds of the present invention are useful as novel human retroviral protease inhibitors. Therefore, the compounds inhibit retroviral proteases and thus inhibit the replication of the virus. They are useful for treating human patients infected with a human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases.

The capsid and replicative enzymes (i.e. protease, reverse transcriptase, integrase) of retroviruses are translated from the viral gag and pol genes as polyproteins that are further processed by the viral protease (PR) to the mature proteins found in the viral capsid and are necessary for viral functions and replication. If the PR is absent or nonfunctional, the virus cannot replicate. The retroviral PR, such as HIV-1 PR, has been found to be an aspartic protease with active site characteristics similar to those exhibited by the more complex aspartic protease, renin.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses.

Patients to be treated would be those individuals: 1) infected with one or more strains of a human retrovirus as determined by the presence of either measurable viral antibody or antigen in the serum and 2) in the case of HIV, having either an asymptomatic HIV infection or a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4+ lymphocyte count of less than 500/mm$^3$ in the peripheral blood. Treatment would consist of maintaining an inhibitory level of the compound used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) which has been recognized as the causative agent in human acquired immunodeficiency syndrome (AIDS), P. Duesberg, Proc. Natl. Acad. Sci. USA, 86:755 (1989). HIV contains a retro viral encoded protease, HIV-I protease, that cleaves the fusion polypeptides into the functional proteins of the mature viral particle, E. P. Lillehoj, et al., J. Virology, 62:3053 (1988); C. Debuck et al., Proc. Natl. Acad. Sci., 84:8903 (1987). This enzyme, HIV-I protease, has been classified as an aspartyl protease and has a demonstrated homology to other aspartyl proteases such as renin, L. H. Pearl, et al., Nature 329:351 (1987); I. Katoh, et al., Nature 329:654 (1987). Inhibition of HIV-I protease blocks the replication of HIV and thus is useful in the treatment of human AIDS, E. D. Clerq, J. Med. Chem. 29:1561 (1986). Inhibitors of HIV-I protease are useful in the treatment of HIV-infected individuals who are asymptomatic or symptomatic of AIDS.

Pepstatin A, a general inhibitor of aspartyl proteases, has been disclosed as an inhibitor of HIV-I protease, S. Seelmeier, et al., Proc. Natl. Acad. Sci. USA, 85:6612 (1986). Other substrate derived inhibitors containing reduced bond isosteres or statine at the scissle position have also been disclosed, M. L. Moore, et al., Biochem. Biophys, Res. Commun. 159:420 (1989); S. Billich, et al., J. Biol. Chem. 263:17905 (1988); Sandoz, D. E. 3812-576-A.

Thus, the compounds of the present invention are useful for treating diseases caused by retroviruses, such as human acquired immunodeficiency disease syndrome (AIDS).

The compounds are also useful for treating non-human animals infected with a retrovirus, such as cats infected with feline leukemia virus. Other viruses that infect cats include, for example, feline infectious peritonitis virus, calicivirus, rabies virus, feline immunodeficiency virus, feline parvovirus (panleukopenia virus), and feline chlamydia. Exact dosages, forms and modes of administration of the compounds of the present invention to non-human animals would be apparent to one of ordinary skill in the art, such as a veterinarian.

The compounds of formula I of the present invention are prepared, generally, as described in the Schemes below and, specifically, as in the Charts, Preparations and Examples below, or are prepared by methods analogous thereto, which are readily known and available to one of ordinary skill in the art of organic synthesis.

The 2-aminothiazoles (Compounds 1a-1g) of Scheme I are either commercially available or, in the case of cycloalkyl derivatives, are synthesized by condensing the corresponding halo ketone with thiourea as described in the literature (U.S. Pat. No. 4,321,372; King, L. C., Hlavacek, R. J., *J. Am. Chem. Soc.*, 1950, 72, 3722). The 2-aminothiazoles (1a-1g) were converted to amidines (2a-2g) by reaction with dimethylformamide dimethyl acetal ($R_{13}$=H) or with dimethylacetamide dimethyl acetal ($R_{13}$=CH$_3$). These condensation reactions were performed in accordance with the work of Fajgeli et al., *Heterocycles*, 1986, 24, 379.

The thiazolium salts (3, X=Cl$^-$, Br$^-$), obtained by reaction of the amidines (Compounds 2) with neat ethyl or methyl haloacetates (e.g., BrCH$_2$CO$_2$CH$_2$CH$_3$), phenacyl-halides (e.g., phenylacylbromide) or haloacetone (ClCH$_2$COCH$_3$) readily found hydrates during recrystallization. Because the water of hydration is deleterious to yields in subsequent conversions, the salts were usually employed as precipitated from the reations.

The imidazo[2,1-b]thiazole ring of Compounds 4 is conveniently generated by cyclizations of the thiazolium salts with amine, alkali metal alkoxides or alkali metal hydride bases. 1,8-Diaza-bicyclo[5,4,0]undec-7-ene (DBU) is a convenient basic amine useful under the anhydrous conditions for the conversions. The corresponding α-alkyl (e.g., $R_{15}$=CH$_3$) α-substituted carbinols (6a-6g) are prepared by the reaction of the methyl ketone (Compound 4) with Grignard reagent. For example, additions of the Grignard reagents, derived from phenethyl bromide, to the ketones (4a-4g) produces the target imidazothiazole phenethyl carbinols (6a-g, $R_{14}$=CH$_3$, $R_{15}$=(CH$_2$)$_n$C$_6$H$_4$X (n=1–4, X=F, CL, Br, OCH$_3$).

Reduction of the ester of the imidazo[2,1-b]carboxylates (Compounds 4, $R_{14}$=OCH$_3$, OCH$_2$CH$_3$) with LiAlH$_4$ provide the intermediate primary carbinols (Compounds 5, $R_{14}$=H) as an intermediate to the corresponding aldehydes (Compounds 7). The aldehydes are prepared by oxidation of the primary alcohols (Compounds 5, $R_{14}$=H) with MnO$_2$ in refluxing toluene. The aldehydes provide an alternative intermediate for the addition of phenyl and substituted Grignard reagents or phenyl lithium reagent in the preparation of α-phenyl methanols. These aldehydes are readily condensed with phenylethyl, benzyl, phenylpropyl, or phenylbutyl magnesium bromide derivatives to elaborate the corresponding side chains of Compounds 8a-8g [$R_{16}$=(CH$_2$)$_n$C$_6$H$_4$X (n=1–4; X=H, F, CL, Br, OCH$_3$, N(CH$_3$)$_2$].

Scheme 2 illustrates the use of the methyl ketones 4a-4g for 2-carbon homologation to the enones (Compounds 9). The aldehyde partners for condensation with methyl ketones are commercially available in the cases of aryl and unsubstituted heterocyclic aldehydes. Substituted heterocyclic aldehydes were available from literature preparations, for example: *J. Org. Chem.*, 1950, 15, 1177; *J. Org. Chem.*, 1954, 19, 70; *J. Org. Chem.*, 1984, 49, 4602; *J. Org. Chem.*, 1985, 50, 2832; *J. Org. Chem.*, 1987, 52, 104; *J. Org. Chem.*, 1987, 52, 2315; Ziegler et al., *Tetrahedron Letters*, 1981, 22, 4883; *Tetrahedron*, 1983, 39, 1893; Lund, T.,*Acta. Chem. Scand., See B.,* 1985 B39, 429; H. Kotsuki et al., *Chem. Lett.*, 1983, 1007. Reduction of the enones with reagents known to favor 1,4-reduction (sodium dithionite after Camps et al., *Tetrahedron*, 1986, 42, 4603; Pd/C-limonene according to Von Holleben et al., *Tetrahedron*, 1994, 50, 973; or Pd$^{+2}$/potassium formate as described in Arcadi, A. et al., *Syn. Lett.*, 1991, 27 or sodium hydrogen telluride after the procedure of Tamashita et al, *J. Org. Chem.*, 1994, 59, 3500) give the saturated aryl- or heteroarylethyl ketones (11a-11-g). Hydroalumination reaction (Koch et al., *Tetrahedron Letters,* 1994, 35, 1137) provide the saturated alcohols (12) directly. Reduction reagents which favor 1,2-reduction provide the allylic alcohols (10a-10g). The saturated ketones (11a-11g) are converted, respectively, with sodium borohydride or Grignard reagents to the secondary methanols (12a-12g) or teriary methanols (13a-13g).

The imidazo[2,1-b]benzothiazole derivatives are synthesized as in Scheme 3. The 2-aminobenzothiazoles 14 are commercially available through Aldrich Chemical Company or other vendors. The amidines (15a-15c), benzothiazolium salts (16a-16e) and imidazobenzothiazole esters (17a-17e) follow from the chemistry of the methyl or cycloalkyl derivatives in Scheme 1.

The other compounds of Scheme 3 are generated via the primary alcohols (18), aldehydes (19) as illustrated in Scheme 1 for the conversion of the carboxylic acid ester to the primary alcohols with lithium aluminum hydride and for conversion of the alcohols, in turn, to the aldehydes with manganese oxide. The aldehydes (19) are reacted with the Grignard reagent derived from phenethyl bromide to produce the corresponding imidazobenzothiazole-3-phenylethyl carbinols (20).

As is apparent to those of ordinary skill in the art, the compounds of the present invention can occur in racemic or enantiomeric forms, depending on the configuration around the asymmetric carbon atoms. All such forms are included within the scope of the present invention.

The present invention provides for compounds of formula I or phamacologically acceptable salts and/or hydrates thereof. Pharmacologically acceptable salts refers to those salts which would be readily apparent to a manufacturing pharmaceutical chemist to be equivalent to the parent compound in properties such as formulation, stability, patient acceptance and bioavailability. Examples of such salts include the hydrohalide salts, such as the hydrochloride and hydroiodide salts, the sodium salt, the potassium salt, and the calcium salt.

The compounds of the present invention are useful for treating patients infected with human immunodeficiency virus (HIV) which results in acquired immunodeficiency syndrome (AIDS) and related diseases. For this indication, these compounds may be administered by oral, intranasal, transdermal, subcutaneous and parenteral (including intramuscular and intravenous) routes in doses of 0.1 mg to 100 mg/kg of body weight per day.

Those skilled in the art would know how to formulate the compounds of this invention into appropriate pharmaceutical dosage forms. Examples of the dosage forms include oral formulations, such as tablets or capsules, or parenteral formulations, such as sterile solutions.

When the compounds in this invention are administered orally, an effective amount is from about 0.1 mg to 100 mg per kg of body weight per day. Either solid or fluid dosage forms can be prepared for oral administration. Solid compositions are prepared by mixing the compounds of this invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum. Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of this invention are administered parenterally, they can be given by injection of by intravenous infusion. An effective amount is from about 0.1 mg to 100 mg per kg of body weight per day. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

Patients to be treated would be those individuals: 1) infected with one or more than one strain of a human immunodeficiency virus as determined by the presence of either measurable viral antibody or antigen in the serum and 2) having either an asymptomatic HIV infection or a symptomatic AIDS defining infection such as i) disseminated histoplasmosis, ii) isoporiasis, iii) bronchial and pulmonary candidiasis including pneumocystis pneumonia, iv) non-Hodgkin's lymphoma, or v) Kaposi's sarcoma and being less than sixty years old; or having an absolute CD4+ lymphocyte count of less than 500/mm$^3$ in the peripheral blood. Treatment would consist of maintaining an inhibitory level of the compounds of this invention in the patient at all times and would continue until the occurrence of a second symptomatic AIDS defining infection indicates alternate therapy is needed.

The utility of representative compounds of the present invention has been demonstrated in the biological tests described below:

The HIV protease screening assay is based on fluorescently labeled substrate which can be resolved from nonlabeled cleavage product using special beads coated with streptavidin. The substrate is biotinylated at the amino terminal arginine and fluorescently labeled with fluorescein isothiocynate (FITC) at the carboxyl terminal lysine. This assay has been employed to detect novel, nonpeptidic inhibitors of HIV-1 protease. Substrate (20 $\mu$l of 0.2 $\mu$M), sample (10 $\mu$l of desired concentration), and enzyme (10 $\mu$l of 0.1 $\mu$M) are added to a 96 well pandex plate. The assay is run in 0.1 M sodium acetate buffer at pH 5.5 in the presence of 1.0 M sodium chloride and 0.05% NP-40 with incubated in the dark for one hour at room temperature. Strepavidin coated polystyrene beads {40 $\mu$l of 0.1% (w/v)} are added and the plate is incubated in the dark for an additional half hour. The labeled cleavage product is separated from the unreacted substrate via filtration and is read on the Idexx screen machine. The data are analyzed by appropriate computer algorithms to ascertain percent inhibition values.

Determination of $K_i$ values utilizes the same materials and equipment employed for percent inhibition studies. Two-fold serial dilutions are made for a given inhibitor from 2, 3 or 4 starting concentrations with a total of 24, 36 or 48 individual inhibitor concentrations. These dilutions are performed utilizing the BioMek robotics system. The assay consists of 10 μL or 40 nM HIV-1 protease, 10 μL of the various inhibitor concentrations, and 20 μL of 200 μM substrate (40 μL total). The reaction is allowed to proceed for 90 min at room temperature, terminated with 40 μL of avidin beads and processed (supra vide). An inhibitor with a known $K_i$ is run in parallel to verify the validity of the assay. The data is processed utilizing a computer program employing a nonlinear least square analysis of the data to generate the $K_i$ values.

The % inhibition values and, in some instances, $IC_{50}$ values or $K_i$ values, of representative compounds of the present invention are listed in Table 1–Table 9 below.

The compounds of the present invention can be further evaluated in a CV-1 cellular assay described below, where it was demonstrated that the retrovirus-inhibiting effect was due to the inhibition of HIV-1 protease:

Inhibition of p55 Processing in vVk-1 infected CV-1 Cells. CV-1 cells are seeded at $2 \times 10^5$ cells per well in 24-well Costar dishes and infected 4 to 6 hours later with vVK-1 at 5 plaque-forming units (PFU) per cell. Each compound is dissolved in Dulbecco's Modified Eagles medium (DMEM) containing 2.5% fetal bovine serum and is added to duplicate wells at the indicated final concentration 2 hours after virus addition. After 24 hours, the culture medium is removed and the monolayer washed with 1 mL of phosphate buffered saline (PBS), and the cells lysed by the addition of 0.1 mL of loading buffer (62.5 mM Tris (hydroxymethyl) aminomethane (Tris), pH 6.8, 2.3% sodium dodecyl sulfate (SDS), 5% β-mercaptoethanol, and 10% glycerol). The cell lysates are collected individually, placed in boiling water for 3 minutes, and then 0.025 mL of each sample is subjected to electrophoresis on 12% SDS-polyacrylamide gels. The proteins are electroblotted onto nitrocellulose and analyzed by protein immunoblotting. The primary antibodies are sheep antibody to p24 (International Enzyme, Inc., Fallbrook, Calif.) and the secondary antibody is alkaline-phosphatase-conjugated rabbit antibody to sheep immunoglobulin G (Kirkegaard & Perry Laboratories, Gaithersburg, Md.). The levels of immunoreactive proteins are quantified by densitometry (Bio-Rad, Model 260) with the accompanying 1-D Analyst Software. Inhibition refers to the mean percent decrease in p24 levels determined from the duplicate drug-treated samples compared to the nondrug-treated controls. In general, the percent inhibition did not vary more than 10% in the duplicates. The inhibition of p24 levels by treatment of cultures with 1 μM of peptide 1-Noa-His-Cha PSI [CHOHCHOH] Val-Ile-Amp (also known as N-[1-(cyclohexylmethyl)-2,3-dihydroxy-5-methyl-4-[[[2-methyl-1-[[(2-pyridinylmethyl)amino]carbonyl]butyl] amino]carbonyl]hexyl]-α-[[(1-naphthalenyloxy)acetyl] amino]-, [1S-[1R*(R*),2S*,3S*,4S*(1R*,2R*)]]-1-H-imidazole-4-propanamide) (which was disclosed in International Publication Number WO 87/05302, published Sep. 11, 1987) was also determined in each experiment.

Several compounds of the present invention, such as 2,3-dimethyl-60-(2-phenylethyl)imidazo[2,1-b]thiazole-5-methanol were tested in known human cell lines, such as human T-cell lines, e.g., H9, which were infected with $HIV-1_{IIIB}$. The compounds were found to inhibit retroviral replication. The H9 cell line was originally derived from the peripheral blood of a human lymphoma patient and extensively cloned so that the cells were highly susceptible to HIV infection. Virus-free H9 cells were maintained in a humidified 5% $CO_2$ atmosphere at 37° C. in RPMI Complete (RC) medium, which was composed of RPMI 1640 supplemented with 10% heat-inactivated fetal calf serum (FCS), 10 mM Hepes, 2 mM L-glutamine, 100 μg/ml streptomycin, and 100 U/ml penicillin. H9 cultures were split 1:5 twice weekly for a maximum 12–15 times. New lots of cells were obtained from cryopreserved samples frozen in liquid nitrogen vapor and maintained in RPMI 1640 containing 20% FCS, 10 mM Hepes, 2 mM L-glutamine, 100 U/ml penicillin, 100 μg/ml streptomycin, and 7.5% DMSO.

$HIV_{IIIb}$'s ability to replicate efficiently in human T lymphoblastoid cell lines made this strain of HIV the logical choice for protease inhibitor screen. Viral stocks were created by acutely infecting $2 \times 10^6$ H9 cells contained in 1 ml RC medium at a multiplicity of infection of 0.1. The infected cells were transferred to 50 ml of RC, and split 1:3 biweekly, with cell viability ranging from 65–80%. Fourteen days after the infection was established, culture supernatant was removed and frozen at −80° C. with no preservatives added. The supernatant, containing a high titer of $HIV_{IIIb}$ particles, was thawed, centrifuged at 200×g to remove cell debris, then distributed in 0.5 ml aliquots to cryogenic vials. The titer, measured at the 50% Tissue Culture Infectious Dose ($TCID_{50}$), was determined by the Reed-Muench method of statistical analysis to determine the 50% infectivity endpoint.

The standard acute infectivity assay for the evaluation of the inhibitors of HIV protease was performed in 96 well microplates. H9 cells were washed and resuspended to a concentration of $2 \times 10^6$ cells/ml in RC Medium. 25 μl of H9 cells were distributed to the appropriate wells of a microtiter plate so that the final concentration of cells was $5 \times 10^4$/well. To each well except negative controls, 25 μl of $HIV_{IIIb}$ containing approximately 50 $TCID_{50}$'s was added, achieving a multiplicity of infection of 0.001. Finally, 25 μl of 3× drug was added to the wells. To the control well, 25 μl of either RC medium or RC+DMSO was added. The amount of DMSO utilized in the control wells was equivalent to the DMSO content of the test drugs. The microplates were incubated in a humidified 5% $CO_2$ atmosphere for 2 h at 37° C. At the end of the incubation period, an additional 175 μl of 1× drug, RC medium, or RC+DMSO was added to each test well, and the plates incubated for 7 days at 37° C. in 5% $CO_2$. Each drug concentration was tested in triplicate. Each compound was originally tested at 100, 10 and 1 nM to assess anti-HIV activity, and active compounds were retested using serial 0.5 $log_{10}$ dilutions beginning at concentrations of 100 nM or below. After four days of incubation, 125 μl of the cell culture supernatant in each well was removed without disturbing the cells and replaced with 125 μl of fresh RC Medium, RC+DMSO, or RC+1× drug. At the end of the 7 day incubation period, 100 μl of supernatant was removed from each test well and live virus inactivated by the addition of lysis buffer containing 5% Triton X-100. The amount of HIV p24 core antigen was quantified with an ELISA procedure by following the manufacturers directions (Coulter Diagnostics). The $IC_{50}$ (Inhibitory Concentration$_{50}$), the amount of drug necessary to reduce the concentration of p24 in drug-containing cultures by 50% when compared with drug-free controls, was calculated by comparing the concentration of p24 antigen from the drug test wells to the p24 levels found in the drug-free control growth wells.

An in vitro assay capable of assessing the activity of antiviral compounds against $HIV_{IIIb}$ in H9 cells was developed. The assay compares the ability of the human immunodeficiency virus to replicate in the presence or absence of drug. Replication is assessed by the ability of the virus to produce p24 core antigen, as determined by an ELISA technique. Production of p24 in the presence of drug is compared with drug-free controls, and the Inhibitory Concentration$_{50}$ (IC$_{50}$) calculated by linear regression.

The following compounds of the present invention are preferred:

2,3-Dimethyl-α-(2-phenylethynyl)imidazo-[2,1-b]thiazole-5l-methanol,
2,3-Dimethyl-α-(2-phenylmethyl)imidazo-[2,1-b]thiazole-5-methanol,
2,3-Dimethyl-α-(3-phenylpropyl)imidazo-[2,1-b]thiazole-5-methanol,
2,3-Dimethyl-α-Di(2-phenylethyl)imidazo-[2,1-b]thiazole-5-methanol,
α,3-Dimethyl-α-(E-2-phenyl-E-ethenyl)imidazo[2,1-b]thiazole-5-methanol,
3-Methyl-α-(2-phenylpropyl)imidazo[2,1-b]thiazole-5-methanol,
α,3-Dimethyl-α-(2-phenylethyl)imidazo[2,1-b]thiazole-5-methanol,
3-Methyl-α-(2-phenylethyl)imidazo[2,1-b]thiazole-5-methanol,
3-Methyl-α-(4-bromophenylethyl)imidazo[2,1-b]thiazole-5-methanol,
3-Methyl-α-(4-phenylbutyl)imidazo-[2,1-b]thiazole-5-methanol,
2,3-Dimethyl-α-(2-phenylethyl)imidazo[2,1-b]thiazole-5-methanol,
2,3-Dimethyl-α-(2-phenylethenyl)imidazo[2,1-b]thiazole-5-methanol,
6,7-Dihydro-α-(2-phenylethyl)-5H-cyclopent[d]imidazo[2,1-b]thiazole-3-methanol,
5,6,7,8-Tetrahydro-α-(2-phenylethyl)imidazo[2,1-b]benzothiazole-3-methanol,
6,7,8,9-Tetrahydro-α-(2-phenylethyl)-5H-cyclohept[d]imidazo[2,1-b]thiazole-3-methanol,
6,7,8,9-Tetrahydro-α-(4-phenylbutyl)-5H-cyclohept[d]imidazo[2,1-b]thiazole-3-methanol,
5,6,7,8,9,10-Hexahydro-α-(2-phenylethyl)cyclooct[d]imidazo-[2,1-b]thiazole-3-methanol,
α-(2-phenylethyl)-imidazo[2,1-b]benzothiazole-3-methanol,
7-Methyl-α-(2-phenylethyl)imidazo[2,1-b]benzothiazole-3-methanol,
7-Fluoro-α-(2-phenylethyl)imidazo[2,1-b]benzothiazole-3-methanol,
7-Methoxy-α-(2-phenylethyl)imidazo[2,1-b]benzothiazole-3-methanol,
α-[2-(3-Fluorophenyl)ethenyl]-6,7,8,9-tetrahydro-5H-imidazo[2,1-b]thiazole-3-methanol
α-[2-(3-Fluorophenyl)ethyl]-6,7,8,9-tetrahydro-5H-cyclohept[d]imidazo[2,1-b]thiazol-3-methanol,
α-[2-(4-Fluorophenyl)ethyl]-6,7,8,9-tetrahydro-5H-cyclohept[d]imidazo[2,1-b]thiazol-3-methanol,
α-[2-(4-Fluorophenyl)ethenyl]-6,7,8,9-tetrahydro-5H-cyclohept[d]imidazo[2,1-b]thiazol-3-methanol,
α-[2-(3-Bromophenyl)ethyl]-6,7,8,9-tetrahydro-5H-cyclohept[d]imidazo-2,1-b]thiazol-3-methanol,
α-[2-(3-Chlorophenyl)ethyl]-6,7,8,9-tetrahydro-5H-cyclohept[d]imidazo[2,1-b]thiazol-3-methanol,
α-[2-(3,5-Difluorophenyl)ethyl]-1-6,7,8,9-tetrahydro-5H-cyclohept[d]-imidazothiazol-3-methanol,
α-[2-(4-dimethylaminophenyl)ethyl-6,7,8,9-tetrahydro-5H-cyclohept[d]imidazo-[2,1-b]thiazol-3-methanol,
α-[2-(4-Dimethylaminophenyl)ethyl]-6,7,8,9-tetrahydro-5H-cyclohept[d]-imidazo[2,1-b]thiazol-3-methanol,
N-[3-[3-(2,3-Dimethylimidazo[2,1-b]thiazol-5-yl)-3-hydroxypropyl]phenyl-4-methylbenzenesulfonamide,
(E)-N-[3-[3-(2,3-Dimethylimidazo[2,1-b]thiazol-5-yl)-3-hydroxy-1-propenyl]phenyl-4-methylbenzenesulfonamide,
N-[2-[3-(2,3-Dimethylimidazo[2,1-b]thiazol-5-yl)-3-hydroxy-propyl]phenyl-4-methylbenzenesulfonamide,
α-[2-(2,3-Difluorophenyl)ethyl]-6,7,8,9-tetrahydro-5H-cyclohept[d]imidazo-thiazol-3-methanol,
α-[2-(4-methoxyphenyl)ethyl]-6,7,8,9-tetrahydro-5H-cyclohept-[d]imidazo[2,1b]thiazol-3-methanol,
α-[2-(4-methoxyphenyl)ethenyl]-6,7,8,9-tetrahydro-5H-cyclohept-[d]imidazo[2,1-b]thiazol-3-methanol,
α-[2-(2-Naphthalenyl)ethyl]-6,7,8,9-tetrahydro-5H-cyclohept[d]imidazo[2,1-b]thiazol-3-methanol,
α-[2-(2-Furanyl)ethenyl]-6,7,8,9-tetrahydro-5H-cyclohept[d]imidazo[2,1-b]thiazol-3-methanol,
α-[2-(2-Furanyl)ethyl]-6,7,8,9-tetrahydro-5H-cyclohept[d]imidazo[2,1-b]thiazol-3-methanol,
α-[2-(3-Furanyl)ethyl]-6,7,8,9-tetrahydro-5H-cyclohept[d]imidazo[2,1-b]thiazol-3-methanol,
α-[2-(2-Furanyl)ethenyl]2,3-dimethylimidazo[2,1-b]thiazol-3-methanol,
α-[2-(2-Furanyl)ethyl]2,3-dimethylimidazo[2,1-b]thiazol-3-methanol, and
1-(2,3-Dimethylimidazo[2,1-b]thiazol-5-yl)-3-phenyl-1,3-propanediol.

DESCRIPTION OF THE PREFERRED EMBODIMENTS

In the Preparations and Examples below and throughout this document:

°C. is degrees Centigrade

M is molar (concentration).

N is normal (concentration).

mL is milliliter.

mg is milligram.

mmHg is millimeter of mercury.

$^1$H-NMR is proton nuclear magnetic resonance spectrum.

$^{13}$C-NMR is carbon nuclear magnetic resonance spectrum.

δ is chemical shift (parts per million) relative to TMS.

CDCl$_3$ is deuterio-chloroform.

CD$_3$OD is deuterio-methanol.

DMSO is deuterio dimethylsulfoxide.

FAB MS is fast-atom-bombardment mass spectroscopy.

EI MS is electron impact mass spectroscopy.

HRMS is high-resolution mass spectroscopy.

Anal. is analytical data.

Pd/C is palladium on charcoal.

THF is tetrahydrofuran.

HOBT is 1-hydroxybenzotriazole hydrate.

R$_f$ is chromatographic movement relative to solvent front.

cm$^{-1}$ is reciprocal centimeters.

TFA is trifluoroacetic acid.

MP is melting point.

TMS is tetramethyl silane.

The following Preparations and Examples, which illustrate the preparation of certain presently preferred compounds according to the invention, are for illustrative purposes only and are not to be construed as limiting the invention.

PREPARATION 1

N'-(4,5-Dimethyl-2-thiazolyl)-N,N-dimethyl-methanimidamide (Formula A-2) Refer to Chart A.

A suspension of 2-amino-4,5-dimethylthiazole hydrochloride (4.92 g, 30 mmol) (Formula A-1) in toluene (60 mL) was treated with triethylamine (4.5 mL, 35 mmol) and vigorously stirred for 30 minutes. The mixture was treated with dimethylformamide dimethyl acetal (7.3 mL, 60 mmol) and heated at reflux temperature for 2 hours. The solution was cooled, diluted with ethyl acetate, washed with saline, dried and evaporated. The residue was crystallized from hexane to provide pure N'-(4,5-Dimethyl-2-thiazolyl)-N,N-dimethyl-methanimidamide (Formula A-2) (4.31 g, 77%), m.p. 47–58°.

Anal. Calc'd for $C_8H_{13}N_3S$: C, 52.42; H, 7.14; N, 22.92; S, 17.49. Found: C, 52.31; H, 7.27; N, 22.87; S, 17.65. MS m/z 183 ($M^+$), 168, 150, 141, 113, 98, 86, and 71. NMR ($CDCl_3$) 2.22 (s, 3, $CH_3$), 2.26 (s, 3, $CH_3$), 3.10 (s, 6, $CH_3$), 8.10 (s, 1, CH).

PREPARATION 2

4,5-Dimethyl-2[[(dimethylamino)methylene]amino-3-(2-ethoxy-2-oxoethyl)-thiazolium bromide (Formula A-3) Refer to Chart A.

A solution of N'-(4,5-Dimethyl-2-thiazolyl)-N,N-dimethyl-methanimidamide (Formula A-2) (13.74 g, 75 mmol) in ethyl bromoacetate (25 mL) solidified within 45 minutes. Additional reagent (15 mL) and toluene (30 mL) were added to maintain fluididy. The mixture was reacted at 25° for 48 hours, diluted with ethyl acetate (200 mL) and the precipitated 4,5-Dimethyl-2[[(dimethylamino)methylene]amino-3-(2-ethoxy-2-oxoethyl)-thiazolium bromide (Formula A-3) (23.49 g, 89%) was filtered. An aliquot was crystallized from acetonitrile to provide an analytical sample, m.p. 178–180°.

Anal. Calc'd for $C_{12}H_{20}BrN_3O_2S$: C, 41.15; H, 5.76; Br, 22.81; N, 12.00; S, 9.15. Found: C, 41.10; H, 5.67; Br, 22.91; N, 11.99; S, 9.19. MS m/z (FAB) 621, 619 ($2M^+$-Br), 270 ($M^+$+H-Br). IR (mull) 1743, 1646, 1628, 1522, 1489, 1434, 1425, 1411, 1397, and 1218 $cm^{-1}$.

PREPARATION 3

2,3-DImethylimidazo[2,1-b]thiazole-5-carboxylic acid ethyl ester (Formula A-4) Refer to Chart A.

A suspension of 4,5-Dimethyl-2-[[(dimethylamino)methylene]amino-3-(2-ethoxy-2-oxoethyl)-thiazolium bromide (Formula A-3) (10.42 g, 29.8 mmol) in DMF (40 mL) was treated with DBU (7.0 mL, 7.17 g, 47.2 mmol). Dissolution of 4,5-Dimethyl-2[[(dimethylamino)methylene]amino-3-(2-ethoxy-2-oxoethyl)-thiazolium bromide (Formula A-3) occurred immediately and the solution was reacted at ambient temperature for 24 hours. The solution was diluted with ice water and precipitated 2,3-Dimethylimidazo[2,1-b]thiazole-5-carboxylic acid ethyl ester (Formula A-4) (4.36 g, 65%) was filtered. The precipitate contained polar by-products which were removed by filtration of the crude product through silica gel (200 g) eluting with 4:1 hexane:ethyl acetate. The eluted product (2.28 g) was crystallized from ethyl acetate-hexane solution to provide pure 2,3-Dimethylimidazo[2,1-b]thiazole-5-carboxylic acid ethyl ester (Formula A-4) (1.77 g), m.p. 60–61°.

Anal. Calc'd for $C_{10}H_{12}N_2O_2S$: C, 53.55; H, 5.39; N, 12.49; S, 14.29. Found: C, 53.43, H, 5.45; N, 12.00; S, 14.10.

MS m/z 224 ($M^+$), 196, 195, 179, 178, 167, 152, 150, 139, 137 and 110.

IR 1721, 1506, 1436, 1395, 1354, 1308, 1216, 1170, 1135, and 1063 $CM^{-1}$.

NMR ($CDCl_3$) δ 1.38 (t, J=7 Hz, 3, $CH_3$), 2.34 (s, 3, $CH_3$), 2.63 (s, 3, $CH_3$), 4.31 (q, J=7 Hz, 2, $CH_2$), 7.93 (s, 1, CH).

PREPARATION 4

2,3-Dimethylimidazo[2,1-b]thiazole-5-methanol (Formula A-5) Refer to Chart A.

A solution of 2,3-Dimethylimidazo[2,1-b]thiazole-5-carboxylic acid ethyl ester (Formula A-4) (1.68 g) in THF (50 mL) at 0° was treated with $LiAlH_4$ (0.38 g) and reacted at 25° for 1.5 hours. Excess reagent was quenched by sequential addition of water and 15% sodium hydroxide. The resulting mixture was diluted with THF (100 mL), filtered, and the filtrate was evaporated to a residue of crude 2,3-Dimethylimidazo[2,1-b]thiazole-5-methanol (Formula A-5) (1.04 g). Crystallization from isopropanol solution gave pure 2,3-Dimethylimidazo[2,1-b]thiazole-5-methanol (Formula A-5), m.p. 166–167°.

Anal. Calc'd for $C_8H_{10}N_2OS$: C, 52.72; H, 5.53; N, 15.37; S, 17.59. Found: C, 52.84; H, 5.54; N, 15.40; S, 17.50.

MS m/z 182 ($M^+$), 165, 153, 129, 128, and 113.

IR (mull) 3188, 3115, 1654, 1335, 1324, 1310, and 1019 $cm^{-1}$.

NMR ($CDCl_3$) δ 2.32 (s, 3, $CH_3$), 2.54 (s, 3, $CH_3$), 4.78 (s, 2, $CH_2$), 7.07 (s, 1, CH).

PREPARATION 5

2,3-Dimethylimidazo[2,1-b]thiazole-5-carboxaldehyde (Formula A-6) Refer to Chart A.

A solution of 2,3-Dimethylimidazo[2,1-b]thiazole-5-methanol (Formula A-5) (4.38 g) in DMF (30 mL) was diluted with toluene (400 mL), treated with $MnO_2$ (8.8 g) and azetropically distilled during 2 hours. The cooled mixture was diluted with ethyl acetate, filtered, and the filtrate was evaporated. The residue was diluted with water and precipitated 2,3-Dimethylimidazo[2,1-b]thiazole-5-carboxaldehyde (Formula A-6) (4.12 g) was filtered. Crystallization from ethyl acetate hexane provided pure 2,3-Dimethylimidazo[2,1-b]thiazole-5-carboxaldehyde (Formula A-6), m.p. 119–120°.

Anal. Calc'd for $C_8H_8N_2OS$: C, 53.33; H, 4.48; N, 15.55; S, 17.79. Found: C, 53.44; H, 4.47; N, 15.64; S, 17.70.

MS m/z 180 ($M^+$), 179, 165, 151, 147, and 110.

IR (mull) 1676, 1671, 1507, 1448, 1389, 1345, 1327, 1301, 1268, 1165 and 1161 $cm^{-1}$.

NMR ($CDCl_3$) 2.36 (s, 3, $CH_3$), 2.69 (s, 3, $CH_3$), 7.97 (s, 1, CH), 9.57 (s, 1, CH).

EXAMPLE 1

2,3-Dimethyl-α-(2-phenylethynyl)imidazo-[2,1-b]thiazole-5-methanol (Formula A-7) Refer to Chart A.

Phenylacetylene (0.73 g) in THF (10 mL) at −65° was treated with 1.6 M n-butyllithium in hexane (0.44 mL). The solution was reacted for 30 minutes then treated with a solution of 2,3-Dimethylimidazo[2,1-b]thiazole-5-carboxaldehyde (Formula A-6) (0.64 g) in THF (10 mL). The solution was reacted at −65° for 1.5 hours then at 25° for 6 hours. Incomplete conversion of 2,3-Dimethylimidazo[2,1-b]thiazole-5-carboxaldehyde (Formula A-6) persisted after 24 hours and the reaction suspension was poured into ice water and products were extracted into ethyl acetate. Drying and evaporation of solvent gave an oil which deposited pure crude 2,3-Dimethyl-α-(2-phenylethynyl)imidazo-[2,1-b]thiazole-5-methanol (Formula A-7) (0.16 g) from hexane. Crystallization from ethanol gave pure 2,3-Dimethyl-α-(2-phenylethynyl)imidazo-[2,1-b]thiazole-5-methanol (Formula A-7).

MS (m/z) 282 (M$^+$), 265, 253, 239, 205, 180, 179, 152, 139, and 129.

NMR (DMSO) δ 2.32 (s, 3, $CH_3$), 2.65 (s, 3, $CH_3$), 6.05 (d, 1, OH), 6.48 (d, 1, CH), 7.32 (s, 1, CH), 7.40–7.60 (m, 5, ArH).

EXAMPLE 2

2,3-Dimethyl-α-(2-phenylmethyl)imidazo-[2,1-b]thiazole-5-methanol (Formula A-8) Refer to Chart A.

Magnesium (0.29 g) in ether (20 mL) was treated with benzyl bromide (0.179 mL) and reacted at ambient temperature for 1.25 hours. Solid 2,3-Dimethylimidazo[2,1-b]thiazole-5-carboxaldehyde (Formula A-6) (0.54 g) was added and the thick suspension reacted for 24 hours. The mixture was poured into cold 5% ammonium chloride solution and the mixture was extracted with ethyl acetate. Evaporation of the extract gave a semi-solid residue (1.22 g) of crude 2,3-Dimethyl-α-(2-phenylmethyl)imidazo-[2,1-b]thiazole-5-methanol (Formula A-8). Trituration of the residue with cold ether gave pure 2,3,-Dimethyl-α-(2-phenylmethyl)imidazo-[2,1-b]thiazole-5-methanol (Formula A-8) (0.59 g). Crystallization of the triturated product from acetonitrile provided an analytical sample, m.p. 170–172°.

Anal. Calc'd for $C_{15}H_{16}N_2OS$: C, 66.15; H, 5.92; N, 10.29; S, 11.77. Found: C, 66.22; H, 5.99; N, 10.49; S, 11.66.

MS m/z 272 (M$^+$), 255, 253, 183, 182, 181, 153, 129, 115, and 99.

IR (mull) 3129, 3111, 3086, 3063, 3057, 1628, 1602, 1548, 1496, 1322, 1309, 1296, 1143, and 1055 cm$^{-1}$.

NMR ($CDCl_3$) 2.29 (s, 3, $CH_3$), 2.51 (s, 3, $CH_3$), 3.22 (q, 1, $CH_2$), 3.36 (q, 1, $CH_2$), 5.15 (m, 1, CH), 7.18 (s, 1, CH), 7.31 (m, 5, ArH).

EXAMPLE 3

2,3-Dimethyl-α-(3-phenylpropyl)imidazo-[2,1-b]thiazole-5-methanol (Formula A-9) Refer to Chart A.

Magnesium (0.29 g) in ether was treated with 1-bromo-3-phenylpropane (2.38 g) and reacted for 5 hours. Solid 2,3-Dimethylimidazo[2,1-b]thiazole-5-carboxaldehyde (Formula A-6) (0.72 g) was added and the viscous mixture was reacted for 1.5 hours. The thick suspension was diluted with ether and poured into cold 5% ammonium chloride solution. The mixture was extracted with ethyl acetate, the extract was dried and evaporated to a semi-crystalline residue (1.6 g). The residue, containing unreacted 2,3-Dimethylimidazo[2,1-b]thiazole-5-carboxaldehyde (Formula A-6), was triturated with ether, filtered and the filter cake (0.50 g) was recrystallized from acetonitrile to yield pure 2,3-Dimethyl-α-(3-phenylpropyl)imidazo-[2,1-b]thiazole-5-methanol (Formula A-9) (0.38 g), m.p. 167–169°.

Anal. Calc'd for $C_{17}H_{20}N_2OS$: C, 67.97; H, 6.71; N, 9.32; S, 10.67. Found: C, 67.86; H, 6.76; N, 9.25; S, 10.53.

MS m/z 300 (M$^+$), 283, 273, 255, 241, 181, 153, and 91

IR (mull) 3262, 3116, 3080, 3062, 3047, 3023, 1602, 1493, 1391, 1325, 1316, 1288, 1270, 1241, 1147, 1139, and 1079 cm$^{-1}$.

NMR ($CDCl_3$) 1.67–2.10 (m, 4, $CH_2$), 2.29 (s, 3, $CH_3$), 2.50 (s, 3, $CH_3$) 2.70 (m, 2, $CH_2$), 4.87 (m, 1, CH), 6.97 (s, 1, CH), 7.1–7.35 (m, 5, ArH).

EXAMPLE 4

2,3-Dimethyl-α-Di(2-phenylethyl)imidazo-[2,1-b]thiazole-5-methanol (Formula A-10) Refer to Chart A.

Magnesium (0.313 g) in ether (25 mL) was treated with 2-(bromoethyl)benzene (2.37 g) and reacted with 2.25 hours. Solid 2,3-Dimethylimidazo[2,1-b]thiazole-5-carboxylic acid ethyl ester (Formula A-4) (0.29 g) was added and the thick suspension was vigorously stirred for 4.5 hours. The mixture was quenched into 5% ammonium chloride solution and product was extracted into ethyl acetate. Drying and evaporation of solvent gave a semi-crystalline residue (0.88 g). The residue was triturated with ether, filtered, and the filter cake (0.34 g) was crystallized from methylene chloride-isopropanol solution to provide pure 2,3-Dimethyl-α-Di(2-phenylethyl)imidazo-[2,1-b]thiazole-5-methanol (Formula A-10) (0.25 g), m.p. 145–146°.

Anal. Calc'd for $C_{24}H_{26}N_2OS$: C, 73.81; H, 6.71; N, 7.17; S, 8.21. Found: C, 73.76; H, 6.75; N, 7.08; S, 8.26.

MS m/z 390 (M$^+$), 372, 285, 267, 241, 194, 193, 179, 165, 153, and 91.

IR (mull) 3145, 3134, 3084, 3064, 3057, 3037, 3025, 1601, 1532, 1494, 1310, 1289, 1177, 1166 and 1057 cm$^{-1}$.

NMR ($CDCl_3$) δ 2.25–2.43 (m, 7, $CH_3$, $CH_2$), 2.50–2.62 (m, 3, $CH_2$, OH), 2.65 (s, 1, $CH_3$), 2.7–2.9 (m, 2, $CH_2$), 7.09 (s, 1, CH), 7.12–7.32 (m, 10, ArH).

PREPARATION 6

2-Phenyl-E-ethenyl)-3-methylimidazo[2,1-b]thiazol-5-yl methanone (Formula B-2) Refer to Chart B.

A solution of 1-(3-methylimidazo[2,1-b]thiazol-5-yl) ethanone (synthesized by the generic procedure described above were $R_{14}=CH_3$ modified according to Fajgeli et al., *Heterocycles*, 1986, 24, 379 and Copar et al., *J. Heterocyclic Chem.*, 1993, 30, 1577. (7.21 g) in THF (100 mL) was treated with benzaldehyde (6.99 g) and sodium methoxide (1.08 g) and reacted for 3 hours. The solution was diluted with ice water and the precipitated 2-Phenyl-E-ethenyl)-3-methylimidazo[2,1-b]thiazol-5-yl methanone (Formula B-2) (10.8 g) was filtered. An aliquot was recrystallized from isopropanol as an analytical sample, m.p. 150–152°.

Anal. Calc'd for $C_{15}H_{12}N_2OS$; C, 67.14; H, 4.51; N, 10.44; S, 11.95. Found: C, 66.90; H, 4.60; N, 10.40; S, 11.89.

MS m/z 268 (M$^+$), 267, 240, 239, 191, 177, 165, 138 and 103.

IR (mull) 3093, 1647, 1591, 1574, 1447, 1421, 1363, 1300, 1193, and 1034 cm$^{-1}$.

NMR ($CDCl_3$) δ 2.80 (s, 3, $CH_3$), 6.55 (s, 1, CH), 7.30 (d, J=16 Hz, 1, CH), 7.42 (m, 3, ArH), 7.62 (m, 2, ARH), 7.78 (d, J=15 Hz, 1, CH), 8.15 (s, 1, CH).

EXAMPLE 5

α,3-Dimethyl-α-(E-2-phenyl-E-ethenyl)imidazo[2,1-b]thiazole-5-methanol (Formula B-4) and 2-phenylpropyl-3-methylimidazo[2,1-b]thiazol-5-yl methanone (Formula B-3) Refer to Chart B.

A suspension 2-Phenyl-E-ethenyl)-3-methylimidazo[2,1-b]thiazole-5-yl methanone (Formula B-2) (1.07 g) in THF (26 mL) at −78° was treated with 3M ethereal methyl magnesium bromide (1.47 mL) and the mixture was reacted at −15 to −20° for 18 hours. Additional reagent (0.30 mL) was added and reacted at 25° for 1.5 hours. The reaction mixture was poured into cold 5% $NH_4Cl$ solution and products were extracted into ethyl acetate. The residue from drying and evaporation of solvent deposited α,3-Dimethyl-α-(E-2-phenyl-E-ethenyl)imidazo[2,1-b]thiazole-5-methanol (Formula B-4) (0.22 g) from ether solution. The filtrate residue (1.0 g) was fractionated on silica gel (100 g); 85:15 hexane:ethyl acetate eluted 2-phenylpropyl-3-methylimidazo[2,1-b]thiazol-5-yl methanone (Formula B-3) (0.44 mg), 1:1 ethyl acetate:hexane eluted α,3-Dimethyl-α-(E-2-phenyl-E-ethenyl)imidazo[2,1-b]thiazol-5-methanol (Formula B-4) (0.41 g), m.p. 145–147° after ethyl acetate hexane crystallization.

Formula B

Anal. Calc'd for $C_{16}H_{16}N_2OS$: C, 67.58; H, 5.67; N, 9.85; S, 11.28, Found: C, 67.21; H, 5.68; N, 9.79; S, 11.10.

MS m/z 284 ($M^+$), 241, 152, 151, 139, 138 and 131.

IR (mull) 3340, 3245, 1448, 1367, 1271, 1178, 1159, 1117 and 1093 $cm^{-1}$.

NMR ($CDCl_3$) 1.91 (s, 3, $CH_3$), 2.3 (b, 1, OH), 2.57 (s, 3, $CH_3$), 6.24 (d, J=Hz, 1, CH), 6.30 (s, 1, CH), 6.54 (d, J=16 Hz, 1, CH), 7.32 (m, 5, CH, ArH).

Formula B-3

NMR ($CDCl_3$) δ 1.34 (d, J=7 Hz, 3, $CH_3$), 2.67 (s, 3, $CH_3$), 3.06 (m, 2, $CH_2$), 3.47 (m, 1, CH), 6.48 (s, 1, CH), 7.3 (m, 5, ArH), 7.97 (s, 1, CH).

EXAMPLE 6

3-Methyl-α-(2-phenylpropyl)imidazo[2,1-b]thiazole-5-methanol (Formula B-5) Refer to Chart B.

A solution of 2-phenylpropyl-3-methylimidazo[2,1-b]thiazol-5-yl methanone (Formula B-3) (0.28 g) in ethanol (20 mL) was treated with $NaBH_4$ (41.7 mg) and reacted for 48 hours. Solvent was evaporated and the residue was treated with water and the precipitated product was extracted into ethyl acetate. Drying and evaporation of the extract gave crude 3-Methyl-α-(2-phenylpropyl)imidazo[2,1-b]thiazole-5-methanol (Formula B-5) (0.25 g) which deposited pure 3-Methyl-α-(2-phenylpropyl)imidazo[2,1-b]thiazole-5-methanol (Formula B-5) (0.23 g), m.p. 135–136°, from isopropanol solution.

Anal. Calc'd for $C_{16}H_{18}N_2OS$: C, 67.10; H, 6.34; N, 9.78; S, 11.20. Found: C, 66.71; H, 5.97; N, 9.30; S, 10.75.

MS m/z 286 ($M^+$), 181, 169, 168, 167, 165, and 105.

IR (mull) 3283, 3030, 1493, 1428, 1366, 1302, 1254, 1150, 1094, 1083, and 1035 $cm^{-1}$.

NMR ($CDCl_3$) δ 1.36 (d, J=7 Hz, 3, $CH_3$), 1.8 (b, 1, OH), 2.21 (m, 2, $CH_2$), 2.38 (s, 3, $CH_3$), 3.10 (m, 1, CH), 4.65 (m, 1, CH), 6.30 (s, 1, CH), 7.10–7.40 (m, 6, CH, ArH).

PREPARATION 7

(2-Phenylethyl)-3-methylimidazo[2,1-b]thiazol-5-yl methanone (Formula B-6) Refer to Chart B.

A solution of 2-Phenyl-E-ethenyl)-3-methylimidazo[2,1-b]thiazol-5-methanone (Formula B-2) (0.50 g) in ethylacetate (70 mL) was treated with platinum oxide (0.50 g) at 25° and reduced under 40 psi hydrogen pressure. After 5 days the catalyst was filtered and the filtrate was concentrated to an orange oil (450 g). The oil was loaded onto a silica column (45 gms) and produce was eluted with 1:3 ethylacetate:hexane to yield pure (2-Phenylethyl)-3-methylimidazo[2,1-]-thiazol-5-yl methanone (Formula B-6) (0.13 g), m.p. 74–76°, after recrystallization from isopropanol.

Anal. Calc'd for $C_{15}H_{14}N_2OS$; C, 66.64; H, 5.22; N, 10.36; S, 11.86. Found: C, 66.52; H, 5.24; N, 10.34; S, 11.92.

MS m/z 271, 270 ($M^+$), 193, 165, 139, 138, 104, 91, 72, 53, 38

IR (mull) 1661, 1507, 1497, 1429, 1361, 1302, 1184, 1165, 941, 920, 754, 747, 696 $CM^{-1}$.

NMR ($CDCl_3$) δ 2.74 (s, 3, $CH_3$), 3.09 (m, 2, $CH_2$), 3.13 (m, 2, $CH_2$), 6.51 (s, 1, CH), 7.24 (m, 5, ArH), 7.99 (s, 1, CH).

EXAMPLE 7

α,3-Dimethyl-α-(2-phenylethyl)imidazo[2,1-b]thiazole-5-methanol (Formula B-7) Refer to Chart B.

A solution of (2-Phenylethyl)-3-methylimidazo[2,1-b]thiazol-5-yl methanone (Formula B-6) (0.40 g) in THF (6 mL) was treated with 3M ethereal methyl magnesium bromide (0.6 mL) and reacted for 18 hours. The suspension was treated with 5% $NH_4Cl$ solution and precipitated α,3-Dimethyl-α-(2-phenylethyl)imidazo[2,1-b]thiazole-5-methanol (Formula B-7) was extracted into ethyl acetate. The extract was dried and evaporated to a viscous residue which deposited α,3-Dimethyl-α-(2-phenylethyl)imidazo[2,1-b]thiazole-5-methanol (Formula B-7) (0.25 g) by ether trituration. Crystallization of the filter cake from ethyl acetate gave pure α,3-Dimethyl-α-(2-phenylethyl)imidazo[2,1-b]thiazole-5-methanol (Formula B-7) (0.13 g), m.p. 131–133°.

Anal. Calc'd for $C_{16}H_{18}N_2OS$: C, 67.10; H, 6.34; N, 9.78; S, 11.20. Found: C, 66.44; H, 6.35; N, 9.56; S, 11.08.

MS m/z 286 ($M^+$), 271, 183, 182, 181, 165, 139, and 91.

IR (mull) 3169, 3132, 3116, 3106, 3090, 3083, 3062, 3040, 1683, 1655, 1605, 1589, 1582, 1499, 1413, 1374, 1355, 1298, 1276, 1266, 1189, and 1161 $cm^{-1}$.

NMR (DMSO) δ 1.7, (s, 3, $CH_3$), 3.28 (m, 2, $CH_2$), 2.55 (m, 1, $CH_2$), 2.72 (s, 3, $CH_3$), 2.80 (m, 1, $CH_2$), 6.48 (s, 1CH), 7.05–7.35 (m, 5, ArH), 7.58 (s, 1, CH).

EXAMPLE 8

3-Methyl-α-(2-phenylethyl)imidazo[2,1-b]thiazole-5-methanol (Formula B-8) Refer to Chart B.

A solution of (2-Phenylethyl)-3-methylimidazo[2,1-b]thiazol-5-yl methanone (Formula B-6) (0.40 g) in ethanol (5.0 mL) was treated with a solution of $NaBH_4$ (0.05 g) in ethanol (5 mL) and reacted for 18 hours. The solvent was removed in vacuo and the residue was treated with 5% acetic acid solution. Precipitated 3-Methyl-α-(2-phenylethyl)imidazo[2,1-b]thiazole-5-methanol (Formula B-8) (0.38 g) was filtered and recrystallized from isopropanol solution to provide pure 3-Methyl-α-(2-phenylethyl)imidazo[2,1-b]thiazole-5-methanol (Formula B-8) (0.35 g), m.p. 144–145°.

Anal. Calc'd for $C_{15}H_{16}N_2OS$: C, 66.15; H, 5.92; N, 10.28; S, 11.77. Found: C, 66.07; H, 5.88; N, 10.23; S, 11.74.

MS m/z 272 ($M^+$), 168, 167, 139, and 77.

IR (mull) 3236, 3182, 3134, 3116, 1499, 1429, 1160, 1149, 1051, and 915 $cm^{-1}$.

NMR ($CDCl_3$) δ 2.24 (m, 2, $CH_2$), 2.55 (s, 3, $CH_3$), 2.80 (m, 2, $CH_2$), 3.20 (b, 1, OH), 4.88 (t, 1, CH), 6.31 (s, 1, CH), 7.00 (s, 1, CH), 7.23 (m, 5, ArH).

PREPARATION 8

2-(4-Bromophenyl)-E-ethenylimidazo[2,1-b]thiazol-5-yl methanone (Formula B-9) Refer to Chart B.

A solution of 1-(3-methylimidazo[2,1-b]thiazol-5-yl) ethanone (Formula B-1) (1.8 g) in THF (25 mL) was treated with 4-bromobenzaldehyde (3.05 mL) and sodium methoxide (0.27 g) at 25°. Within 5 minutes a heavy precipitate formed and additional THF (65 mL) was added to maintain fluididy. After 20 minutes the reaction was concentrated in vacuo and the concentrate was diluted with water and precipitated 2-(4-Bromophenyl)-E-ethenylimidazo[2,1-b]thiazole-5-yl methanone (Formula B-9) (2.9 g) was filtered. The precipitate was recrystallized from ethanol to yield pure 2-(4-Bromophenyl)-E-ethenylimidazo[2,1-b]thiazol-5-yl methanone (Formula B-9) (2.8 g, 81%), m.p. 213–215°.

Anal. Calc'd for $C_{15}H_{11}BrN_2OS$: C, 51.89; H, 3.19; Br, 23.01; N, 8.07; S, 9.24. Found: C, 51.90; H, 3.12; Br, 22.86; N, 8.11; S, 9.19.

Ms. m/z 348, 346 ($M^+$), 267, 177, 165, 138, 199, 102, 72.

IR (mull) 3121, 1662, 1610, 1513, 1486, 1435, 1428, 1300, 1204, 1198, 1035, 1008, 979, 960, 819, 810, 739 $cm^{-1}$.

NMR ($CDCl_3$) δ 2.79 (s, 3, $CH_3$), 6.56 (s, 1, CH), 7.28 (d, J=16 Hz, 2, CH), 7.50 (d, J=8 Hz, 2, ArH), 7.56 (d, J=8 Hz, 2, ArH), 7.70 (d, J=16 Hz, 1, CH), 8.15 (S, 1, CH).

PREPARATION 9

2-(4-Bromophenylethyl)-3-methylimidazo[2,1-b]thiazol-5-yl methanone (Formula B-10) Refer to Chart B.

A solution of 2-(4-Bromophenyl)-E-ethenylimidazo[2,1-b]thiazol-5-yl methanone (Formula B-9) (1.04 g) in toluene (160 mL) was treated with a solution prepared by dissolving $Na_2S_2O_4$ (14.4 g) in water (220 mL), adding sodium bicarbonate (15.6 g) and Aliquot®336 (0.41 mL). The vigorously stirred suspension was heated at 100° for 85 hours, diluted with ethyl acetate and partitioned. The extract was washed with saline solutions, dried and evaporated to a viscous residue. The residue was chromatographed on silica gel and product was eluted with 4:1 hexane:ethyl acetate to provide 2-(4-Bromophenylethyl)-3-methylimidazo[2,1-b]thiazol-5-yl methanone (Formula B-10) (0.220 g). An aliquot was crystallized from isopropanol to yield pure 2-(4-Bromophenylethyl)-3-methylimidazo[2,1-b]thiazol-5-yl methanone (Formula B-10), m.p, 113–115°.

MS m/z 350, 348 ($M^+$), 333, 331, 319, 317, 268, 239, 193, 191, 185, 184, 183, 182, 165, 139, and 138.

IR (mull) 1662, 1506, 1487, 1425, 1402, 1362, 1352, 1304, 1270, 1188, 1182, 1170, 1072, 1008 and 939 $cm^{-1}$.

NMR ($CDCl_3$) δ 2.73 (s, 3, $CH_3$), 3.04 (m, 2, $CH_2$), 3.10 (m, 2, $CH_2$), 6.51 (s, 1, CH), 7.11 (d, J=8 Hz, 2, ArH), 7.40 (d, J=8 Hz, 2, ArH), 7.99 (s, 1, CH).

EXAMPLE 9

3-Methyl-α-(4-bromophenylethyl)imidazo[2,1-b]thiazole-5-methanol (Formula B-11) Refer to Chart B.

A solution of 2-(4-Bromophenylethyl)-3-methylimidazo[2,1-b]thiazol-5-yl methanone (Formula B-10) (0.2 g) in ethanol (5 mL) was treated with a solution of $NaBH_4$ (65 mg) in ethanol (5 mL) and reacted for 3 hours. The solution was evaporated, the residue was diluted with water and precipitated 3-Methyl-α-(4-bromophenylethyl)imidazo[2,1-b]thiazole-5-methanol (Formula B-11) (0.20 g) was filtered. Crystallization from acetonitrile gave pure 3-Methyl-α-(4-bromophenylethyl)imidazo[2,1-b]thiazole-5-methanol (Formula B-11), m.p. 175–178°.

Anal. Calc'd for $C_{15}H_{15}N_2OS$: C, 51.29; H, 4.30; Br, 22.75; N, 7.98; S, 9.13. Found: C, 51.41; H, 4.31; Br, 22.44; N, 8.01; S, 9.14.

MS m/z 352, 350 ($M^+$), 169, 168, 167, 139, 109, and 90.

IR (mull) 3244, 3184, 3078, 1665, 1647, 1571, 1536, 1451, 1490, 1448, 1430, 1308, 1288, 1178, 1141, 1075, and 1044 $cm^{-1}$.

NMR ($CDCl_3$) δ 2.27 (m, 2, $CH_2$), 2.58 (s, 3, $CH_3$), 2.80 (m, 2, $CH_2$), 4.88 (t, 1, CH), 6.38 (s, 1, CH), 7.09 (d, J=8 Hz, 2, ArH), 7.15 (s, 1, CH), 7.41 (d, J=8 Hz, 2, ArH).

PREPARATION 10

N'-(4-Methyl-2-thiazolyl)-N,N-dimethyl-methanimidamide (Formula C-2) Refer to Chart C.

A solution 2-amino-4-methylthiazole (Formula C-1)(11.4 g) in toluene (100 ml) at 25° was treated with dimethylformamide dimethyl acetal (15.9 mL, 200 mmol), dropwise over five minutes. The mixture was heated to reflux temperature for 22 hours. The reaction was cooled to 25° and the solvent evaporated to an orange oil (17 g). The oil was triturated with hexane to yield yellow crystals. Recrystallization from warm hexane gave N'-(4-Methyl-2-thiazolyl)-N,N-dimethyl-methanimidamide (Formula C-2) (16.9 g, 99.6%), m.p. 54–56°.

Anal. Calc'd for $C_7H_{11}N_3S$: C, 49.68; H, 6.55; N, 24.83; S, 18.94. Found: C, 49.71; H, 6.64; N, 24.52; S, 18.70.

MS m/z 169 ($M^+$), 154, 136, 127, 99, 98, 71, 44, and 27.

IR (mull) 3081, 1632, 1503, 1475, 1431, 1414, 1398, 1354, 1302, 1265, 1133, and 1117 $cm^{-1}$.

NMR ($CDCl_3$) δ 2.30 (s, 3, $CH_3$), 3.06 (s, 3, $CH_3$), 3.08 (s, 3, $CH_3$), 6.34 (s, 1, CH), 8.18 (s, 1, CH).

PREPARATION 11

2-[[(Dimethylamino)methylene]amino]-3-)2-ethoxy-2-oxoethyl)-4-methyl-thiazolium bromide (Formula C-3) (Refer to Chart C).

Solid N'-(4-Methyl-2-thiazolyl)-N,N-dimethyl-methanimidamide (Formula C-2) (5.0 g) was added in portions to vigorously stirred ethyl bromoacetate (16 mL). Precipitation of 2-[[(Dimethylamino)methylene]amino]-3-)2-ethoxy-2-oxoethyl)-4-methyl-thiazolium bromide (Formula C-3) was well advanced after 2 hours and toluene (10 mL) was added to improve fluidity. After 24 hours the precipitated 2-[[(Dimethylamino)methylene]amino]-3-)2-ethoxy-2-oxoethyl)-4-methyl-thiazolium bromide (Formula C-3) (9.8 g) was filtered and crystallized from acetonitrile to yield pure 2-[[(Dimethylamino)methylene]amino]-3-)2-ethoxy-2-oxoethyl)-4-methyl-thiazolium bromide (Formula C-3), 8.32 g, m.p. 188–189°. Heating N'-(4-Methyl-2-thiazolyl)-N,N-dimethyl-methanimidamide (Formula C-2) in toluene solution for 4.5 hours with a 20% molar excess of ethyl bromoacetate also gave 2-[[(Dimethylamino) methylene]amino]-3-(2-ethoxy-2-oxoethyl)-4-methyl-thiazolium bromide (Formula C-3) (76%) cleanly.

Anal. Calc'd for $C_{11}H_{18}BrN_3O_2S$: C, 39.29; H, 5.39; Br, 23.77; N, 12.50; S 9.53. Found: C, 39.34; H, 5.36; Br, 23.78; N, 12.52; S, 9.48.

MS (FAB) m/z 256 ($M^+$-Br).

IR (mull) 3028, 1757, 1645, 1593, 1531, 1491, 1481, 1419, 1402, 1393, 1218, and 1138 $cm^{-1}$.

NMR ($CDCl_3$) δ 1.30 (t, J=7 Hz, 3, $CH_3$), 2.41 (s, 3, $CH_3$), 3.23 (s, 3, $CH_3$), 3.60 (s, 3, $CH_3$), 4.25 (q, J=7 Hz, 2, $CH_2$), 4.98 (s, 2, $CH_2$), 6.86 (s, 1, CH), 9.32 (s, 1, CH).

PREPARATION 12

3-Methylimidazo[2,1-b]thiazole-5-carboxylic acid ethyl ester (Formula C-4) Refer to Chart C.

A solution of 2-[[(Dimethylamino)methylene]amino]-3-)2-ethoxy-2-oxoethyl)-4-methyl-thiazolium bromide (Formula C-3) (6.5 g) in DMF (20 mL) was treated with DBU (5.78 g) and reacted for 24 hours. The reaction solution was diluted with water and precipitated 3-Methylimidazo[2,1-b]thiazole-5-carboxylic acid ethyl ester (Formula C-4) (2.1 g) was filtered. Crystallization from hexane gave pure 3-Methylimidazo[2,1-b]thiazole-5-carboxylic acid ethyl ester (Formula C-4), m.p. 45°.

Anal. Calc'd for $C_9H_{10}N_2O_2S$: C, 51.41; H, 4.79; N, 13.33; S, 15.25. Found: C, 51.32; H, 4.78; N, 13.23; S, 15.14.

MS m/z 210 ($M^+$), 182, 181, 165, 164, 138, 136, 125, and 93.

IR (mull) 1723, 1507, 1440, 1434, 1425, 1353, 1318, 1207, 1195, 1140, 1083, 1074 and 1070 $cm^{-1}$.

NMR ($CDCl_3$) 1.38 (t, J=7 Hz, 3, $CH_3$), 2.73 (s, 3, $CH_3$), 4.32 (q, J=7 Hz, 2, $CH_2$), 6.50 (s, 1, CH), 7.98 (s, 1, CH)

PREPARATION 13

3-Methylimidazo[2,1-b]thiazole-5-Methanol (FIG. C-5) Refer to Chart C.

A solution of 3-Methylimidazo[2,1-b]thiazole-5-carboxylic acid ethyl ester (Formula C-4) (1.93 g, 9.2 mmol) in dry THF (20 ml) at 0° was treated with $LiAlH_4$ (12.3 mmols, 0.47 gms) and reacted at 25° for 2 hours. The reaction was quenched by serial additions of 2% aqueous.. THF (24 mL), 15% NAOH (0.47 mL), and 2% aqueous THF (1.5 mL). The suspension was filtered and the filtrate was concentrated to a white solid (1.48 gm). The solid was recrystallized from isopropanol to yield pure 3-Methylimidazo[2,1-b]thiazole-5-Methanol (FIG. C-5) (1.18 g), m.p. 161–162°.

Anal. Calc'd for $C_7H_8N_2OS$: C, 49.98; H, 4.79; N, 16.65; S, 19.06. Found: C, 49.87; H, 4.80; N, 16.48; S, 18.91.

MS m/z 168 ($M^+$), 167, 152, 151, 150, 139, 72, 71, 45.

IR (mull) 3140, 3123, 3098, 2749, 1446, 1431, 1390, 1340, 1314, 1144, 1029, 1023, 1016, 828, 821, 754, 689, 650 $cm^{-1}$.

NMR (DMSO, $D_6$) δ 3.33 (S, 3, $CH_3$), 4.70 (d, J=5 Hz, 2, $CH_2$), 5.16 (t, J=5 Hz, 1, OH), 6.54 (s, 1, CH), 7.11 (s, 1, CH).

PREPARATION 14

3-Methylimidazo[2,1-b]thiazole-5-carboxaldehyde (FIG. C-6) Refer to Chart C.

A solution of 3-Methylimidazo[2,1-b]thiazole-5-methanol (FIG. C-5) (0.9 g) in DMF (10 mL) was diluted with toluene (200 mL), treated with $MnO_2$ (3.0), and azeotropically distilled for 1.5 hours. The suspension was filtered and the filtrate was concentrated to 10 mL. The concentrate was diluted with ice water and the precipitated 3-Methylimidazo[2,1-b]thiazole-5-carboxaldehyde (FIG. C-6) (0.665 g) was filtered. An aliquot (225 mg) was recrystallized from ethyl acetate-hexane to yield pure 3-Methylimidazo[2,1-b]thiazole-5-carboxaldehyde (FIG. C-6) (202 mg), m.p. 163–165°.

Anal. Calc'd for $C_7H_6N_2OS$; C, 50.59; H, 3.64; N, 16.85; S, 19.29. Found: C, 50.63; H, 3.64; N, 16.70; S, 18.95.

MS m/z 166 ($M^+$), 165, 137, 93, 72, 71, 70, 45, 38.

IR (mull) 3104, 3053, 3016, 1677, 1671, 1451, 1394, 1353, 1323, 1309, 1262, 1174, 833, 798 $cm^{-1}$.

NMR ($CDCl_3$) δ 2.79 (s, 3, $CH_3$), 6.56 (s, 1, CH), 8.02 (s, 1, CH), 9.61 (s, 1, CH).

EXAMPLE 10

3-Methyl-α-(4-phenylbutyl)imidazo-[2,1-b]thiazole-5-methanol (FIG. C-7) Refer to Chart C.

Magnesium (0.15 g) in ether (15 mL) was treated with 1-bromo-4-phenylbutane (prepared by the procedure described in Kamijo et al., Chem. Phar. Bull., 1983, 31, 4189) (1.50 g) at 0° and the mixture was reacted at 25° for 2.5 hours. The suspension was cooled to 0°, solid 3-Methylimidazo[2,1-b]thiazole-5-carboxaldehyde (FIG. C-6) (0.332 g) was added and the mixture was reacted at 25° for 3 hours. The solution was decanted into 5% $NH_4Cl$ solution and extracted with ethyl acetate. The extract was dried, evaporated and the residue (0.55 g) was crystallized from acetonitrile solution to yield pure 3-Methyl-α-(4-phenylbutyl)imidazo-[2,1-b]thiazole-5-methanol (FIG. C-7) (0.39 g), m.p. 120–121°.

Anal. Calc'd for $C_{17}H_{20}N_2OS$: C, 67.97; H, 6.71; N, 9.32; S, 10.67. Found: C, 67.67; H, 6.68; N, 9.28; S, 10.56.

MS m/z 300 ($M^+$), 169, 168, 167, 139, 138, 114, and 91.

IR (mull) 3161, 3145, 3132, 3082, 3063, 3031, 3019, 1495, 1450, 1309, 1260, 1148, 1070, and 956 $cm^{-1}$.

NMR ($CDCl_3$) δ 1.71 (m, 3, $CH_3$), 2.00 (m, 3, $CH_2$), 2.63 (m, 5, $CH_2$) 4.9 (t, 1, CH), 6.36 (s, 1, CH), 7.11 (s, 1, CH), 7.20 (m, 5, ArH).

PREPARATION 15

2,3-Dimethyl-(2-phenyl-E-ethenyl)imidazo[2,1-b]thiazol-5-yl methanone (FIG. D-2) Refer to Chart D.

A solution of 1-(2,3-dimethylimidazo[2,1-b]thiazole-5-yl ethanone (See procedures from Preparation 6) (Formula D-1) (0.87 g) in THF (25 mL) was treated with benzaldehyde (0.52 mL) and sodium methoxide (0.11 g). After 18 hours trace 1-(2,3-dimethylimidazo[2,1-b]thiazol-5-yl ethanone remained and additional benzaldehyde (0.2 mL) was added. After an additional 2.5 hours the reaction was diluted with ice water and precipitated 2,3-Dimethyl-(2-phenyl-E-ethenyl)imidazo[2,1-b]thiazol-5-yl methanone (FIG. D-2) (1.03 g) was filtered. Crystallization from isopropanol solution gave pure 2,3-Dimethyl-(2-phenyl-E-ethenyl)imidazo[2,1-b]thiazol-5-yl methanone (FIG. D-2), m.p. 189–190°.

Anal. Calc'd for $C_{16}H_{14}N_2OS$: C, 68.06; H, 5.00; N, 9.92; S, 11.36. Found: C, 68.05; H, 5.06; N, 9.85, S, 11.26.

MS m/z 282 ($M^+$), 265, 254, 253, 241, 239, 205, 191, 179, 154, 153, 152, 127, and 103.

IR (mull) 3096, 1658, 1601, 1577, 1506, 1450, 1421, 1360, 1308, 1296, 1279, 1200, 1189, 1179, 1034, and 1025 $cm^{-1}$.

NMR ($CDCl_3$) δ 2.39 (s, 3, $CH_3$), 2.68 (s, 3, $CH_3$), 7.30 (d, J=16 Hz, 1, CH), 7.42 (m, 3, ArH), 7.62 (m, 2, ArH), 7.79 (d, J=16 Hz, 1, CH), 8.09 (s, 1, CH).

EXAMPLE 11

2,3-Dimethyl-α-(2-phenylethyl)imidazo[2,1-b]thiazole-5-methanol (FIG. D-4) Refer to Chart D.

A solution of 2,3-Dimethyl-(2-phenyl-E-ethenyl)imidazo[2,1-b]thiazol-5-yl methanone (FIG. D-2) (0.3 g) in 5:3 ethylacetate:ethanol solution (50 mL) was treated with $PtO_2$ (0.15 g) and reduced at 45 psi $H_2$ pressure for 24 hours. The catalyst was filtered, the reaction was recharged with $PtO_2$ (0.15 g) and reduced for an additional 24 hours. Catalyst was filtered and solvents evaporated to yield a viscous residue. Ether trituration of the residue provide 0.15 g of a 2:1 mixture of starting material and (2-phenylethyl-2,3-dimethylimidazo[2,1-b]thiazol-5-yl methanone (Formula D-3). The ether filtrate residue (0.15 g) was rich in (2-phenylethyl-2,3-dimethylimidazo[2,1-b]thiazol-5-yl methanone (Formula D-3) and was reduced to 2,3-Dimethyl-α-(2-phenylethyl)imidazo[2,1-b]thiazole-5-methanol (FIG. D-4) in ethanol (10 ml) solution with NaBH$_4$ (0.15 g) during 30 minutes. The residue from evaporation of ethanol was treated with water and the sticky precipitate was extracted into ethyl acetate. Drying and evaporation of the extract gave crude 2,3-Dimethyl-α-(2-phenylethyl)imidazo[2,1-b]thiazole-5-methanol (FIG. D-4) which was purified on silica gel (100 g) with 1:1 ethyl acetate:hexane. Crystallization of the eluted product from ethyl acetate gave pure 2,3-Dimethyl-α-(2-phenylethyl)imidazo[2,1-b]thiazole-5-methanol (FIG. D-4), m.p. 153–154°.

Anal. Calc'd for $C_{16}H_{18}N_2OS$: C, 67.10; H, 6.34; N, 9.78; S, 11.19. Found: C, 67.17; H, 6.30; N, 9.79: S, 11.10.

MS m/z 286 (M$^+$) 259, 242, 203, 181, 165, and 153.

IR (mull) 3245, 1640, 1603, 1487, 1449, 1393, 1328, 1244, 1138, 1063, and 1052 cm$^{-1}$.

NMR (CDCl$_3$) δ 2.30 (m, 5, CH$_3$, CH$_2$), 2.47 (s, 3, CH$_3$), 2.75–3.0 (m, 2, CH$_2$), 4.90 (t, 1, CH), 7.14 (s, 1, CH), 7.18–7.35 (m, 5, ArH).

EXAMPLE 12

2,3-Dimethyl-α-(2-phenylethenyl)imidazo[2,1-b]thiazole-5-methanol (FIG. D-5) Refer to Chart D.

A solution of 2,3-Dimethyl-α-(2-phenyl-E-ethenyl)imidazo[2,1-b]thiazole-5-methanone (FIG. 2-D) (0.34 g) in 1:1 ethanol:THF (40 mL) was treated with a solution of NaBH$_4$ (0.35 g) in ethanol (5 mL). The solution was reacted for 2.5 hours, evaporated in vacuo, and the residue was diluted with water. The precipitated 2,3-Dimethyl-α-(2-phenylethenyl)imidazo[2,1-b]thiazole-5-methanol (FIG. D-5) was extracted into ethyl acetate, the extract was dried and evaporated to a viscous residue. The residue was triturated with ethyl acetate to yield 2,3-Dimethyl-α-(2-phenylethenyl)imidazo[2,1-b]thiazole-5-methanol (FIG. D-5), 0.28 g, m.p. 149–151° after crystallization from acetonitrile.

Anal. Calc'd for $C_{16}H_{16}N_2OS$: C, 67.58; H, 5.67; N, 9.85; S, 11.27. Found: C, 67.20; H, 5.84; N, 9.74; S, 11.05.

MS m/z 284, 267, 255, 207, 181, 179, 165, 153, 152, 139, 128, 115 and 103.

IR (mull) 3240, 3119, 3025, 1651, 1641, 1626, 1603, 1497, 1442, 1426, 1327, 1323, 1308, 1244 and 1140 cm$^{-1}$.

NMR (CDCl$_3$) δ 2.28 (s, 3, CH$_3$), 2.57 (s, 3, CH$_3$), 5.68 (d, J=5 Hz, 1, CH), 6.53 (q, J=5, 16 Hz, 1, CH), 6.75 (d, J=16 Hz, 1, CH), 6.98 (s, 1, CH), 7.17–7.50 (m, 5, ArH).

PREPARATION 16

N'-(5,6-Dihydro-4H-cyclopentathiazolyl)-N,N-dimethylmethimidamide (Formula E-2) Refer to Chart E.

A suspension of 2-aminocyclopentenothiazole (Formula E-1) (8.9 g) in toluene (15 mL) and DMF-dimethylacetal (15.4 mL) was reacted at ambient temperature for 72 hours. The solution was diluted with toluene (150 mL), treated with charcoal, and filtered. The filtrate was evaporated to a crystalline residue (14.7 g) and the residue was triturated with hexane to yield N'-(5,6-Dihydro-4H-cyclopentathiazolyl)-N,N-dimethylmethimidamide (Formula E-2) (11.62 g) as two crops. Crystallization of an aliquot (1.31 g) from ether-hexane solution gave the analytical sample of N'-(5,6-Dihydro-4H-cyclopentathiazolyl)-N,N-dimethylmethimidamide (Formula E-2) (1.07 g), m.p. 124–125°.

Anal. Calcd for $C_9H_{13}N_3S$: C, 55.35; H, 6.72; N, 21.52; S, 16.42. Found: C, 55.45; H, 6.88; N, 21.85; S, 16.49.

MS m/z 195 (M$^+$), 180, 162, 153, 147, 115, and 97.

IR (mull): 1614, 1484, 1448, 1443, 1427, 1401, 1360, 1339 and 1093 cm$^{-1}$.

NMR (CDCl$_3$) δ 2.36 (m, 2, CH$_2$), 2.74 (m, 2, CH$_2$), 2.83 (m, 2, CH$_2$), 3.06 (s, 3, CH$_3$), 3.08 (s, 3, CH$_3$), 8.24 (s, 1, CH).

PREPARATION 17

2-[[(Dimethylamino)methylene]amino]-3-(2-ethoxy-2-oxoethyl)-5,6-dihydro-4H-cyclopentathiazolium bromide (Formula E-3) Refer to Chart E.

A suspension of N'-(5,6-Dihydro-4H-cyclopentathiazolyl)-N,N-dimethylmethimidamide (Formula E-2) (2.40 g) in ethyl bromoacetate (9.0 mL) was dissolved by heating at 45°. Precipitation occurred and additional reagent (5.0 mL) was added. The suspension was reacted for 72 hours, diluted with ethyl acetate, and filtered to yield 2-[[(Dimethylamino)methylene]amino]-3-(2-ethoxy-2-oxoethyl)-5,6-dihydro-4H-cyclopentathiazolium bromide (Formula E-3) (4.38 g). The thiazolium salt was used without further purification.

PREPARATION 18

6,7-Dihydro-5H-cyclopent[d]imidazo[2,1-b]thiazole-3-carboxylic acid ethyl ester (Formula E-4) Refer to Chart E.

A suspension of 2-[[(Dimethylamino)methylene]amino]-3-(2-ethoxy-2-oxoethyl)-5,6-dihydro-4H-cyclopentathiazolium bromide (Formula E-3) (4.0 g) in DMF (20 mL) dissolved on addition of DBU (2.48 mL). The solution was reacted at 25° for 18 hours, poured into cold 10% acetic acid solution, and precipitated 6,7-Dihydro-5H-cyclopent[d]imidazo[2,1-b]thiazole-3-carboxylic acid ethyl ester (Formula E-4) (1.95 g) was filtered. Crystallization of an aliquot from isopropanol gave pure 6,7-Dihydro-5H-cyclopent[d]imidazo[2,1-b]thiazole-3-carboxylic acid ethyl ester (Formula E-4), m.p. 101–102°.

Anal. Calcd for $C_{11}H_{12}N_2O_2S$: C, 55.92; H, 5.12; N, 11.86; S, 13.57. Found: C, 55.85; H, 4.98; N, 11.80; S, 13.57.

MS m/z 236 (M$^+$), 221, 207, 191, 190, 189, 177, 164, 163, 162, 136, 135, 134, and 97.

IR (mull) 1712, 1525, 1509, 1447, 1403, 1393, 1348, 1311, 1287, 1191, 1135, 1111, 1051, and 1023 cm$^{-1}$.

NMR (CDCl$_3$) δ 1.38 (t, J=7 Hz, 3, CH$_3$), 2.51 (m, 2, CH$_2$), 2.93 (m, 2, CH$_2$), 3.27 (m, 2, CH$_2$), 4.33 (q, J=7 Hz, 2, CH$_2$), 7.87 (s, 1, CH).

PREPARATION 19

6,7-Dihydro-5H-cyclopent[d]imidazo[2,1-b]thiazole-3-methanol (FIG. E-5) Refer to Chart E.

A solution of 6,7-Dihydro-5H-cyclopent[d]imidazo[2,1-b]thiazole-3-carboxylic acid ethyl ester (Formula E-4) (5.8 g) in dry THF (125 mL) was treated with LiAlH$_4$ (1.86 g) and reacted for 5.5 hours. After serial quenching with water and 15% sodium hydroxide, the suspension was diluted to 700 mL with chloroform. The filter cake was washed with hot chloroform, the combined filtrate and washes were evaporated to yield pure 6,7-Dihydro-5H-cyclopent[d]imidazo[2,1-b]thiazole-3-methanol (FIG. E-5) (2.67 g).

NMR (DMSO) δ 2.43 (m, 2, $CH_2$), 2.83 (m, 2, $CH_2$), 2.97 (m, 2, $CH_2$), 4.56 (d, J=5 Hz, 2, $CH_2$) 5.21 (t, J=5 Hz, 1, OH), 7.04 (s, 1, CH).

PREPARATION 20

6,7-Dihydro-5H-cyclopent[d]imidazo[2,1-b]thiazole-3-carboxaldehyde (FIG. E-6) Refer to Chart E.

A solution of 6,7-Dihydro-5H-cyclopent[d]imidazo[2,1-b]thiazole-3-methanol (FIG. E-5) (1.5 g) in DMF (20 mL) was diluted with toluene (125 mL), treated with activated manganese dioxide, and the mixture was azeotropically distilled for 60 minutes. The hot solution was filtered and the filtrate was concentrated. The residue was diluted with water and precipitated 6,7-Dihydro-5H-cyclopent[d]imidazo[2,1-b]thiazole-3-carboxaldehyde (FIG. E-6) (1.28 g) was filtered. The carboxaldehyde was used without further purification.

NMR ($CDCl_3$) δ 2.54 (m, 2, $CH_2$), 2.95 (m, 2, $CH_2$), 3.32 (m, 2, $CH_2$), 7.91 (s, 1, CH), 9.62 (s, 1, CH).

EXAMPLE 13

6,7-Dihydro-α-(2-phenylethyl)-5H-cyclopent[d]imidazo[2,1-b]thiazole-3-methanol (FIG. E-7) Refer to Chart E The Grignard reagent generated during 18 hours, from (2-bromoethyl)benzene (2.2 g) an Mg (0.291 g) in THF (70 mL) was treated with solid 6,7-Dihydro-5H-cyclopent[d]imidazo[2,1-b]thiazole-3-carboxaldehyde (FIG. E-6) (0.58 g) and reacted for 1.5 hours. The supernate solution was decanted into cold 5% ammonium chloride solution and precipitated 6,7-Dihydro-α-(2-phenylethyl)-5H-cyclopent[d]imidazo[2,1-b]thiazole-3-methanol (FIG. E-7) (0.80 g) was filtered. Crystallization from acetonitrile solution gave pure 6,7-Dihydro-α-(2-phenylethyl)-5H-cyclopent[d]imidazo[2,1-b]thiazole-3-methanol (FIG. E-7), m.p. 117–118°.

Anal. calcd for $C_{17}H_{18}N_2OS$: C, 68.43; H, 6.08; N, 9.39; S, 10.74. Found: C, 68.21; H, 6.02; N, 9.21; S, 10.53.

MS m/z 298 ($M^+$), 281, 271, 254, 218, 207, 206, 193, 177, 175, 165, 129, and 91.

IR (mull) 3222, 3125, 3088, 3059, 3032, 3029, 1615, 1605, 1497, 1361, 1347, 1333, 1297, 1289, 1281, and 1073.

NMR ($CDCl_3$) δ 2.22 (m, 2, $CH_2$), 2.50 (m, 3, $CH_2$, OH), 2.74–3.10 (m, 6, $CH_2$), 4.80 (t, J=5 Hz, 1, CH), 6.99 (s, 1, CH), 7.29–7.4 (m, 5, ArH).

PREPARATION 21

N'-(4,5,6,7-Tetrahydrobenzothiazolyl)-N,N-dimethylmethimidamide (Formula F-2) Refer to Chart F.

A solution of 2-amino-4,5,6,7-tetrahydrobenzothiazole (Formula F-1) (5.48 g) in toluene (70 mL) was treated with DMF-dimethylacetal (9.43 mL) and heated at reflux temperature for 1.5 hours. The cooled solution was evaporated in vacuo to a crystalline residue. The residue was triturated with hexane to provide N'-(4,5,6,7-Tetrahydrobenzothiazolyl)-N,N-dimethylmethimidamide (Formula F-2) (4.33 g). The filtrate residue (1.9 g) was filtered through silica gel (100 g) with 1:1 ethyl acetate hexane to yield additional N'-(4,5,6,7-Tetrahydrobenzothiazolyl)-N,N-dimethylmethimidamide (Formula F-2) (1.26 g). An aliquot of eluted N'-(4,5,6,7-Tetrahydrobenzothiazolyl)-N,N-dimethylmethimidamide (Formula F-2) was crystallized from ether hexane solution to provide pure N'-(4,5,6,7-tetrahydrobenzothiazolyl)-N,N-dimethylmethimidamide (Formula F-2), m.p. 96–97°.

Anal. Calcd for $C_{10}H_{15}N_3S$: C, 57.38; H, 7.22; N, 20.08; S, 15.32. Found: C, 57.45; H, 7.16; N, 20.08; S, 15.16.

MS m/z 209, 194, 193, 181, 176, 167, 139, 115, and 98.

IR (mull): 1623, 1567, 1510, 1478, 1426, 1411, 1396, 1356, 1347, 1330, 1262, and 1113 $cm^{-1}$.

NMR ($CDCl_3$) δ 1.82 (m, 4, $CH_2$), 2.62 (m, 4, $CH_2$), 3.05 (s, 3, $CH_3$), 3.07 (s, 3, $CH_3$), 8.14 (s, 1, CH).

PREPARATION 22

2-[[(Dimethylamino)methylene]amino]-3-(2-ethoxy-2-oxoethyl)-5,6,7,8-tetrahydrobenzothiazolium bromide (Formula F-3) Refer to Chart F.

A solution of crude N'-(4,5,6,7-Tetrahydrobenzothiazolyl) N,N-dimethylmethimidamide (Formula F-2) (9.38 g) in ethyl bromoacetate (45 mL) produced a thick precipitate of the thiazolium salt (Formula F-3) within 1.5 hours. The suspension was diluted to 500 mL with ethyl acetate, filtered under a $N_2$ atmosphere, and dried in vacuo to yield crude thiazolium salt (Formula F-3) as a hygroscopic solid (14.4 g). The precipitated 2-[[(Dimethylamino)methylene]amino]-3-(2-ethoxy-2-oxoethyl)-5,6,7,8-tetrahydrobenzothiazolium bromide (Formula F-3) was used without additional purification.

PREPARATION 23

5,6,7,8-Tetrahydro-imidazo[2,1-b]benzothiazole-3-carboxylic acid ethyl ester (Formula F-4) Refer to Chart F.

A solution of crude 2-[[(Dimethylamino)methylene] amino]-3-(2-ethoxy-2-oxoethyl)-5,6,7,8-tetrahydrobenzothiazolium bromide (Formula F-3) (14.4 g) in DMF (40 mL) was treated with DBU (8.4 mL) and reacted at ambient temperature for 24 hours. The solution was diluted with ice water and acidified with 1N hydrochloric acid (58 mL). The precipitated 5,6,7,8-Tetrahydro-imidazo[2,1-b]benzothiazole-3-carboxylic acid ethyl ester (Formula F-4) (5.61 g, 63%) was filtered. Crystallization from hexane gave pure 5,6,7,8-Tetrahydro-imidazo[2,1-b]benzothiazole-3-carboxylic acid ethyl ester (Formula F-4), m.p. 75–76°.

Anal. Calcd for $C_{12}H_{14}N_2O_2S$: C, 57.58; H, 5.64; N, 11.19; S, 12.81. Found: C, 57.59; H, 5.82; N, 11.17; S, 12.82.

MS m/z 250 ($M^+$) 222, 221, 205, 204, 203, 178, 176, 175, and 150.

IR (mull) 1720, 1515, 1505, 1451, 1435, 1312, 1292, 1257, 1194, 1174, 1162, 1126, 1112, and 1027 $cm^{-1}$.

NMR ($CDCl_3$) 1.37 (t, J=7 Hz, 3, $CH_3$), 1.91 (m, 4, $CH_2$), 2.74 (m, 2, $CH_2$), 3.17 (m, 2, $CH_2$), 4.31 (q, J=7 Hz, 2, $CH_2$), 7.94 (s, 1, CH).

PREPARATION 24

5,6,7,8-Tetrahydro-imidazo[2,1-b]benzothiazole-3-methanol (Formula F-5) Refer to Chart F.

A suspension of $LiAlH_4$ (2.1 g) in THF (100 mL) was treated with 5,6,7,8-Tetrahydro-imidazo[2,1-b] benzothiazole-3-carboxylic acid ethyl ester (Formula F-4) (5.6 g) and reacted at 25° C. for 5.5 hours. The reaction was quenched by serial additions of water and 15% sodium hydroxide and the mixture was filtered. Evaporation of the filtrate gave 5,6,7,8-Tetrahydro-imidazo[2,1-b] benzothiazole-3-methanol (Formula F-5) (4.11 g), m.p. 182–183° after crystallization from iso-propanol.

Anal. Calcd for $C_{10}H_{12}N_2OS$: C, 57.67; H, 5.81; N, 13.45; S, 15.39. Found: C, 57.44; H, 5.78; N, 13.26; S, 15.36. MS m/z 208 (M$^+$), 191, 190, 189, 179, 163, 132 and 77 IR (mull) 3179, 3095, 1630, 1446, 1442, 1357, 1321, 1312, 1258, and 1026 cm$^{-1}$. NMR (CDCl$_3$) 1.91 (m, 4, CH$_2$), 2.67 (m, 2, CH$_2$), 2.99 (m, 2, CH$_2$), 3.07 (s, 1, OH), 4.73 (s, 2, CH$_2$), 6.99 (s, 1, CH).

PREPARATION 25
5,6,7,8-Tetrahydro-imidazo[2,1-b]thiazole-3-carboxaldehyde (Formula F-6) Refer to Chart F.

A solution of 5,6,7,8-Tetrahydro-imidazo[2,1-b]benzothiazole-3-methanol (Formula F-5) (3.9 g) in hot toluene (270 mL) was treated with activated MnO$_2$ (11.7 g) and azetropically distilled for 1.5 hours. The cooled suspension was filtered and the filtrate was evaporated to yield pure 5,6,7,8-Tetrahydro-imidazo[2,1-b]thiazole-3-carboxaldehyde (Formula F-6) (3.27 g) after hexane trituration. Crystallation of an aliquot from iso-propanol provided an analytical sample, m.p. 108–110°.

Anal. Calcd for C$_{10}$H$_{10}$N$_2$OS: C, 58.25; H, 4.89; N, 13.58; S, 15.54. Found: C, 58.19; H, 4.70; N, 13.79; S, 15.42. MS m/z 206 (M$^+$), 205, 191, 189, 178, 177, 165, 163 and 150. IR (mull) 3096, 1674, 1661, 1445, 1362, 1355, and 1172 cm$^{-1}$. NMR (CDCl$_3$) δ 1.91 (m, 4, CH$_2$), 2.73 (m, 2, CH$_2$), 3.18 (m, 2, CH$_2$), 7.95 (s, 1, CH), 9.56 (s, 1, CH).

EXAMPLE 14
5,6,7,8-Tetrahydro-α-(2-phenylethyl)imidazo[2,1-b]benzothiazole-3-methanol (Formula F-7) Refer to Chart F.

A suspension of Mg (0.31 g) in ether (50 mL) was treated with (2-bromoethyl)benzene (1.32 mL) and reacted for 1.5 hours. Solid 5,6,7,8-Tetrahydro-imidazo [2,1-b]thiazole-3-carboxaldehyde (Formula F-6) (0.66 g) was added, the suspension was diluted with THF (100 mL) and reacted for 18 hours. The supernate solution was decanted into 5% ammonium chloride solution (200 mL) and extracted with ethyl acetate. Drying and evaporation of solvent gave 5,6,7,8-Tetrahydro-α-(2-phenylethyl)imidazo[2,1-b]benzothiazole-3-methanol (Formula F-7) (0.88 g) which deposited pure 5,6,7,8-Tetrahydro-α-(2-phenylethyl)imidazo[2,1-b]benzothiazole-3-methanol (Formula F-7) (0.74 g), m.p. 152–153°, from acetonitrile solution.

Anal. Calcd for C$_{18}$H$_{20}$N$_2$OS: C, 69.20; H, 6.45; N, 8.97; S, 10.26. Found: C, 68.90; H, 6.59; N, 8.94; S, 10.22. MS m/z 312 (M$^+$), 295, 285, 268, 208, 207, 191, 189, 179, 165, 151, 129, and 91. IR (mull) 3185, 3135, 3091, 3067, 3059, 3032, 3025, 1604, 1500, 1446, 1431, 1314, 1274, 1259, 1152, 1076 and 1055 cm$^{-1}$. NMR (CDCl$_3$) δ 1.88 (m, 4, CH$_2$), 2.26 (m, 2, CH$_2$), 245 (b, 1, OH), 2.55–3.0 (m, s, CH$_2$), 3.20 (m, 1, CH$_2$), 4.85 (t, J=5 Hz, 1, CH), 7.06 (s, 1, CH), 7.15–7.40 (m, s, ArH).

PREPARATION 26
N'-(5,6,7,8-Tetrahydro-4H-cycloheptathiazolyl)-N,N-dimethylmethimidamide (Formula G-2) Refer to Chart G.

A solution of 2-aminocycloheptenothiazole (Formula G-1)(13.0 g) in toluene (125 mL) was treated with DMF-dimethylacetal (12.2 mL), heated at reflux temperature for 18 hours, and reacted at 25° for 18 hours. Evaporation in vacuo gave a crystalline mass of N'-(5,6,7,8-Tetrahydro-4H-cycloheptathiazolyl)-N,N-dimethylmethimidamide (Formula G-2) which was recrystallized from cold hexane solution to provide pure N'-(5,6,7,8-Tetrahydro-4H-cycloheptathiazolyl)-N,N-dimethylmethimidamide (Formula G-2) (14.82 g), m.p. 46–48°.

Anal. Calcd for C$_{11}$H$_{17}$N$_3$S: C, 59.16; H, 7.67; N, 18.82; S, 14.36. Found: C, 58.78; H, 7.74; N, 18.96; S, 14.11. MS m/z 223 (M$^+$), 208. 207, 195, 194, 190, 181, 167, 153, 136, 115, and 98. IR (mull): 1617, 1488, 1429, 1340, 1179, 1105 and 1191 cm$^{-1}$. NMR (CDCl$_3$) δ 1.6–1.85 (m, 6, CH$_2$), 2.66 (m, 2, CH$_2$), 2.79 (m, 2, CH$_2$) 3.04 (s, 3, CH$_3$) 3.18 (s, 3, CH$_3$), 8.08 (s, 1, CH).

PREPARATION 27
2-[[(Dimethylamino)methylene]amino]-3-(2-ethoxy-2-oxoethyl)-5,6,7-tetrahydro-4H-cycloheptathiazolium bromide (Formula G-3) Refer to Chart G.

A solution of N'-(5,6,7,8-Tetrahydro-4H-cycloheptathiazol-N,N-dimethylmethimidamide (Formula G-2) (14.8 g) in ethyl bromoacetate (25 mL) was reacted at 25° for 72 hours. The suspension of 2-[[(Dimethylamino)methylene]amino]-3-(2-ethoxy-2-oxoethyl)-5,6,7-tetrahydro-4H-cycloheptathiazolium bromide (Formula G-3) was diluted with ethyl acetate (75 mL), filtered, and the filter cake was dried in vacuo to yield pure 2-[[(Dimethylamino)methylene]amino]-3-(2-ethoxy-2-oxoethyl)-5,6,7-tetrahydro-4H-cycloheptathiazolium bromide (Formula G-3) (24.3 g), m.p. 155–158°.

Anal. Calcd for C$_{15}$H$_{24}$BrN$_3$O$_2$S: C, 46.16; H, 6.20; Br, 20.47; N, 10.76; S, 8.21. Found: C, 45.84; H, 6.14; Br, 20.74; N, 10.70; S, 8.14. MS (FAB) m/z 310 (M$^+$−Br) IR (mull) 3200–3500, 1638, 1601, 1513, 1483, 1422, 1407, 1392, 1290, and 1212 cm$^{-1}$. NMR (CDCl$_3$) δ 1.30 (t, J=7.2 Hz, 3 CH$_3$), 1.65–1.95 (m, 6, CH$_2$), 2.65 (m, 2, CH$_2$), 2.76 (m, 2, CH$_2$), 3.17 (s, 3, CH$_3$), 3.61 (s, 3, CH$_3$), 4.26 (q, J=7.2 Hz, 2, CH$_2$), 4.92 (s, 2, CH$_2$), 9.49 (s, 1, CH).

PREPARATION 28
6,7,8,9-Tetrahydro-5H-cyclohept[d]imidazo[2,1-b]thiazole-3-carboxylic acid ethyl ester (Formula G-4) Refer to Chart G.

A solution of 2-[[(Dimethylamino)methylene]amino]-3-(2-ethoxy-2-2-oxoethyl)-5,6,7-tetrahydro-4H-cycloheptathiazolium bromide (Formula G-3)(21.3 g) in DMF (80 mL) was treated with DBU (16.3 mL) and reacted for 72 hours. The solution was diluted with ice-water (400 mL) and precipitated 6,7,8,9-Tetrahydro-5H-cyclohept[d]imidazo[2,1-b]thiazole-3-carboxylic acid ethyl ester (Formula G-4)(11.7 g) was filtered. Crystallization of an aliquot of the precipitate from ethyl acetate-hexane solution gave pure 6,7,8,9-Tetrahydro-5H-cyclohept[d]imidazo[2,1-b]thiazole-3-carboxylic acid ethyl ester (Formula G-4), m.p. 73–74°.

Anal. Calcd for C$_{13}$H$_{16}$N$_2$O$_2$S: C, 59.07; H, 6.10; N, 10.60; S, 12.13; Found: C, 58.78; H, 6.17; N, 10.59; S, 12.03. MS m/z 264 (M$^+$), 249, 235, 219, 218, 217, 192, 190, and 91. IR (mull) 1710, 1498, 1430, 1301, 1281, 1275, 1204, 1174, 1164, 1115, 1094, and 1079 cm$^{-1}$. NMR (CDCl$_3$) 1.37 (t, J=7 Hz, 3, CH$_3$), 1.83 (m, 6, CH$_2$), 2.73 (m, 2, CH$_2$), 3.46 (m, 2, CH$_2$), 4.31 (q, J=7 Hz, 3, CH$_3$), 7.95 (s, 1, CH).

PREPARATION 29
6,7,8,9-Tetrahydro-5H-cyclohept[d]imidazo[2,1-b]thiazole-3-methanol (Formula G-5) Refer to Chart G.

A solution of 6,7,8,9-Tetrahydro-5H-cyclohept[d]imidazo[2,1-b]thiazole-3-carboxylic acid ethyl ester (Formula G-4) (11.7 g) in THF (50 mL) was treated with LiAlH$_4$ (2.24 g) at 0° and reacted at ambient temperature for 1.5 hours. The reaction was quenched by serial additions of water and 15% sodium hydroxide. The mixture was filtered and the filtrate was evaporated to yield crude 6,7,8,9-Tetrahydro-5H-cyclohept[d]imidazo[2,1-b]thiazole-3-methanol (Formula G-5). Crystallization of crude 6,7,8,9-Tetrahydro-5H-cyclohept[d]imidazo[2,1-b]thiazole-3-methanol (Formula G-5) from iso-propanol solution gave pure 6,7,8,9-Tetrahydro-5H-cyclohept [d]imidazo[2,1-b]thiazole-3-methanol (Formula G-5) (7.7 g) m.p. 145–146°.

Anal. Calcd for $C_{11}H_{14}N_2OS$: C, 59.43; H, 6.35; N, 12.60; S, 14.24. Found: C, 59.43; H, 6.43; N, 12.78; S, 14.28. MS m/z 222 (M$^+$), 205, 193, 176, 164, 163, 151, 113 and 91. IR (mull) 3232, 3118, 3072, 1650, 1643, 1631, 1613, 1554, 1546, 1361, 1355, 1337, 1318, 1295, 1779, 1243, 1143, 1137, 1029, and 1025 cm$^{-1}$. NMR (CDCl$_3$) δ1.85 (m, 6, CH$_2$), 2.69 (m, 2, CH$_2$), 3.16 (m, 2, CH$_2$), 4.09 (b, 1, OH), 4.72 (s, 2, CH$_2$), 6.90 (s, 1, CH).

PREPARATION 30
6,7,8,9-Tetrahydro-5H-cyclohept[d]imidazo[2,1-b]thiazole-3-carboxaldehyde (Formula G-6) Refer to Chart G.

A solution of 6,7,8,9-Tetrahydro-5H-cyclohept[d]imidazo [2,1-b]thiazole-3-methanol (Formula G-5) (7.7 g) in DMF (50 mL) and toluene (220 mL) was treated with MnO$_2$ (14.3 g) and azeotropically distilled for 7 hours. The cooled mixture was filtered, the filtrate was concentrated to 50 mL, diluted with water and precipitated 6,7,8,9-Tetrahydro-5H-cyclohept [d]imidazo[2,1-b]thiazole-3-carboxaldehyde (Formula G-6)(6.89 g) was filtered. Crystallization from isopropanol solution gave pure 6,7,8,9-Tetrahydro-5H-cyclohept [d]imidazole[2,1-b]thiazole-3-carboxaldehyde (Formula G-6)(6.7 g), m.p. 96–97°.

Anal. Calcd for $C_{11}H_{12}N_2OS$: C, 59.97; H, 5.49; N, 12.72; S, 14.56. Found: C, 59.96; H, 5.48; N, 12.77; S, 14.46. MS m/z 220 (M$^+$), 205, 203, 192, 191, 175, 174, 164, 163, 150 and 91. IR (mull) 3098, 1651, 1502, 1445, 1396, 1344, 1312, 1272, and 1155 cm$^{-1}$. NMR (CDCl$_3$) δ1.75–2.0 (m, 6, CH$_2$), 2.75 (m, 2, CH$_2$), 3.58 (m, 2, CH$_2$), 7.98 (s, 1, CH), 9.51 (s, 1, CH).

EXAMPLE 15
6,7,8,9-Tetrahydro-α-(2-phenylethyl)-5H-cyclohept[d] imidazo[2,1-b]thiazole-3-methanol (Formula G-7) Refer to Chart G.

A suspension of Mg (0.15 g) in ether (15 mL) was treated with (2-bromoethyl)benzene (0.91 mL) and reacted for 2.5 hours. This Grignard reagent was treated with 6,7,8,9-Tetrahydro-5H-cyclohept [d]imidazole[2,1-b]thiazole-3-carboxaldehyde (Formula G-6) (0.44 g) and reacted for 24 hours. The supernate was decanted into 5% ammonium chloride solution (100 mL) and the mixture was extracted with ethyl acetate. Drying and evaporation of solvent gave a viscous residue (1.0 g) which deposited pure 6,7,8,9-Tetrahydro-α-(2-phenylethyl)-5H-cyclohept [d]imidazo[2, 1-b]thiazole-3-methanol (Formula G-7) (0.30 g), m.p. 152–154° from isopropanol solution.

Anal. Calcd for $C_{19}H_{22}N_2OS$: C, 69.90; H, 6.79; N, 8.58; S, 9.82. Found: C, 69.59; H, 6.81; N, 8.39; S, 9.77. MS m/z 326 (M$^+$), 309, 299, 282, 222, 221, 205, 203, 178, 175, 165, 129, and 91. IR (mull) 3209, 3131, 3091, 3066, 3028, 1611, 1606, 1436, 1360, 1342, 1332, 1313, 1274, 1161, 1152, 1073, 1050, and 981 cm$^{-1}$. NMR (CDCl$_3$) δ1.79 (m, 6, CH$_2$), 2.26 (m, 2, CH$_2$), 2.50 (b, 1, OH), 2.6–3.0 (m, 5, CH$_2$), 3.30 (m, 1, CH$_2$), 4.88 (t, J=5 Hz, CH), 7.05 (s, 1, CH), 7.1–7.35 (m, 5, ArH).

EXAMPLE 16
6,7,8,9-Tetrahydro-α-(4-phenylbutyl)-5-H-cyclohept[d] imidazo[2,1-b]thiazole-3-methanol (Formula G-8) Refer to Chart G.

A suspension of Mg (0.15 g) in ether (15 mL) was treated with 1-bromo-4-phenylbutane (1.4 g) and the Grignard reagent was generated during 2.5 hours. Solid 6,7,8,9-Tetrahydro-5H-cyclohept [d]imidazo[2,1-b]thiazole-3-carboxaldehyde (Formula G-6) (0.44 g) was added and reacted for 24 hours. The supernate was decanted into 5% ammonium chloride solution, product extracted into ethyl acetate, and the extract was evaporated to an oil. The residue was triturated with hexane and pure 6,7,8,9-Tetrahydro-α-(4-phenylbutyl)-5H-cyclohept [d]imidazo[2,1-b]thiazole-3-methanol (Formula G-8) (0.61 g) was filtered, m.p. 106° after recrystallization from acetonitrile solution.

Anal. Calcd for $C_{21}H_{26}N_2OS$: C, 71.15; H, 7.39; N, 7.90; S, 9.04. Found: C, 70.82; H, 7.40; N, 7.73; S, 9.12. MS m/z 354 (M$^+$), 337, 336, 263, 245, 221, 205, 203, 193, 168, 165, and 91. IR (mull) 3195, 3083, 3059, 3021, 1611, 1604, 1496, 1434, 1367, 1353, 1330, 1314, 1305, 1272, 1231, 1214, 1156, 1147, 1081, and 1062 cm$^{-1}$. NMR (CDCl$_3$) δ1.4–2.1 (m, 13, CH$_2$, OH), 2.6–2.75 (m, 4, CH$_2$), 3.05 (m, 1, CH$_2$), 3.32 (m, 1, CH$_2$), 4.87 (t, 1, CH), 7.07 (s, 1, CH), 7.15–7.25 (m, 5, ArH).

PREPARATION 31
N'-(5,6,7,8,9,10-hexahydrocyclooctathiazolyl)-N,N-dimethylmethimidamide (Formula H-2) Refer to Chart H.

A solution of 2-aminocyclooctenothiazole (Formula H-1) (3.64 g) in toluene (20 mL) and DMF-dimethylacetal (5.3 mL) was heated at reflux temperature for 1.5 hours. The cooled solution was diluted with toluene, treated with charcoal, filtered and evaporated to a crystalline residue. The residue was crystallized from hexane to yield pure N'-(5,6, 7,8,9,10-hexahydrocyclooctathiazolyl)-N,N-dimethylmethimidamide (Formula H-2) (4.8 g), m.p. 53–56°.

Anal. Calcd for $C_{12}H_{19}N_3S$: C, 60.72; H, 8.07; N, 17.70; S, 13.51. Found: C, 60.69; H, 8.07; N, 17.76; S, 13.30. MS m/z 237 (M$^+$), 222, 209, 194, 182, 180, 115, and 98. IR (mull) 1622, 1618, 1549, 1494, 1433, 1413, 1405, 1344, 1334, 1181, 1106, and 1097 cm$^{-1}$. NMR (CDCl$_3$) δ1.42 (m, 4, CH$_2$), 1.65 (m, 4, CH$_2$), 2.73 (m, 4, CH$_2$), 3.05 (s, 3, CH$_3$), 3.07 (s, 3, CH$_3$), 8.08 (s, 1, CH).

PREPARATION 32
2-[[(Dimethylamino)methylene]amino]-3-(2-ethoxy-2-oxoethyl)-5,6,7,8,9,10-hexahydrocyclooctathiazolium bromide hydrate (Formula H-3) Refer to Chart H.

A solution of N'-(5,6,7,8,9,10-hexahydrocyclooctathiazolyl)-N,N-dimethylmethimidamide (Formula H-2) (6.34 g) in ethyl bromoacetate (23 mL) was reacted at 25° for 96 hours. The suspension of thiazolium salt (Formula H-3) was diluted with ethyl acetate 250 mL and precipitated 2-[[(Dimethylamino)methylene]amino]-3-(2-ethoxy-2-oxoethyl)-5,6,7,8,9,10-hexahydrocyclooctathiazolium bromide hydrate (Formula H-3) (9.94 g) was filtered. An aliquot crystallized from 2:1 ethyl acetate:acetonitrile analyzed as the hydrate, m.p. 96–99°.

Anal. Calcd for $C_{16}H_{26}BrN_3O_2S \cdot H_2O$: C, 45.50; H, 6.68; Br, 18.92; N, 9.95; S, 7.59. Found: C, 45.44; H, 6.66; Br, 18.80; N, 9.93; S, 7.61. MS (FAB) m/z 324 (M$^+$–Br). IR (mull) 3457, 3410, 1751, 1650, 1612, 1523, 1485, 1420, 1400, 1209, 1201, and 1130 cm$^{-1}$. NMR (CDCl$_3$) δ1.29 (t, 3, CH$_3$), 1.49 (m, 4, CH$_2$), 1.71 (m, 4, CH$_2$), 2.72 (t, J=6.2 Hz, 2, CH$_2$), 2.78 (t, J=6.2 Hz, 2, CH$_2$), 3.17 (s, 3, CH$_3$), 3.63 (s, 3, CH$_3$), 4.83 (s, 2, CH$_2$), 9.49 (s, 1, CH).

PREPARATION 33
5,6,7,8,9,10-Hexahydro-cyclooct[d]imidazo[2,1-b]thiazole-3-carboxylic acid ethyl ester (Formula H-4) Refer to Chart H.

A solution of 2-[[(Dimethylamino)methylene]amino]-3-(2-ethoxy-2-oxoethyl)-5,6,7,8,9,10-hexahydrocyclooctathiazolium bromide hydrate (Formula H-3) (9.6 g) in DMF (45 mL) was treated with DBU (5.3 mL) and reacted for 48 hours. The solution was diluted with cold water, acidified with 5% acetic acid solution, and precipitated 5,6,7,8,9,10-Hexahydro-cyclooct[d]imidazo[2,1-b]thiazole-3-carboxylic acid ethyl ester (Formula H-4) (4.7 g) was filtered. The crude product was fractionated on silica gel with 3:1 hexane:ethyl acetate to yield pure 5,6,7,8,9,10-hexahydrocyclooct[d]imidazo[2,1-b]thiazole-3-carboxylic acid ethyl ester (Formula H-4)(1.85 g), m.p. 79–81°, after crystallization from isopropanol solution.

Anal. Calcd for $C_{14}H_{18}N_2O_2S$: C, 60.41; H, 6.52; N, 10.06; S, 11.52. Found: C, 60.24; H, 6.44; N, 9.95; S, 11.37. MS m/z 278 ($M^+$), 263, 250, 233, 232, 231, 221, 199, 177, 107, and 105. IR (mull) 1718, 1505, 1431, 1350, 1310, 1269, 1214, 1200, 1167, 1153, 1117, 1109, 1090, 1036, and 1032 $cm^{-1}$. NMR ($CDCl_3$) δ1.35 (t, J=6 Hz, 3, $CH_3$), 1.54 (m, 2, $CH_2$), 1.7–1.9 (m, 6, $CH_2$), 2.75 (t, J=6 Hz, 2, $CH_2$), 3.41 (t, J=6 Hz, 2, $CH_2$), 4.30 (q, J=6 Hz, 2, $CH_2$), 7.97 (s, 1, CH).

PREPARATION 34

5,6,7,8,9,10-Hexahydrocyclooct[d]imidazo[2,1-b]thiazole-3-methanol (15d) (Formula H-5) Refer to Chart H.

A solution of 5,6,7,8,9,10-Hexahydro-cyclooct[d]imidazo[2,1-b]thiazole-3-carboxylic acid ethyl ester (Formula H-4) (1.85 g) in THF (50 mL) was treated with $LiAlH_4$ (0.43 g) and reacted for 5 hours. The suspension was diluted to 100 mL with THF and excess reagent was quenched with water then 15% sodium hydroxide. The mixture was filtered and the filtrate was evaporated to yield pure 5,6,7,8,9,10-Hexahydrocyclooct[d]imidazole[2,1-b]thiazole-3-methanol (Formula H-5) (1.44 g) which was used without further purification.

NMR (DMSO) δ1.40 (m, 4, $CH_2$), 1.6–1.75 (m, 4, $CH_2$), 2.77 (t, J=6 Hz, 2, $CH_2$), 3.10 (t, J=6 Hz, 2, $CH_2$), 4.58 (d, J=5 Hz, 2, $CH_2$), 5.32 (t, J=5 Hz, 1, OH), 7.08 (s, 1, CH).

PREPARATION 35

5,6,7,8,9,10-Hexahydro-cyclooct[d]imidazo[2,1-b]thiazole-3-carboxaldehyde (Formula H-6) Refer to Chart H.

A solution of 5,6,7,8,9,10-Hexahydrocyclooct[d]imidazo[2,1-b]thiazole-3-methanol (Formula H-5) (1.6 g) in hot toluene (250 mL) was treated with $MnO_2$ (3.8 g) and azeotropically distilled for 1 hour. The cooled mixture was filtered and the combined filtrate and ethyl acetate washes were evaporated to yield pure 5,6,7,8,9,10-Hexahydro-cyclooct[d]imidazo[2,1-b]thiazole-3-carboxaldehyde (Formula H-6) (1.41 g), m.p. 106–107°, after crystallization from hexane.

NMR ($CDCl_3$) δ1.40 (m, 4, $CH_2$), 1.55 (m, 4, $CH_2$), 2.80 (m, 2, $CH_2$), 3.42 (m, 2, $CH_2$), 8.00 (s, 1, CH), 9.56 (s, 1, CH).

EXAMPLE 17

5,6,7,8,9,10-Hexahydro-α-(2-phenylethyl)cyclooct[d]imidazo-[2,1-b]thiazole-3-methanol (Formula H-7) Refer to Chart H.

Magnesium (0.29 g) in THF (70 mL) was treated with (2-bromoethyl) benzene (2.22 g) and the Grignard reagent was generated during 24 hours. Solid 5,6,7,8,9,10-Hexahydro-cyclooct[d]imidazo[2,1-b]thiazole-3-carboxaldehyde (Formula H-6) (0.70 g) was added, reacted for 2.5 hours and the supernate was decanted into 5% ammonium chloride solution. The precipitated 5,6,7,8,9,10-Hexahydro-α-(2-phenylethyl)cyclooct[d]imidazo-[2,1-b]thiazole-3-methanol (Formula H-7) was extracted into ethyl acetate, the extracts were washed, dried, and evaporated to a viscous residue (1.51 g). Crystallization of the residue from acetonitrile solution provided pure 5,6,7,8,9,10-Hexahydro-α-(2-phenylethyl)cyclooct[d]imidazo-[2,1-b]thiazole-3-methanol (Formula H-7) (0.79 g), m.p. 123–124°.

Anal. Calcd for $C_{20}H_{24}N_2OS$: C, 70.55; H, 7.10; N, 8.23; S, 9.42. Found: C, 70.36; H, 6.90; N, 8.18; S, 9.25. MS m/z 340 ($M^+$), 323, 322, 313, 296, 235, 219, 217, 236, 235, 219, 217, 207, 179, 165, 129, 105, and 91. IR (mull) 3378, 3210, 3103, 3080, 3061, 3047, 3023, 1647, 1613, 1603, 1492, 1448, 1361, 1324, 1311, 1307, 1244, 1133, and 1041 $cm^{-1}$. NMR ($CDCl_3$) 1.2–1.9 (m, 8, $CH_2$), 2.20 (b, 1, OH), 2.25–2.40 (m, 2, $CH_2$), 2.6–3.0 (m, 3, $CH_2$), 3.20 (m, 1, $CH_2$), 4.75 (t, J=5 Hz, 1, $CH_2$), 7.11 (s, 1, CH), 7.17–7.34 (m, s, ArH).

PREPARATION 36

Imidazo[2,1-b]benzothiazole-3-methanol (Formula J-2) Refer to Chart J.

A solution of imidazo[2,1-b]benzothiazole-3-carboxylic acid ethyl ester (Formula J-1), (synthesized from 2-aminobenzothiazole by a modification of the procedures described by Fajeli et al., *Heterocycles*, 1986, 24, 379) (4.5 g) in THF (75 mL) was treated with $LiAlH_4$ (0.91 g) and reacted for 5.25 hours. The suspension was quenched by serial additions of water and 15% sodium hydroxide. The suspension was diluted with THF and filtered. The filtrate was evaporated, the residue was triturated with hexane to yield imidazo[2,1-b]benzothiazole-3-methanol (Formula J-2) (2.77 g, 74%). Crude imidazo[2,1-b]benzothiazole-3-methanol (Formula J-2) was used without further purification.

NMR ($CDCl_3$) δ4.75 (s, 2, $CH_2$), 7.10 (s, 1, CH), 7.1–7.5 (m, 3, ArH), 7.7 (m, 1, ArH).

PREPARATION 37

Imidazo[2,1-b]benzothiazole-3-carboxaldehyde (Formula J-3) Refer to Chart J.

A solution of imidazo[2,1-b]benzothiazole-3-methanol (Formula J-2) (2.0 g) in DMF (30 mL) and toluene (200 mL) was treated with $MnO_2$ (4.5 g) and the mixture was azeotropically distilled for 4.5 hours. A second change of $MnO_2$ (2.0 g) and distillation for 1 hour completed the conversion. The suspension was filtered, the combined filtrate and ethyl acetate washes of the cake were concentrated, the residue was diluted with water, and filtered to yield imidazo[2,1-b]benzothiazole-3-carboxaldehyde (Formula J-3) (2.0 g). Crude imidazo[2,1-b]benzothiazole-3-carboxaldehyde (Formula J-3) was used without further purification.

NMR ($CDCl_3$) δ7.1–7.5 (m, 3, ArH), 8.09 (s, 1, CH), 9.0 (d, J=9 Hz, 1, ArH), 9.74 (s, 1, CH).

EXAMPLE 18

α-(2-phenylethyl)-imidazo[2,1-b]benzothiazole-3-methanol (Formula J-4) Refer to Chart J.

Magnesium metal (0.29 g), 12 g atom) in dry THF (70 mL) was treated with (2-bromoethyl) benzene (0.44 mL) and an Iodine crystal. When the Iodine color had discharged additional (2-bromoethyl)benzene (1.2 mL) was added and the suspension was reacted for 24 hours. Solid imidazo[2,1-b]benzothiazole-3-carboxaldehyde (Formula J-3) (0.606 g, 3.0 mmol) was added and the mixture was reacted for 1.25 hours. The solution was decanted into 5% $NH_4Cl$ solution (250 mL) and the mixture was extracted with ethyl acetate. Drying and evaporation of the extract gave pure α-(2-phenylethyl)-imidazo[2,1-b]benzothiazole-3-methanol (Formula J-4) (0.81 g) after trituration of residue with acetonitrile. An aliquot of the triturated product was crystallized from acetonitrile solution to provide an analytical sample of α-(2-phenylethyl)-imidazo[2,1-b]benzothiazole-3-methanol (Formula J-4) (m.p. 174–175°).

Anal. Calcd for $C_{18}H_{16}N_2OS$. C, 70.10; H, 5.23; N, 9.08; S, 10.40. Found: C, 69.96; H, 5.39; N, 8.94; S, 10.46. MS 308 ($M^+$), 291, 264, 217, 203, 187, 175, 148, 134, and 77. IR (mull) 3237, 3157, 3136, 3123, 1602, 1580, 1478, 1327, 1257, 1142, and 1041 $cm^{-1}$. NMR (DMSO) 2.2–2.4 (m, 2, CH$_2$), 2.7–2.9 (m, 2, CH$_2$), 5.07 (q, 1, CH), 5.25 (b, 1, OH), 7.15–7.45 (m, 7, ArH, CH), 7.55 (m, 1, ArH), 7.70 (d, J=8 Hz, 1, ArH), 8.11 (d, J=8 Hz, 1, ArH).

PREPARATION 38
7-Methyl-imidazo[2,1-b]benzothiazole-3-methanol (Formula K-2) Refer to Chart K.

A solution of 7-methylimidazo[2,1-b]benzothiazole-3-carboxylic acid ethyl ester (synthesized from 2-aminomethylbenzothiazole according to a modification of the procedures described by Fajeli et al., *heterocycles*, 1986, 24, 379) (2.69 g) in THF (25 mL) at 0° was treated with LiAlH$_4$ (0.38 g) and reacted at 25° for 4.5 hours. Additional reagent (0.38 g) was required to complete the reduction. Excess reagent was quenched by sequential addition of water (4 mL) and 15% sodium hydroxide. The combined reaction filtrate and ethyl acetate washes were extracted with saline solutions, dried, and evaporated. The residue deposited pure 7-Methyl-imidazo[2,1-b]benzothiazole-3-methanol (Formula K-2) (1.43 g), m.p. 189–191°, from ethanol solution.

Anal. Calcd for C$_{11}$H$_{10}$N$_2$OS. C, 60.53; H, 4.62; N, 12.84; S, 14.69. Found: C, 60.22; H, 4.89; N, 12.66; S, 14.61. MS m/z 218 (M$^+$), 217, 202, 201, 189, 185, 160, 159, 148, 147, 121, and 77. IR (mull) 3202, 1632, 1549, 1495, 1325, 1311, 1285, 1260, 1136, 1127, 1079, and 1035 cm$^{-1}$. NMR (DMSO) δ2.33 (s, 3, CH$_3$), 4.73 (s, 2, CH$_2$), 7.07 (s, 1, CH), 7.27 (d, J=9 Hz, 1, ArH), 7.67 (s, 1, ArH), 7.83 (d, J=9 Hz, 1, ArH).

PREPARATION 39
7-Methyl-imidazo[2,1-b]benzothiazole-3-carboxaldehyde (Formula K-3) Refer to Chart K.

A suspension of 7-Methyl-imidazo[2,1-b]benzothiazole-3-methanol (Formula K-2) (0.82 g) in hot toluene (100 mL) was diluted with dioxane (10 mL) to effect dissolution of 7-Methyl-imidazo [2,1b]benzothiazole-3-methanol (Formula K-2). The solution was treated with activated MnO$_2$ (1.64 g) and azeotropically distilled for 1.25 hours. The suspension was filtered, the cake was washed with hot ethyl acetate, and the filtrate was evaporated to a crystalline solid (0.69 g). Crystallization from isopropanol gave pure 7-Methyl-imidazo[2,1-b]benzothiazole-3-carboxaldehyde (Formula K-3) (0.56 g), m.p. 170–171°.

Anal. Calcd for C$_{11}$H$_8$N$_2$OS. C, 61.09; H, 3.73; N, 12.95; S, 14.83. Found: C, 61.01; H, 3.68; H, 12.91; S, 14.87. MS m/z 216 (M$^+$), 201, 187, 162, 160, 121, and 108. IR (mull) 1676, 1662, 1486, 1361, 1256, and 1159 cm$^{-1}$. NMR (CDCl$_3$) δ2.49 (s, 3, CH$_3$), 7.33 (d, J=9 Hz, 1, ArH), 7.53 (s, 1, ArH), 8.09 (s, 1, CH), 8.94 (d, J=9 Hz, 1, ArH), 9.74 (s, 1, CH).

EXAMPLE 19
7-Methyl-α-(2-phenylethyl)imidazo[2,1-b]benzothiazole-3-methanol (Formula K-4) Refer to Chart K.

Magnesium (0.29 g, 12 g atom) in THF (60 mL) was treated with (2-bromoethyl)-benzene (1.64 mL) and reacted for 18 hours. The suspension was treated with solid 7-Methyl-imidazo [2,1-b]benzothiazole-3-carboxaldehyde (Formula K-3) (0.65 g) and reacted for 2 hours. The reaction mixture was decanted into cold 5% ammonium chloride solution and precipitated 7-Methyl-α-(2-phenylethyl) imidazo[2,1-b]benzothiazole-3-methanol (Formula K-4) (0.96 g) was filtered. An aliquot was crystallized from methylene chloride/ethanol solution to yield pure 7-Methyl-α-(2-phenylethyl) imidazo[2,1-b]benzothiazole-3-methanol (Formula K-4), m.p. 209–210°.

Anal. Calcd for C$_{19}$H$_{18}$N$_2$OS. C, 70.78; H, 5.63; N, 8.69; S, 9.94. Found: C, 70.68; H, 5.67; N, 8.59; S, 9.89. MS m/z 322 (M$^+$), 295, 217, 201, 189, 174, 162, 148, 130, and 65. IR (mull) 3362, 3295, 1544, 1489, 1458, 1324, 1252, 1030, 1083, and 1039 cm$^{-1}$. NMR (DMSO) 2.25 (m, 2, CH$_2$), 2.45 (s, 3, CH$_3$), 2.70–2.95 (m, 2, CH$_2$), 4.95 (q, 1, CH), 5.57 (d, 1, OH), 7.13 (s, 1, CH), 7.22–7.30 (m, 6, ArH), 7.59 (s, 1, CH), 7.96 (d, J=8 Hz, 1, ArH).

PREPARATION 40
7-Fluoro-imidazo[2,1-b]benzothiazole-3-methanol (Formula L-2) Refer to Chart L.

A solution of 7-fluoroimidazo[2,1-b]benzothiazole-3-carboxylic acid ethyl ester, (synthesized from 2-aminomethylbenzothiazole according to a modification of the procedures described by Fajeli et al., *Heterocycles*, 1986, 24, 379) (1.93 g) in dry THF (50 mL) at 0° was treated with LiAlH$_4$ (0.36 g) and reacted at 25° for one hour. The suspension was quenched by serial addition of water and 15% sodium hydroxide. The suspension was filtered and the filtrate was evaporated to yield crude 7-Fluoro-imidazo[2,1-b]benzothiazole-3-methanol (Formula L-2) (1.59 g). Crystallization of crude 7-Fluoro-imidazo[2,1-b]benzothiazole-3-methanol (Formula L-2) from acetonitrile gave pure 7-Fluoro-imidazo[2,1-b]benzothiazole-3-methanol (Formula L-2) (1.3 g), m.p. 240–241°.

Anal. Calcd for C$_{10}$H$_7$FN$_2$OS. C, 54.04; H, 3.17; N, 12.60; S, 14.43. Found: C, 53.73; H, 3.18; N, 12.44; S, 14.05. MS m/z 222 (M$^+$), 205, 193, 178, 177, 166, 164, 162, 126, and 108. IR (mull) 3215, 3125, 3069, 1552, 1492, 1281, 1212, 1202, and 1032 cm$^{-1}$. NMR (CDCl$_3$) δ5.00 (s, 1, CH), 7.1–7.4 (m, 2, ArH, CH), 7.45 (m, 1, ArH), 8.00 (m, 1, ArH).

PREPARATION 41
7-Fluoro-imidazo[2,1-b]benzothiazole-3-carboxaldehyde (Formula L-3) Refer to Chart L.

A solution of 7-Fluoro-imidazo[2,1-b]benzothiazole-3-methanol (Formula L-2) (1.0 g) in DMF (5 mL) was diluted with toluene (200 mL), the warm solution was treated with activated MnO$_2$ (2.34 g) and azeotropically distilled for 4 hours. The cooled suspension ws filtered, the filtrate was concentrated in vacuo and the residue was diluted with ice water. Precipitated 7-Fluoro-imidazo [2,1-b]benzothiazole-3-carboxaldehyde (Formula L-3) was filtered and recrystallized from acetonitrile to yield pure 7-Fluoro-imidazo[2,1-b]benzothiazole-3-carboxaldehyde (Formula L-3) (0.89 g), m.p. 182–183°.

Anal. Calcd for C$_{10}$H$_5$FN$_2$OS. C, 54.54; H, 2.29; N, 12.72; S, 14.56. Found: C, 54.33; H, 2.32; N, 12.70; S, 14.11. MS m/z 220 (M$^+$), 219, 192, 191, 164, 110, and 108. IR (mull) 3306, 3119, 3100, 3082, 1678, 1664, 1582, 1518, 1482, 1441, 1312, 1264, 1250, 1199, 1161 and 889 cm$^{-1}$. NMR (CDCl$_3$) δ7.26 (m, 1, ArH), 7.46 (q, 1, ArH), 8.12 (s, 1, CH), 9.12 (q, 1, ArH), 9.75 (s, 1, CH).

EXAMPLE 20
7-Fluoro-α-(2-phenylethyl)imidazo[2,1-b]benzothiazole-3-methanol (Formula L-4) Refer to Chart L.

Magnesium (0.146 g) in anhydrous ether (15 mL) was treated with (2-bromoethyl)-benzene (0.82 mL) and reacted for 2.5 hours. The Grignard reagent was treated with solid 7-Fluoro-imidazo [2,1-b]benzothiazole-3-carboxaldehyde (Formula L-3) (0.44 g). Incomplete conversion was observed, an additional charge of Grignard reagent was added, and reacted for 24 hours. The reaction mixture was decanted into 5% ammonium chloride solution and extracted with ethyl acetate. The extract was washed, dried, and evaporated to a solid residue (0.60 g) of crude 7-Fluoro-α-(2-phenylethyl)imidazo[2,1-b]benzothiazole-3-methanol (Formula L-4). Crystallization from isopropanol solution gave pure 7-Fluoro-α-(2-phenylethyl) imidazo[2,1-b]benzothiazole-3-methanol (Formula L-4), m.p. 195–196°. Anal. Calcd for $C_{18}H_{15}FN_2OS$. C, 66.24; H, 4.63; N, 8.58; S, 9.82. Found: C, 66.08; H, 4.64; N, 8.48; S, 9.72. MS m/z 326 (M+), 235, 221, 205, 193, 179, 193, 179, 166, 152, and 91. IR (mull). 3301, 1547, 1486, 1321, 1260, 1208, 1200, 1133, and 1039 cm$^{-1}$. NMR (CDCl$_3$/CD$_3$OD) δ2.33 (q, J=7.6 Hz, 2, CH$_2$), 2.76–3.0 (m, 2, CH$_2$), 5.00 (t, J=7.6 Hz, 1, CH), 7.1–7.4 (m, 9, ArH, CH), 8.01 (m, 1, ArH).

PREPARATION 42
7-Methoxy-imidazo[2,1-b]benzothiazole-3-methanol (Formula M-2) Refer to Chart M.

A solution of 7-methoxy-imidazo[2,1-b]benzothiazole-3-carboxylic acid ethyl ester (5.5 g) in THF (150 mL) at 0° was treated with LiAlH$_4$ (1.03 g) and reacted for 1 hour. The reaction was quenched by serial addition of water and 15% sodium hydroxide. The suspension was filtered, the combined filtrate and THF washes were evaporated to yield 7-Methoxy-imidazo [2,1-b]benzothiazole-3-methanol (Formula M-2) (3.9 g). Crystallization from acetonitrile solution gave 7-Methoxy-imidazo[2,1-b]benzothiazole-3-methanol (Formula M-2), m.p. 202–204°.

Anal. Calcd for $C_{11}H_{10}N_2O_2S$. C, 56.39; H, 4.30; N, 11.96; S, 13.69. Found: C,56.27; H, 4.35; N, 11.88; S, 13.37. MS m/z 234 (M+) 217, 202, 192, 190, and 174. IR (mull) 3178, 3067, 3037, 3005, 1613, 1584, 1550, 1495, 1316, 1289, 1233, 1132, 1075, 1048, and 1032 cm$^{-1}$. NMR (CDCl$_3$) δ3.87 (s, 3, CH$_3$), 4.96 (d, 2, CH$_2$), 7.10 (q, J=2.5, 9 Hz, 1, ArH), 7.18 (m, 2, ArH, CH), 7.92 (d, J=9 Hz, 1, ArH).

PREPARATION 43
7-Methoxy-imidazo[2,1-b]benzothiazole-3-carboxaldehyde (Formula M-3) Refer to Chart M.

A solution of 7-Methoxy-imidazo[2,1-b]benzothiazole-3-methanol (Formula M-2) (4.0 g) in DMF (25 mL) was diluted with toluene (200 mL) and the warm solution was treated with MnO$_2$ (8.84 g). The suspension was azeotropically distilled for 4 hours, cooled to 50°, and filtered. The combined filtrate and toluene washes were concentrated and the concentrate was diluted with water. Precipitated 7-Methoxy-imidazo[2,1-b]benzothiazole-3-carboxaldehyde (Formula M-3) (3.8 g) was filtered and recrystallized from acetonitrile to yield pure 7-Methoxy-imidazo [2,1-b]benzothiazole-3-carboxaldehyde (Formula M-3) (3.79 g), m.p. 168–169°.

Anal. Calcd for $C_{11}H_8N_2O_2S$. C, 56.88; H, 3.47; N, 12.06; S, 13.81. Found: C, 56.87; H, 3.49; N, 12.00; S, 13.81. MS m/z 232 (M+), 217, 204, 203, 189, 176, 161, 150, 146, 144, 134, 116. IR (mull) 3111, 3086, 3062, 3011, 1670, 1602, 1515, 1491, 1448, 1356, 1313, 1272, 1231, 1165, and 1029 cm$^{-1}$. NMR (CDCl$_3$) δ3.90 (s, 3, CH$_3$), 7.08 (q, J=2.5, 9 Hz, 1, ArH), 7.21 (d, J=2.5 Hz, 1, ArH0, 8.98 (d, J=9 Hz, 1, ArH).

EXAMPLE 21
7-Methoxy-α-(2-phenylethyl)imidazo[2,1-b]benzothiazole-3-methanol (Formula M-4) Refer to Chart M.

Magnesium (0.146 g) in anhydrous ether (15 mL) was treated with (2-bromoethyl)benzene (0.82 mL) and reacted for 2.5 hours. Solid 7-Methoxy-imidazo[2,1-b]benzothiazole-3-carboxaldehyde (Formula M-3) (0.46 g) was added and reacted for 24 hours. The reaction mixture was quenched with 5% ammonium chloride solution and product was extracted into ethyl acetate. Drying and evaporation of solvent gave crude 7-Methoxy-α-(2-phenylethyl) imidazo[2,1-b]benzothiazole-3-methanol (Formula M-4) which was recrystallized from acetonitrile solution to provide pure 7-Methoxy-α-(2-phenylethyl)imidazo[2,1-b]benzothiazole-3-methanol (Formula M-4) (0.60 g), m.p. 166–167°.

Anal. Calcd for $C_{19}H_{18}N_2O_2S$. C, 67.43; H, 5.36; N, 8.28; S, 9.48. Found: C, 67.20; H, 5.43; N, 8.15; S, 9.31. MS m/z 338 (M+), 311, 294, 247, 246, 233, 218, 217, 205, 190, 162, 147, 146, and 91. IR (mull) 3270, 1610, 1002, 1584, 1543, 1488, 1313, 1286, 1231, 1220, 1069, 1043, 1036 and 866 cm$^{-1}$. NMR (CDCl$_3$) δ2.32 (q, J=7.4 Hz, 2, CH$_2$), 2.59 (d, 1, OH), 2.81–2.94 (m, 2, CH$_2$), 3.85 (s, 1, CH$_3$), 5.01 (m, 1, CH), 6.94 (q, J=2.5, 9 Hz, 1, ArH), 7.09 (d, J=9 Hz, 1, ArH), 7.13 (s, 1, CH), 7.20–7.34 (m, 4, ArH), 7.89 (d, J=9 Hz, 1, ArH).

PREPARATION 44
2-[[(Dimethylamino)methylene]amino]-5,6,7,8-tetrahydro-3-(2-oxopropyl)-4H-cycloheptathiazolium chloride dihydrate (Formula N-3). Refer to Chart N.

A solution of N'-(5,6,7,8-tetrahydro-4H-cycloheptathiazol)-N,N-dimethylmethimidamide (Formula N-2), 1.12 g, in chloroacetone (10 mL) was reacted for 48 hours. The solution was evaporated in vacuo and the residue was evaporated from toluene. The residual oil crystallized in contact with ether and the pure 2-[[(dimethylamino) methylene] amino]-5,6,7,8-tetrahydro-3-(2-oxopropyl)-4H-cycloheptathiazolium chloride was obtained as a dihydrate (1.49 g), m.p. 59°0 (Formula N-3).

Anal. Calcd. for $C_{14}H_{22}ClN_3OS$. C, 47.79; H, 7.45; Cl, 10.08; N, 11.94; S, 9.11. Found: C, 46.90; H, 7.52; Cl, 9.62; S, 8.91. MS m/z 280 (M+–Cl−). IR (mull) 3425, 3377, 1731, 1647, 1517, 1479, 1447, 1435, 1406, and 1365 cm$^{-1}$. NMR (CDCl$_3$) δ1.81 (m, 6, CH$_2$), 2.40 (S, 3, CH$_3$), 2.62 (m, 2, CH$_2$), 2.71 (m, 2, CH$_2$), 3.18 (S, 3, CH$_3$), 3.51 (S, 3, CH$_3$), 5.36 (S, 2, CH$_{2l}$), 8.01 (S, 1, CH).

PREPARATION 45
1-(6,7,8,9-Tetrahydro-5H-cyclohept[d]imidazo[2,1-b] thiazol-3-yl ethanone (Formula N-4). Refer to Chart N.

To a solution of 2-[[(dimethylamino)methylene]amino]-5,6,7,8-tetrahydro-3-(2-oxopropyl)-4H-cycloheptathizolium chloride dihydrate (Formula N-3), 1.0 g, in dimethyl-formamide (5.0 ml), 1,8-diazabicyclo[5,4,0]undec-7-ene (0.9 ml) was added. The solution was reacted for 24 hours, diluted with ice-water and precipitated product was filtered. Crystallization of the dried precipitate (0.502 g) from ether-hexane solution gave pure 1-(6,7,8,9-tetrahydro-5H-cyclohept [d]imidazo[2,1-b]thiazol-3-yl ethanone (0.35 g), m.p. 80–82° (Formula N-4).

Anal. Calcd for $C_{12}H_{14}N_2OS$: C, 61.51; H, 6.02; N, 11.86; S, 13.69. Found: C, 61.31; H, 6.01; N, 11.91; S, 13.46. MS m/z 234 (M+), 219, 206, 196, 177, 91, 77, 65, and 43. IR (mull) 1655, 1442, 1424, 1346, 1307, 1269, 1209, and 1191 cm$^{-1}$.

PREPARATION 46
3-(3-Fluorophenyl)-1-(6,7,8,9-tetrahydro-5H-cyclohept[d] imidazo[2,1-b]thiazol-3-yl)-2-propene-1-one (Formula N-5, X=3-fluoro). Refer to Chart N.

[1-(6,7,8,9-Tetrahydro-5H-cyclohept[d]-imidazo[2,1-b] thiazol-3-yl)-ethanone (Formula N-4), 2.34 g and 3-fluorobenzaldehyde were reacted using non-critical variations of the teachings Example 15 to give 3-(3-fluorophenyl)-1-(6,7,8,9-tetrahydro-5H-cyclohept [d]imidazo[2,1-b]thiazol-3-yl)-2-propene-1-one (Formula N-5, X=3-fluoro), 3.08 g, m.p. 176–177°.

Anal. Calcd for $C_{19}H_{17}FN_2OS$. C, 67.04; H, 5.03; N, 8.23; S, 9.42. Found: C, 67.05; H, 5.04; N, 8.14; S, 9.26. MS m/z 340 (M+), 323, 311, 297, 283, 245, 231, 217, 203, 190, and 121. IR (mull) 1654, 1600, 1505, 1421, 1359, 1307, 1268, 1197, 1034, and 960 cm$^{-1}$. NMR (CDCl$_3$) δ1.84 (m, 6, CH$_2$), 2.79 (m, 2, CH$_2$), 3.48 (m, 1, CH$_2$), 7.12 (m, 1, ArH), 7.22–7.55 (m, 4, ArH), 7.75 (d, J=16 Hz, 1, CH), 8.12 (S, 1, CH).

EXAMPLE 22

α-[2-(3-Fluorophenyl)ethenyl]-6,7,8,9-tetrahydro-5H-imidazo[2,1-b]thiazole-3-methanol (Formula N-8, X=3-fluoro). Refer to Chart N.

3-(3-Fluorophenyl)-1-(6,7,8,9-tetrahydro-5H-cyclohept[d]imidazo[2,1-b]thiazol-3-yl)-2-propene-1-one (Formula N-5, X=3-fluoro), 0.34 g, in ethanol (35 mL) was treated with NaBH$_4$ (0.11 g), reacted for 3 hours, and solvent removed in vacuo. The residue was suspended in water, filtered and the filter cake was crystallized from acetonitrile to provide pure α-[2-(3-fluorophenyl) ethenyl]-6,7,8,9-tetrahydro-5H, imidazo[2,1-b]thiazole-3-methanol, 0.30 g, m.p. 175–176° (Formula N-8, X=3-fluoro).

Anal. Calcd for C$_{19}$H$_{19}$FN$_2$OS. C, 66.64; H, 5.59; N, 8.18; S, 9.36. Found: C, 66.49; H, 5.58; N, 8.16; S, 9.36. MS m/z 342 (M$^+$), 325, 313, 298, 247, 233, 221, 205, 192, and 175. IR (mull) 3126, 3114, 1584, 1445, 1440, 1146, 1140, and 1096 cm$^{-1}$. NMR (CDCl$_3$) δ1.80 (m, 6, CH$_2$), 2.70 (m, 2,CH$_2$), 3.10 (m, 1, CH$_2$), 3.35 (m, 1, CH$_2$), 5.70 (m, 1, CH), 6.55 (q, J=4 Hz, J=15 Hz, 1, CH), 6.72 (d, J=15 Hz, 1, CH), 6.85 (m, 5, ArH, CH).

EXAMPLE 23

α-[2-(3-Fluorophenyl)ethyl]-6,7,8,9-tetrahydro-5H-cyclohept[d]imidazo[2,1-b]thiazol-3-methanol (Formula N-7, X=3-fluoro). Refer to Chart N.

A suspension of 3-(3-fluorophenyl)-1-(6,7,8,9-tetrahydro-5H-cyclohept[d]imidazo[2,1-b]thiazol-3-yl)-2-propene-1-one (Formula N-6, X=3-fluoro), 1.02 g, in THF (100 mL) at −78° was treated with LiAlH$_4$ (0.27 g) and reacted for 18 hours. The mixture was then maintained at −20° for 24 hours and excess reagent was quenched. The mixture was filtered, the filtrate was concentrated, the residue was dissolved in ethyl acetate, washed with saline, dried and evaporated. The residue (0.30 g) was crystallized from acetonitrile to yield pure α-[2-(3-fluorophenyl) ethyl]-6,7,8,9-tetrahydro-5H-cyclohept[d]imidazo[2,1-b]thiazol-3-methanol, 0.21 g (m.p. 141–144°), Formula N-7, X=3-fluoro.

Anal. Calcd for C$_{19}$H$_{21}$FN$_2$OS. C, 66.25; H, 6.15; N, 8.03; S, 9.19. Found: C, 65.58; H, 6.09; N, 8.03; S, 9.19. MS m/z 344 (M$^+$), 317, 221, 203, 193, 175, and 165. IR (mull) 3184, 3136, 3059, 3043, 1614, 1589, 1492, 1273 and 1074 cm$^{-1}$. NMR (CDCl$_3$) δ1.82 (m, 6, CH$_2$), 2.25 (m, 2, CH$_2$), 2.60–3.05 (m, 5, CH$_2$), 3.28 (m, 1, CH$_2$), 4.87 (t, 1, CH), 6.80–7.40 (m, 5, ArH, CH).

PREPARATION 47

6,7,8,9-Tetrahydro-[2-(4-fluorophenyl)-E-ethenyl]-5H-cyclohept[d]imidazo[2,1-b]thiazol-3-yl methanone (Formula N-5, X=4-fluoro).

This compound was prepared as in EXAMPLE 15 by condensation of 1-(6,7,8,9-tetrahydro-5H-cyclohept[d]imidazo[2,1-b]thiazol-3-yl ethanone (Formula N-4) with 4-fluorobenzaldehyde to provide 6,7,8,9-Tetrahydro-[2-(4-fluorophenyl)-E-ethenyl]-5H-cyclohept [d]imidazo[2,1-b]thiazol-3-yl methanone (Formula N-5, X=4-fluoro), 3.1 g, m.p. 187–188°.

Anal. Calcd for C$_{19}$H$_{17}$FN$_2$OS. C, 67.04; H, 5.03; N, 8.23; S, 9.42. Found: C, 66.74; H, 5.12; N, 8.01; S, 9.17. MS m/z 340 (M$^+$), 323, 311, 297, 283, 245, 231, 218, 203, 190, and 175. IR (mull) 1653, 1597, 1589, 1507, 1421, 1361, 1204, 1193, 1158, and 832 cm$^{-1}$. NMR (CDCl$_3$) δ1.84 (m, 6, CH$_2$), 2.76 (m, 2, CH$_2$), 2.44 (m, 2, CH$_2$), 7.05–7.30 (m, 3, ArH, CH), 7.60 (m, 2, ArH), 7.73 (d, J=16 Hz, 1, CH), 8.10 (S, 1, CH).

EXAMPLE 24

α-[2-(4-Fluorophenyl)ethyl]-6,7,8,9-tetrahydro-5H-cyclohept[d]imidazo[2,1-b]thiazol-3-methanol (Formula N-7, X=4-fluoro). Refer to Chart N.

3-(4-Fluorophenyl)-1-(6,7,8,9-tetrahydro-5H-cyclohept[d]imidazo[2,1-b]thiazol-3-yl)-2-propene-1-one, Formula N-5, X=4-fluoro, 1.02 g, was reduced by non-critical variations of EXAMPLE 23 to give pure α-[2-(4-Fluorophenyl)ethyl]-6,7,8,9-tetrahydro-5H-cyclohept [d]imidazo[2,1-b]thiazol-3-methanol (Formula N-7, X=4-fluoro), m.p. 144–146°.

Anal. Calcd for C$_{19}$H$_{21}$FN$_2$OS. C, 66.25; H, 6.15; N, 8.13; S, 9.31. Found: C, 65.99; H, 6.17; N, 8.02; S, 9.22. MS m/z 344 (M$^+$), 327, 317, 221, 205, 193, 165 and 129. IR (mull) 3197, 3133, 1513, 1438, 1234, 1223, 1158 and 1074 cm$^{-1}$. NMR (CDCl$_3$) δ1.85 (m, 6, CH$_2$), 2.25 (m, 2, CH$_2$), 2.60–3.05 (m, 5, CH$_2$), 3.25 (m, 1, CH$_2$), 4.75 (t, 1, CH), 6.95–7.22 (m, 5, ArH, CH).

EXAMPLE 25

α-[2-(4-Fluorophenyl)ethenyl]-6,7,8,9-tetrahydro-5H-cyclohept[d]imidazo[2,1-b]thiazol-3-methanol (Formula N-8, X=4-fluoro). Refer to Chart N.

3-(4-Fluorophenyl)-1-(6,7,8,9-tetrahydro-5H-cyclohept[d]imidazo[2,1-b]thiazol-3-yl)-2-propene-1-one (Formula N-5, X=4-fluoro), was reduced to α-[2-(4-Fluorophenyl)ethenyl]-6,7,8,9-tetrahydro-5H-cyclohept [d]imidazo[2,1-b]thiazol-3-methanol, m.p. 175–176° (Formula N-8, X=4-fluoro) by non-critical variations of EXAMPLE 22.

Anal. Calcd for C$_{19}$H$_{19}$FN$_2$OS. C, 66.64; H, 5.59; N, 8.18; S, 9.36. Found: C, 66.49; H, 5.58; N, 8.16; S, 9.36. MS m/z 342 (M$^+$), 325, 313, 298, 247, 233, 221, 205, 192, and 175. IR (mull) 3126, 3114, 1584, 1445, 1440, 1146, 1140, and 1096 cm$^{-1}$. NMR (CDCl$_3$) δ1.80 (m, 6, CH$_2$), 2.60–2.75 (m, 3, CH$_2$, OH), 3.10 (m, 1, CH), 3.35 (m, 1, CH), 5.70 (b-, 1, CH), 6.45 (q, J=4, J=15 Hz, 1, CH), 6.70 (d, J=15 Hz, 1, CH), 7.04 (m, 2, ArH), 7.40 (m, 2, ArH).

PREPARATION 48

3-(3-Bromophenyl)-1-(6,7,8,9-tetrahydro-5H-cyclohept[d]imidazo[2,1-b]thiazol-3-yl)-2-propene-1-one (Formula N-5, X=3-bromo). Refer to Chart N.

1-(6,7,8,9-Tetrahydro-5H-cyclohept[d]imidazo[2,1-b]thiazol-3-yl)ethanone (Formula N-4), and 4-bromobenzaldehyde (1.62 g) were condensed to provide 3-(3-Bromophenyl)-1-(6,7,8,9-tetrahydro-5H-cyclohept[d]imidazo[2,1-b]thiazol-3-yl)-2-propene-1-one (Formula N-5, X=3-bromo), 1.2 g, m.p. 125–126°, after crystallization from isopropanol.

Anal. Calcd for C$_{19}$H$_{17}$BrN$_2$SO. C, 56.86; H, 4.27; Br, 19.91; N, 6.98; S, 7.99. Found: C, 56.72; H, 4.33; Br, 19.82; N, 6.84; S, 7.97. MS m/z 442, 440 (M$^+$), 245, 231, 102. IR (mull) 3105, 3078, 3060, 1652, 1597, 1421, 1420, 1365, 1305, and 1195 cm$^{-1}$. NMR (CDCl$_3$) 1.84 (m, 6, CH$_2$), 2.76 (m, 2, CH$_2$), 3.44 (m, 2, CH$_2$), 7.31 (m, 2, ArH, CH), 7.52 (m, 2, ArH), 7.72 (m, 2, ArH), 6.12 (S, 1, CH).

PREPARATION 49

3-93-Bromophenyl)-1-(6,7,8,9-tetrahydro-5H-cyclohept[d]imidazo[2,1-b]thiazol-3-yl)-1-propanone (Formula N-6, X=3-Bromo). Refer to Chart N.

A suspensionof Te (1.28 g) in N$_2$-degassed ethanol (20 mL) was treated with NaBH$_4$ (0.83 g) and heated at reflux temperatures for 30 minutes. The mixture was treated with acetic acid (1.2 mL) in ethanol (5 mL) dropwise at −10 to −20°. The mixture was warmed to 25°, treated with solid 3-(3-bromophenyl)-1-(6,7,8,9-tetrahydro-5H-cyclohept[d]imidazo[2,1-b]thiazol-3-yl)-2-propene-1-one (0.40 g, Formula N-5, X=3-bromo) and reacted for 2.5 hours. Air was passed through the mixture, the precipitated inorganic material was filtered, and the filtrate was evaporated to a crystalline residue. Crystallization of the residue from isopropanol gave pure 3-(3-Bromophenyl)-1-(6,7,8,9-tetrahydro-5H-cyclohept [d]imidazo[2,1-b]thiazol-3-yl)-1-propanone (Formula N-6, X=3-Bromo), m.p. 77–79°.

Anal. Calcd for $C_{19}H_{19}BrN_2OS$. C, 56.58; H, 4.75; Br, 19.81; N, 6.95; S, 7.95. Found: C, 56.39; H, 4.66; Br, 19.60; N, 6.79; S, 7.93. MS m/z 404, 402 (M$^+$), 375, 247, 233, 219, and 192. IR (mull) 3122, 3061, 3048, 3010, 1653, 1502, 1475, 1424, 1307, 1273, and 1196 cm$^{-1}$. NMR (CDCl$_3$) δ1.82 (m, 6, CH$_2$), 2.75 (m, 2, CH$_2$), 3.03 (m, 2, CH$_2$), 3.15 (m, 2, CH$_2$), 3.40 (m, 2, CH$_2$), 7.17 (m, 2, ArH), 7.30–7.40 (m, 2, ArH), 7.97 (S, 1, CH).

EXAMPLE 26

α-[2-(3-Bromophenyl)ethyl]-6,7,8,9-tetrahydro-5H-cyclohept[d]imidazo-[2,1-b]thiazol-3-methanol (Formula N-7). Refer to Chart N.

3-(3-Bromophenyl)-1-(6,7,8,9-tetrahydro-5H-cyclohept [d]imidazo[2,1-b]thiazol-3-yl)-1-propanone, 0.10 g, (Formula N-6, X=3-bromo) was reduced by non-critical variations of EXAMPLE 12 to provide α-[2-(3-Bromophenyl)ethyl]-6,7,8,9-tetrahydro-5H-cyclohept [d]imidazo[2,1-b]thiazol-3-methanol (Formula N-7), 0.07 g, m.p. 137–141°.

Anal. Calcd for $C_{19}H_{21}BrN_2OS$. C, 56.30; H, 5.22; Br, 19.71; N, 6.91. Found: C, 56.02; H, 5.24; Br, 19.49; N, 6.78.

MS m/z 406, 404 (M$^+$), 379, 377, 362, 360, 221, 205, 203, and 193.

IR (mull) 3064, 1608, 1594, 1567, 1445, 1434, 1424, 1365, 1325, 1276, 1150, and 1070 cm$^{-1}$.

NMR (CDCl$_3$) 1.80 (m, 6, CH$_2$), 2.22 (m, 2, CH$_2$), 2.60–3.05 (m, 5, CH$_2$), 3.27 (m, 1, CH$_2$), 4.85 (m, 1, CH), 7.0–7.5 (m, 5, ArH, CH).

PREPARATION 50

6,7,8,9-Tetrahydro-[2-(3-chlorophenyl)-ethenyl-5H-cyclohept[d]imidazo [2,1-b]thiazol-3-yl methanone (Formula N-5, X=3-chloro). Refer to Chart N.

1-(6,7,8,9-Tetrahydro-5H-cyclohept[d]-imidazo[2,1-b] thiazol-3-yl ethanone (Formula N-4), 1.87 g, and 3-chlorobenzaldehyde (0.216 g) were condensed following non-critical variations of Example 15 to provide 6,7,8,9-Tetrahydro-[2-(3-chlorophenyl)-ethenyl-5H-cyclohept[d] imidazo[2,1-b]thiazol-3-yl methanone (Formula N-5, X=3-chloro), (2.72 g), m.p. 137–139°.

Anal. Calcd for $C_{19}H_{17}ClN_2OS$. C, 63.95; H, 4.80; Cl, 9.94; S, 8.99. Found: C, 63.93; H, 4.89; Cl, 9.80; N, 7.94; S, 8.97.

MS m/z 358, 356 (M$^+$), 341, 339, 327, 245, 231, 217, and 203.

IR (mull) 1654, 1601, 1494, 1422, 1364, 1190, 1046, 968, 962, and 788 cm$^{-1}$.

NMR (CDCl$_3$) 1.85 (m, 6, CH$_2$), 2.79 (m, 2, CH$_2$), 3.48 (m, 2, CH$_2$), 7.25–7.52 (m, 4, CH, ArH), 7.60 (S, 1, ArH), 7.70 (d, J=16 Hz, 1, CH), 8.12 (S, 1, CH).

PREPARATION 51

3-(3-Chlorophenyl)-1-(6,7,8,9-tetrahydro-5H-cyclohept [d]imidazo[2,1-b]thiazol-3- yl)-1-propanone (Formula N-6, X=3-chloro). Refer to Chart N.

3-(3-Chlorophenyl)-1-(6,7,8,9-tetrahydro-5H-cyclohept [d]imidazo[2,1-b]thiazol-3-yl)-2-propene-1-one (Formula N-5, X=3-chloro) (0.36 g) was reduced by non-critical variations of PREPARATION 49 to yield 3-(3-chlorophenyl)-1-6,7,8,9-tetrahydro-5H-cyclohept[d] imidazo[2,1-b]thiazol-3-yl)-1-propanone (0.30 g), (Formula N-6, X=3-chloro).

MS m/z 360, 358 (M$^+$), 247, 233, 219, 205, 192, 177, 165, 127 and 125.

NMR (CDCl$_3$) δ 1.82 (m, 2, CH$_2$), 2.75 (m, 2, CH$_2$), 3.0–3.2 (m, 4, CH$_2$), 3.41 (m, 2, CH$_2$), 7.05–7.30 (m, 4, ArH), 7.97 (S, 1, CH).

EXAMPLE 27

α-[2-(3-Chlorophenyl)ethyl]-6,7,8,9-tetrahydro-5H-cyclohept[d]imidazo[2,1-b]thiazol-3-methanol (Formula N-7, X=3-chloro). Refer to Chart N.

3-(3-Chlorophenyl)-1-(6,7,8,9-tetrahydro-5H-cyclohept [d]imidazo[2,1-b]thiazol-3-yl)-1-propanone (Formula N-6, X=3-chloro) was reduced accoring to EXAMPLE 12 to provide α-[2-(3-Chlorophenyl)ethyl]-6,7,8,9-tetrahydro-5H-cyclohept[d]imidazo[2,1-b]thiazol-3-methanol (Formula N-7, X=3-chloro).

Anal. Calcd for $C_{19}H_{21}ClN_2OS$. C, 63.23; H, 5.86; Cl, 9.82; N, 7.76; S, 8.88. Found: C, 63.21; H, 5.96; Cl, 9.55; N, 7.72; S, 8.86.

MS m/z 362, 360 (M$^+$), 344, 342, 335, 333, 316, 231, 221, 205, and 91.

IR (mull) 3171, 3115, 3071, 3043, 1437, 1428, 1153, 1078, 795, and 784 cm$^{-1}$.

NMR (CDCl$_3$) δ 1.80 (m, 6, CH$_2$), 2.23 (m, 2, CH$_2$), 2.65–3.10 (m, 6, CH$_2$), 3.28 (m, 1, CH$_2$), 4.84 (t, 1, CH), 6.98 (s, 1, CH), 7.05–7.42 (m, 4, ArH).

PREPARATION 52

3-(3,5-Difluorophenyl)-1-(6,7,8,9-tetrahydro-5H-cyclohept[d]imidazo[2,1-b]thiazol-3-yl)-2-propene-1-one (Formula N-5, X=3,5-difluoro). Refer to Chart N.

1-(6,7,8,9-Tetrahydro-5H-cyclohept[d]imidazo[2,1-b] thiazol-3-yl)-ethanone (Formula N-4, 1.8 g in THF (50 mL) was condensed with 3,5-difluorobenzaldehyde according to non-critical variations in PREPARATION 15 to yield pure 3-(3,5-Difluorophenyl)-1-(6,7,8,9-tetrahydro-5H-cyclohept [d]imidazo[2,1-b]thiazol-3-yl)-2-propene-1-one (Formula N-5, X=3,5-difluoro), 0.51 g, m.p. 207–209°.

Anal. Calcd for $C_{19}H_{16}F_2N_2OS$. C, 63.67; H, 4.50; N, 7.82; S, 8.95. Found: C, 63.32; H, 4.47; N, 7.72; S, 8.80.

MS m/z 358 (M$^+$), 339, 330, 301, 245, 231, 217, 203, 190, 167, and 139.

IR (mull) 1655, 1620, 1600, 1450, 1419, 1364, 1305, 1197, 1124, and 847 cm$^{-1}$.

NMR (CDCl$_3$) δ 1.84 (m, 6, CH$_2$), 2.76 (m, 2, CH$_2$), 3.44 (m, 2, CH$_2$), 6.86 (m, 1, ArH), 7.11 (m, 2, ArH), 7.30 (d, J=19 Hz, 1, CH), 7.67 (d, J=19 Hz, 1, CH), 8.15 (s, 1, CH).

PREPARATION 53

3-(3,5-Difluorophenyl)-1-(6,7,8,9-tetrahydro-5H-cyclohept[d]imidazo[2,1-b]thiazol-3-yl)-1-propanone (Formula N-6, X=3,5-difluoro). Refer to Chart N.

3-(3,5-Difluorophenyl)-1-(6,7,8,9-tetrahydro-5H-cyclohept[d]imidazo[2,1-b]thiazol-3-yl)-2-propene-1-one (Formula N-5, X=3,5-difluoro) (0.25 g) was reduced with NaHTe to 3-(3,5-Difluorophenyl)-1-(6,7,8,9-tetrahydro-5H- cyclohept[d]imidazo[2,1-b]thiazol-3-yl)-1-propanone (0.15 g), (Formula N-6, X=3,5-difluoro), m.p. 112–114°, according to non-critical variation of PREPARATION 49.

MS m/z 360 (M$^+$), 317, 247, 219, 193, 192 and 127.

NMR (CDCl$_3$) δ 1.81 (m, 6, CH$_2$), 2.73 (m, 2, CH$_2$), 3.05 (m, 2, CH$_2$), 3.13 (m, 2, CH$_2$), 3.43 (m, 2, CH$_2$), 6.45 (m, 1, ArH), 6.76 (m, 2, ArH), 7.99 (S, 1, CH).

EXAMPLE 28

α-[2-(3,5-Difluorophenyl)ethyl]-1-6,7,8,9-tetrahydro-5H-cyclohept[d]-imidazothiazol-3-methanol (Formula N-7, X=3,5-difluoro). Refer to Chart N.

3-((3,5-Difluorophenyl)-1-(6,7,8,9-tetrahydro-5H-cyclohept[d]imidazo[2,1-b]thiazol-3-yl)-1-propanone (Formula N-6, X=3,5-difluoro), 0.10 g, was reduced with NaBH$_4$ according to non-critical variations of EXAMPLE 12 to yield α-[2-(3,5-Difluorophenyl)ethyl]-6,7,8,9-tetrahydro-5H-cyclohept[d]imidazothiazol-3-methanol (Formula N-7, X=3,5-difluoro), 0.09 g, m.p. 165–166°.

Anal. Calcd for C$_{19}$H$_{20}$F$_2$N$_2$OS. C, 62.96; H, 5.56; N, 7.73; S, 8.85. Found: C, 63.22; H, 5.51; N, 7.80; S, 8.79.

MS m/z 362 (M$^+$), 344, 335, 318, 231, 221, 193, 165, and 91.

IR (mull) 3186, 3135, 1625, 1595, 1432, 1318, 1314, 1112, 986 and 965 cm$^{-1}$.

NMR (CDCl$_3$) δ 1.82 (m, 6, CH$_2$), 2.25 (M, 2, CH$_2$), 2.65–3.05 (m, 5, CH$_2$), 3.30 (m, 1, CH), 4.85 (m, 1, CH), 6.6–6.8 (m, 3, ArH), 7.10 (S, 1, CH).

PREPARATION 54

6,7,8,9-Tetrahydro-[2-(4-dimethylaminophenyl)-E-ethenyl]-4H-cyclohept[d]imidazo[2,1-b]thiazol-3-yl-methanone (Formula N-5, X=4-dimethylamino).

1-(6,7,8,9-Tetrahydro-5H-cyclohept[d]imidazo[2,1-b]thiazol-3-yl ethanone (Formula N-4), 3.51 g, and 4-dimethylaminobenzaldehyde (4.48 g) were condensed according to non-critical variations of PREPARATION 15 to yield pure 6,7,8,9-Tetrahydro-[2-(4-dimethylaminophenyl)-E-ethenyl]-4H-cyclohept[d]imidazo[2,1-b]thiazol-3-yl-methanone (3.78 g), m.p. 214–215°.

Anal. Calcd for C$_{21}$H$_{23}$N$_3$OS. C, 69.01; H, 6.34; N, 11.50; S, 8.77. Found: C, 68.75; H, 6.46; N, 11.43; S, 8.65.

MS m/z 365 (M$^+$), 350, 231, 218, 190, 174, 146, and 134.

IR (mull) 1645, 1610, 1573, 1524, 1506, 1422, 1360, 1182, 1171, and 815 cm$^{-1}$.

NMR (CDCl$_3$) δ 1.85 (m, 6, CH$_2$), 2.77 (m, 2, CH$_2$), 3.05 (S, 6, CH$_3$), 3.44 (m, 2, CH$_2$), 6.71 (d, J=9 Hz, 2, ArH), 7.10 (d, J=16 Hz, 1, CH), 7.51 (d, J=9 Hz, 2, ArH, 7.75 (d, J=16 Hz, 1, CH), 8.03 (S, 1, CH).

EXAMPLE 29

α-[2-(4-dimethylaminophenyl)ethyl-6,7,8,9-tetrahydro-5H-cyclohept[d]-imidazo-[2,1-b]thiazol-3-methanol (Formula N-7, X=4-dimethylamino). Refer to Chart N.

3-(4-Dimethylaminophenyl)-1-(6,7,8,9-tetrahydro-5H-cyclohept[d]imidazo[2,1-b]thiazol-3-yl)-2-propene-1-one (Formula N-5, X=4-dimethylamino), was reduced according to non-critical variations of EXAMPLE 23 to provide α-[2-(4-dimethylaminophenyl)ethyl-6,7,8,9-tetrahydro-5H-cyclohept[d]imidazo[2,1-b]thiazol-3-methanol (Formula N-7, X=4-dimethylamino), 0.15 g, m.p. 168–170°, after chromatographic purification.

Anal. Calcd for C$_{21}$H$_{27}$N$_3$OS. C, 68.26; H, 7.36; N, 11.37; S, 8.68. Found: C, 68.08; H, 7.34; N, 11.33; S, 8.61.

MS m/z 369 (M$^+$), 354, 235, 221, 193, 177, 163, 148 and 134.

IR (mull) 3149, 3118, 3099, 1616, 1522, 1446, 1347, 1150, and 1052 cm$^{-1}$.

NMR (CDCl$_3$) δ 1.73–2.02 (m, 6, CH), 2.26 (m, 2, CH$_2$), 2.6–2.85 (m, 5, CH$_2$), 2.92 (S, 6, CH$_3$), 3.30 (m, 1, CH), 4.90 (b, 1, CH), 6.70 (d, J=9 Hz, 2, ArH), 7.08 (d, J=9 Hz, 2, ArH), 7.11 (S, 1, CH).

EXAMPLE 30

α-[2-(4-Dimethylaminophenyl)ethenyl]-6,7,8,9-tetrahydro-5H-cyclohept[d]-imidazo[2,1-b]thiazol-3-methanol (Formula N-8, X=4-dimethylamino). Refer to Chart N.

3-(4-Dimethylaminophenyl)-1-(6,7,8,9-tetrahydro-5H-cyclohept[d]imidazo[2,1-b]thiazol-3-yl)-2-propene-1-one (Formula N-5, X=4-dimethylamino) 0.37 g, was reduced according to non-critical variations of EXAMPLE 22 to provide α-[2-(4-Dimethylaminophenyl)ethenyl]-6,7,8,9-tetrahydro-5H-cyclohept[d]imidazo[2,1-b]thiazol-3-methanol (0.20 g), m.p. 168–170° (Formula N-8, X=4-dimethylamino).

Anal. Calcd for C$_{21}$H$_{25}$N$_3$OS. C, 68.63; H, 6.86; N, 11.43; S, 8.73. Found: C, 68.38; H, 6.80; N, 11.34; S, 8.59.

MS m/z 367 (M$^+$), 350, 338, 220, 205, 175, 158, 149, and 147.

IR (mull) 3133, 3119, 1612, 1522, 1444, 1349, 1145, and 1096 cm$^{-1}$.

NMR (CDCl$_3$) δ 1.79 (m, 6, CH$_2$), 2.60 (b, 1, OH), 2.69 (m, 2, CH$_2$), 2.97 (s, 6, CH$_3$), 3.10 (m, 1, CH$_2$), 3.37 (m, 1, CH$_2$), 5.67 (t, 1, CH), 6.35 (q, 1, CH), 6.60 (d, 1, CH), 6.68 (d, J=9 Hz, 2, ArH), 7.10 (S, 1, CH), 7.30 (d, J=9 Hz, 2, ArH).

PREPARATION 55

(E)-N-[3-[3-(2,3-Dimethylimidazo[2,1-b]thiazol-5-yl)-3-oxo-1-propenyl]phenyl-4-methylbenzenesulfonamide (Formula N'-2, X=3-toluenesulfonamide). Refer to Chart N'.

1-(2,3-Dimethylimidazo[2,1-b]-thiazol-5-yl ethanone (Formula N'-1), 0.97 g, was condensed with the 3-toluensulfonamide of benzaldehyde, m.p. 126–127°, prepared from toluene sulfonyl chloride and 3-aminobenzaldehyde, according to non-critical modifications of PREPARATION 15 to provide pure (E)-N-[3-[3-(2,3-Dimethylimidazo[2,1-b]thiazol-5-yl)-3-oxo-1-propenyl]phenyl-4-methylbenzenesulfonamide, m.p. 236–237°, Formula N'-2.

Anal. Calcd for C$_{23}$H$_{21}$N$_3$O$_3$S$_2$. C, 61.17; H, 4.69; N, 9.30; S, 14.20. Found: C, 60.91; H, 4.75; N, 9.25; S, 14.09.

MS mz 451 (M$^+$), 422, 296, 268, 205, 191, 179, 177, 168, 106, and 91.

IR (mull) 3145, 3101, 3083, 3025, 3012, 1668, 1618, 1603, 1586, 1520, 1433, 1365, 1340, 1311, 1306, 1291, 1270, 1212, and 1159 cm$^{-1}$.

NMR (CDCl$_3$) δ 2.38 (S, 6, CH$_3$), 2.67 (S, 3, CH$_3$), 7.1–7.4 (m, 8, ArH, CH), 7.6–7.7 (m, 3, ArH, CH).

PREPARATION 56

N-[3-[3-(2,3-Dimethylimidazo[2,1-b]thiazol-5-yl)-3-oxopropyl]phenyl]-4-methyl-benzenefulfonamide (Formula N'-3, X=3-toluenesulfonamide). Refer to Chart N'.

(E)-N-[3-[3-(2,3-Dimethylimidazo[2,1-b]thiazol-5-yl)-3-oxo-1-propenyl]phenyl]4-methylbenzenesulfonamide (Formula N'-2, X=3-toluenesulfonamide), 1.19 g, was reduced by non-critical variations of PREPARATION 49 to give pure N-[3-[3-(2,3-Dimethylimidazo[2,1-b]thiazol-5-yl)-3-oxopropyl]phenyl]-4-methyl-benzenesulfonamide (Formula N'-3, X=3-sulfonamide, 0.84 g, m.p. 180–181°.

EXAMPLE 31

N-[3-[3-(2,3-Dimethylimidazo[2,1-b]thiazol-5-yl)-3-hydroxypropyl]phenyl-4-methylbenzenesulfonamide (Formula N'-4, X=3-toluenesulfonamide). Refer to Chart N'.

N-[3-[3-(2,3-Dimethylimidazo[2,1-b]thiazol-5-yl)-3-oxopropyl]phenyl]-4-methyl-benzenefulfonamide (Formula N'-3, X=3-toluenesulfonamide) was reduced by making non-critical variations in EXAMPLE 12 to yield N-[3-[3-(2,3-Dimethylimidazo[2,1-b]thiazol-5-yl)-3-hydroxypropyl]phenyl-4-methylbenzenesulfonamide (0.27 g, m.p. 183°), Formula N'-3, X=3-toluenesulfonamide.

NMR (CDCl$_3$) 2.27 (S, 3, CH$_3$), 2.30 (s, 3, CH$_3$), 2.42 (S, 3, CH$_3$), 4.85 (t, 1, CH), 6.85–7.20 (m, 7, ArH), 7.60–7.69 (m, 2, ArH, CH).

MS m/z 455 (M$^+$), 437 (M$^+$—H$_2$O), 325, 310, 282, 267, 191, 177, 165, and 154.

IR (mull) 3460, 3024, 2796, 2700, 1608, 1591, 1448, 1434, 1326, and 1151 cm$^{-1}$.

EXAMPLE 32

(E)-N-[3-[3-(2,3-Dimethylimidazo[2,1-b]thiazol-5-yl)-3-hydroxy-1-propenyl]phenyl-4-methylbenzenesulfonamide (Formula N'-5, X=3-toluenesulfonamide). Refer to Chart N'.

(E)-N-[3-[3-(2,3-Dimethylimidazo[2,1-b]thiazol-5-yl)-3-oxo-1-propenyl]-4-methylbenzenesulfonamide (Formula N'-2, X=3-toluenesulfonamide), 0.835 g, was reduced with LiAlH$_4$ by making non-critical variations in EXAMPLE 23 to produce (E)-N-[3-[3-(2,3-Dimethylimidazo[2,1-b]thiazol-5-yl)-3-hydroxy-1-propenyl]phenyl-4-methylbenzenesulfonamide (Formula N'-5-, X=3-toluenesulfonamide), m.p. 177–179° dec.

Anal. Calcd for C$_{23}$H$_{23}$N$_3$O$_3$S$_2$. C, 60.90; H, 5.11; N, 9.26; S, 14.14. Found: C, 60.50; H, 5.09; N, 9.24; S, 13.96.

IR (mull) 3182, 3117, 3072, 1601, 1585, 1331, 1312, 1304, 1236, 1153, 1093, and 1079 cm$^{-1}$.

MS m/z 453 (M$^+$), 435, 301, 280, 265, 253, 191, 179, 165, 153, 146, and 91.

NMR (DMSO) δ 2.31 (S, 1, CH$_3$), 2.37 (S, 1, CH$_3$), 2.59 (S, 1, CH$_3$), 5.53 (d, 1, OH), 5.64 (t, 1, CH), 6.51 (q, J=5, 16 Hz, 1, CH), 6.62, (d, J=16 Hz, 1, CH), 7.0–7.25 (m, 6, ArH), 7.6–7.7 (m, 3, ArH, CH), 9.26 (S, 1, NH).

PREPARATION 57

(E)-N-[2-[3-(2,3-Dimethylimidazo[2,1-b]thiazol-5-yl)-3-oxo-1-propenyl]-phenyl-4-methylbenzenesulfonamide (Formula N'-2, X=2-toluenesulfonamide). Refer to Chart N'.

1-(2,3-Dimethylimidazo[2,1-b]-thiazol-5-yl)-ethanone (Formula N'-1), 0.97 g, was condensed with the toluene sulfonamide of 2-aminobenzaldehyde (1.51 g), prepared by a modification of the procedure described by A. T. Hawson et al., J. Chem. Soc. Perkin 1, 1565 (1991), according to a non-critical variation of PREPARATION 15 to yield pure (E)-N-[2-[3-(2,3-Dimethylimidazo[2,1-b]thiazol-5-yl)-3-oxo-1-propenyl]-phenyl-4-methylbenzenesulfonamide, m.p. 198–199°, as a chloroform solvate, Formula N'-2, X=2-toluenesulfonamide.

Anal. Calcd for C$_{23}$H$_{21}$N$_3$O$_2$S$_2$.CH$_3$Cl$_3$. C, 50.49; H, 3.88; Cl, 18.63; N, 7.36; S, 11.23.

Found: C, 50.40; H, 3.80; Cl, 19.22; N, 7.32; S, 11.32.

MS m/z 296 (M$^+$), 278, 268, 254, 234, 203, 196, 197, 179, and 152.

IR (mull) 3098, 3072, 3059, 1646, 1590, 1484, 1426, 1364, 1338, 1204, and 1171 cm$^{-1}$.

NMR (DMSO) δ 2.27 (S, 3, CH$_3$), 2.42 (S, 3, CH$_3$), 2.67 (S, 3, CH$_3$), 7.04–7.16 (m, 4, ArH, CH=), 7.27 (m, 3, ArH, CHCl$_3$), 7.53 (d, J=8 Hz, 2, ArH), 7.73 (m, 1, ArH), 7.90 (d, J=16 Hz, 1, CH$_3$), 8.10 (S, 1, CH), 9.76 (S, 1, NH).

PREPARATION 58

N-[2-[3-(2,3-Dimethylimidazo[2,1-b]thiazol-5-yl)-3-oxopropyl]phenyl]-4-methylbenzenesulfonamide (Formula N'-3, X=2-toluenesulfonamide). Refer to Chart N'.

(E)-N-[2-[3-(2,3-Dimethylimidazo[2,1-b]thiazol-5-yl)-3-oxo-1-propenyl]-phenyl-4-methylbenzenesulfonamide (Formula N'-2, X=2-toluenesulfonamide), 1.2 g, was reduced to N-[2-[3-(2,3-Dimethylimidazo[2,1-b]thiazol-5-yl)-3-oxopropyl]phenyl]-4-methylbenzenesulfonamide (Formula N'-3, X=2-toluenesulfonamide, 0.63 g, m.p. 168–169°, through non-critical variations in PREPARATION 48.

NMR (CDCl$_3$) δ 2.35 (S, 1, CH$_3$), 2.38 (S, 1, CH$_3$), 2.55 (t, 2, CH$_2$), 2.63 (S, 3, CH$_3$), 3.10 (t, 2, CH$_2$), 7.05–7.25 (m, 5, ArH), 7.45 (d, J=9 Hz, 1, ArH), 7.62 (d, J=9 Hz, 2, ArH), 8.55 (S, 1, CH).

EXAMPLE 33

N-[2-[3-(2,3-Dimethylimidazo[2,1-b]thiazol-5-yl)-3-hydroxy-propyl]phenyl-4-methylbenzensulfonamide (Formula N'-4, X=2-toluenesulfonamide). Refer to Chart N'.

N-[2-[3-(2,3-Dimethylimidazo[2,1-b]thiazol-5-yl)-3-oxopropyl]phenyl]-4-methylbenzenesulfonamide (Formula N'-3, X=2-toluenesulfonamide) was reduced by non-critical variations in EXAMPLE 12 to N-[2-[3-(2,3-Dimethylimidazo[2,1-b]thiazol-5-yl)-3-hydroxy-propyl]phenyl-4-methylbenzensulfonamide (Formula N'-4, X=2-toluenesulfonamide) (0.36 g), m.p. 207–208°.

Anal. Calcd for C$_{23}$H$_{25}$N$_3$O$_3$S$_2$. C, 60.63; H, 5.52; N, 9.22; S, 14.08. Found: C, 60.60; H, 5.62; N, 9.20; S, 14.06.

MS m/z 455 (M$^+$), 437, 282, 256, 195, 181, 165, 153, 130, and 129.

IR (mull) 3170, 1341, 1328, 1165, 1159, 1142, 1093, and 1032 cm$^{-1}$.

NMR (DMSO) 2.23 (S, 3, CH$_3$), 2.37 (S, 3, CH$_3$), 2.48 (S, 3, CH$_3$), 4.70 (m, 1, CH), 5.80 (d, 1, OH), 7.0–7.3 (m, 6, ArH), 7.57 (m, 2, ArH), 7.70 (S, 1, CH).

PREPARATION 59

3-(2,3-Difluorophenyl)-1-(6,7,8,9-tetrahydro-5H-cyclohept[d]imidazo[2,1-b]thiazol-3-yl)-2-propene-1-one (Formula N-5, X=2,3-difluoro). Refer to Chart N.

1-(6,7,8,9-tetrahydro-5H-cyclohept[d]imidazo[2,1-b]thiazol-3-yl)ethanone (Formula N-4), 1.87 g and 2,3-difluorobenzaldehyde (1.39 g) were condensed by non-critical variations in PREPARATION 15 to provide 3-(2,3-Difluorophenyl)-1-(6,7,8,9-tetrahydro-5H-cyclohept[d]imidazo[2,1-b]thiazol-3-yl)-2-propene-1-one (Formula N-5, X=2,3-difluoro), 1.35 g, m.p. 193–195°.

Anal. Calcd for C$_{19}$H$_{16}$F$_2$N$_2$SO. C, 63.67; H, 4.50; N, 7.82; S, 8.95. Found: C, 63.65; H, 4.49; N, 7.41; S, 8.65.

MS m/z 358 (M$^+$), 339, 330, 329, 311, 301, 245, 231, 219, 203, and 191.

IR (mull) 1657, 1484, 1420, 1359, 1309, 1285, 1194, and 1038 cm$^{-1}$.

NMR (CDCl$_3$) δ 1.84 (m, 6, CH$_2$), 2.40 (m, 2, CH$_2$), 3.47 (m, 2, CH$_2$), 7.15 (m, 2, ArH), 7.38 (m, 1, ArH), 7.44 (d, J=16 Hz, 1, CH), 7.84 (d, J=16 Hz, 1, CH), 8.12 (S, 1, CH).

PREPARATION 60

3-(2,3-Difluorophenyl)-1-(6,7,8,9-tetrahydro-5H-cyclohept[d]-imidazo[2,1-b]thiazol-3-yl)-1-propanone (Formula N-6, X=2,3-difluoro). Refer to Chart N.

3-(2,3-Difluorophenyl)-1-(6,7,8,9-tetrahydro-5H-cyclohept[d]-imidazo[2,1-b]thiazol-3-yl)-2-propene-1-one (Formula N-5, X=2,3-difluoro) was reduced with NaHTe according to non-critical variations in PREPARATION 49 to provide 0.25 g of 3-(2,3-Difluorophenyl)-1-(6,7,8,9-tetrahydro-5H-cyclohept[d]-imidazo[2,1-b]thiazol-3-yl)-1-propanone, m.p. 108–110°, Formula N-6, X=2,3-difluoro).

MS m/z 360 (M$^+$), 341, 313, 247, 233, 219, 193, 192, and 127.

NMR (CDCl$_3$) δ 1.81 (m, 6, CH$_2$), 2.76 (m, 2, CH$_2$), 3.14 (m, 4, CH$_2$), 3.45 (m, 2, CH), 7.0 (m, 3, ArH), 7.99 (S, 1, CH).

EXAMPLE 34

α-[2-(2,3-Difluorophenyl)ethyl]-6,7,8,9-tetrahydro-5H-cyclohept[d]imidazothiazol-3-methanol (Formula N-7, X=2,3-difluoro). Refer to Chart N.

3-(2,3-Difluorophenyl)-1-(6,7,8,9-tetrahydro-5H-cyclohept[d]-imidazo[2,1-b]thiazol-3-yl)-1-propanone (Formula N-6, X=2,3-difluoro), 0.15 g, was reduced with NaBH$_4$ according to non-critical variations in EXAMPLE 12 to produce α-[2-(2,3-Difluorophenyl)ethyl]-6,7,8,9-tetrahydro-5H-cyclohept[d]imidazothiazol-3-methanol (Formula N-7, X=2,3-difluoro), m.p. 158–159°.

Anal. Calcd for C$_{19}$H$_{20}$FN$_2$OS. C, 62.96; H, 5.56; N, 7.73; S, 8.85. Found: C, 62.55; H, 5.58; N, 7.54; S, 8.62.

MS m/z 362 (M$^+$), 344, 313, 231, 221, 205, 193, and 165.

IR (mull) 3199, 3130, 1490, 1481, 1445, 1311, 1283, and 1276 cm$^{-1}$. NMR (CDCl$_3$) δ 1.81 (m, 6, CH$_2$), 2.26 (m, 2, CH$_2$), 2.4–3.1 (m, 5, CH$_2$), 3.32 (m, 1, CH$_2$), 4.92 (t, 1, CH), 6.90–7.12 (m, 4, ArH, CH).

PREPARATION 61

3-(4-Methoxyphenyl)-1-(6,7,8,9-tetrahydro-5H-cyclohept[d]imidazo[2,1-b]thiazol-3-yl)-2-propene-1-one (Formula N-5, X=4-methoxy). Refer to Chart N.

1-(6,7,8,9-tetrahydro-5H-cyclohept[d]imidazo[2,1-b]thiazol-3-yl)-ethanone (Formula N-4), 0.44 g, and anisaldehyde (0.5 mL) were condensed according to non-critical variations in PREPARATION 15 to produce 3-(4-Methoxyphenyl)-1-(6,7,8,9-tetrahydro-5H-cyclohept[d]imidazo[2,1-b]thiazol-3-yl)-2-propene-1-one, 0.65 g, (Formula N-5, X=4-methoxy), m.p. 180–187°.

Anal. Calcd for C$_{20}$H$_{20}$N$_2$O$_2$S. C, 68.16; H, 5.72; N, 7.95; S, 9.10. Found: C, 67.87; H, 5.81; N, 8.10; S, 8.94.

MS m/z 352 (M$^+$), 337, 323, 309, 281, 231, 218, 190, 161, 133, and 121.

IR (mull) 1649, 1588, 1574, 1511, 1421, 1360, 1250, 1180, 1168 and 1033 cm$^{-1}$.

NMR (CDCl$_3$) δ 1.81 (m, 6, CH$_2$), 2.76 (m, 2, CH$_2$), 3.43 (m, 2, CH$_2$). 3.86 (S, 3, OCH$_3$), 6.93 (d, J=9 Hz, 2, ArH), 7.18 (d, J=16 Hz, 1, CH), 7.57 (d, J=9 Hz, 2, ArH), 7.75 (d, J=16 Hz, 1, CH), 8.07 (S, 1, CH)

PREPARATION 62

3-(4-Methoxyphenyl)-1-(6,7,8,9-tetrahydro-5H-cyclohept[d]imidazo[2,1-b]thiazol-3-yl)-1-propanone (Formula N-3, X=4-methoxy). Refer to Chart N.

3-(4-Methoxyphenyl)-1-(6,7,8,9-tetrahydro-5H-cyclohept[d]imidazo[2,1-b]thiazol-3-yl)-2-propene-1-one, 0.18 g, (Formula N-5, X=4-methoxy) was reduced with NaHTe using non-critical variations of PREPARATION 49 to yield pure 3-(4-Methoxyphenyl)-1-(6,7,8,9-tetrahydro-5H-cyclohept[d]imidazo[2,1-b]thiazol-3-yl)-1-propanone, (0.15 g), m.p., 94–96°, (Formula N-6, X=4-methoxy).

Anal. Calcd for C$_{20}$H$_{22}$N$_2$O$_2$S. C, 67.77; H, 6.26; N, 7.90; S, 9.05. Found: C, 67.42; H, 6.38; N, 7.78; S, 9.01.

MS m/z 354 (M$^+$), 247, 233, 219, 192, 134, and 121.

IR (mull) 1663, 1513, 1426, 1303, 1267, 1246, 1195, 1181, 1032, and 824 cm$^{-1}$.

NMR (CDCl$_3$) δ 1.81 (m, 6, CH$_2$), 2.77 (m, 2, CH$_2$), 3.02 (m, 2, CH$_2$), 3.12 (m, 2, CH$_2$), 3.40 (m, 2, CH$_2$), 3.79 (S, 3, OCH$_3$), 6.83 (d, J=9 Hz, 2, ArH), 7.15 (d, J=9 Hz, 2, ArH), 7.98 (S, 1, CH).

EXAMPLE 35

α-[2-(4-methoxyphenyl)ethyl]-6,7,8,9-tetrahydro-5H-cyclohept-[d]imidazo[2,1-b]thiazol-3-methanol (Formula N-7, X=4-methoxy). Refer to Chart N.

3-(4-Methoxyphenyl)-1-(6,7,8,9-tetrahydro-5H-cyclohept[d]imidazo[2,1-b]thiazol-3-yl)-1-propanone (Formula N-6, X=4-methoxy), (0.12 g), was reduced with NaBH$_4$ by non-critical variations of EXAMPLE 12 to give α-[2-(2,3-methoxyphenyl)ethyl]-6,7,8,9-tetrahydro-5H-cyclohept[d]imidazothiazol-3-methanol (Formula N-7, X=4-methoxy), 0.09 g, m.p. 124–125°, after crystallization from acetonitrile solution.

Anal. Calcd for C$_{20}$H$_{24}$N$_2$O$_2$S. C, 67.39; H, 6.79; N, 7.86; S, 9.00. Found: C, 67.19; H, 6.76; N, 7.79; S, 9.04.

MS m/z 356 (M$^+$), 329, 221, 205, 193, 165, 150, and 121.

IR (mull) 3190, 3137, 1513, 1274, 1180, 1072, 1040, and 822 cm$^{-1}$.

NMR (CDCl$_3$) δ 1.82 (m, 6, CH$_2$), 2.33 (m, 2, CH$_2$), 2.63–3.02 (m, 5, CH$_2$), 3.30 (m, 1, CH$_2$), 3.80 (S, 3, CH$_3$O), 6.86 (d, J=9 Hz, 2, ArH), 7.12 (d, J=9 Hz, 2, ArH), 7.26 (S, 1, CH).

EXAMPLE 36

α-[2-(4-Methoxyphenyl)ethenyl]-6,7,8,9-tetrahydro-5H-cyclohept-[d]imidazo[2,1-b]thiazol-3-methanol (Formula N-8, X=4-methoxy). Refer to Chart N.

3-(4-Methoxyphenyl)-1-(6,7,8,9-tetrahydro-5H-cyclohept-[d]imidazothiazol-3-yl)-2-propene-1-one (Formula N-5, X=4-methoxy) was reduced with NaBH$_4$ by non-critical variations of EXAMPLE 22 to provide α-[2-(4-Methoxyphenyl)ethenyl]-6,7,8,9-tetrahydro-5H-cyclohept-[d]imidazo[2,1-b]thiazol-3-methanol (Formula N-8, X=4-methoxy), 0.15 g, m.p. 188–189°.

Anal. Calcd for C$_{20}$H$_{22}$N$_2$OS. C, 67.77; H, 6.23; N, 7.90; S, 9.05. Found: C, 67.47; H, 6.23; N, 7.81; S, 9.11.

MS m/z 354 (M$^+$), 337, 325, 247, 246, 233, 220, 205, 192, 187, 134, and 121.

IR (mull) 3132, 3119, 3071, 1609, 1511, 1447, 1437, 1315, 1302, 1300, 1274, 1251, 1180, 1174, 1145, 1094, and 1033 cm$^{-1}$.

NMR (CDCl$_3$) δ 1.82 (m, 6, CH$_2$), 2.71 (m, 2, CH$_2$), 3.10 (m, 1, CH$_2$), 3.36 (M, 1, CH$_2$), 3.83 (S, 3, OCH$_3$), 5.65 (d,

1, CH), 6.41 (q, 1, CH), 6.67 (d, 1, CH), 6.88 (d, J=9 Hz, 1, ArH), 7.36 (d, J=9 Hz, 1, ArH).

PREPARATION 63

3-(2-Napthalenyl)-1-(6,7,8,9-tetrahydro-5H-cyclohept[d]imidazo[2,1-b]thiazol-3-yl)-2-propene-1-one (Formula O-2). Refer to Chart O.

1-(6,7,8,9-tetrahydro-5H-cyclohept[d]imidazo[2,1-b]thiazol-3-yl)ethanone (Formula O-1), 1.37 g, was condensed with 2-napthaldehyde by non-critical variations of EXAMPLE 15 to yield 3-(2-Napthalenyl)-1-(6,7,8,9-tetrahydro-5H-cyclohept[d]imidazo[2,1-b]thiazol-3-yl)-2-propene-1-one (Formula O-2), 2.24 g, m.p. 185–188°.

Anal. Calcd for $C_{23}H_{20}N_2OS$. C, 74.16; H, 5.41; N, 7.52; S, 8.61. Found: C, 73.81; H, 5.47; N, 7.54; S, 8.58.

MS m/z 372 (M$^+$), 355, 343, 315, 245, 231, 152 and 142.

IR (mull) 3096, 3066, 3056, 3036, 3008, 1650, 1600, 1586, 1421, 1367, 1346, 1301, 1269, and 1197 cm$^{-1}$.

PREPARATION 64

3-(2-Napthalenyl)-1-(6,7,8,9-tetrahydro-5H-cyclohept[d]imidazo[2,1-b]thiazol-3-yl)-1-propanone (Formula O-3, X=H). Refer to Chart O.

2-Napthalenyl-1-(6,7,8,9-tetrahydro-5H-cyclohept[d]imidazo[2,1-b]thiazol-3-yl)-2-propene-1-one (Formula O-2, X=H), 0.74 g, was reduced according to non-critical variation in PREPARATION 49 to provide 3-(2-Napthalenyl)-1-(6,7,8,9-tetrahydro-5H-cyclohept[d]imidazo[2,1-b]thiazol-3-yl)-1-propanone (Formula O-3), m.p. 76–78° after acetonitrile crystallization of the silica gel eluted product.

Anal. Calcd for $C_{23}H_{22}N_2OS$. C, 73.77; H, 5.92; N, 7.48; S, 8.56. Found: C, 73.72; H, 6.14; N, 7.40; S, 8.51.

MS m/z 374 (M$^+$), 247, 233, 219, 192, 154, and 141.

IR (mull) 3318, 3105, 3055, 3018, 1667, 1500, 1426, 1356, 1310, 1184, and 1175 cm$^{-1}$.

NMR (CDCl$_3$) δ 1.80 (m, 6, CH$_2$), 2.75 (m, 2, CH$_2$), 3.23 (m, 4, CH$_2$), 3.42 (m, 2, CH$_2$), 7.45 (m, 3, ArH), 7.67 (S, 1, ArH), 7.78 (m, 3, ArH), 8.00 (S, 1, CH).

EXAMPLE 37

α-[2-(2-Naphthalenyl)ethyl]-6,7,8,9-tetrahydro-5H-cyclohept[d]imidazo[2,1-b]thiazol-3-methanol (Formula O-4). Refer to Chart O.

3-(2-Napthalenyl)-1-(6,7,8,9-tetrahydro-5H-cyclohept[d]imidazo[2,1-b]thiazol-3-yl)-1-propanone (Formula O-3), 0.10 g, was reduced with NaBH$_4$ by non-critical variations of EXAMPLE 12 to yield pure α-[2-(2- Naphthalenyl)ethyl]-6,7,8,9-tetrahydro-5H-cyclohept[d]imidazo[2,1-b]thiazol-3-methanol (Formula O-4, X=H), m.p. 124–127°.

Anal. Calcd for $C_{23}H_{24}N_2OS$. C, 73.37; H, 6.42; N, 7.44; S, 8.52. Found: C, 72.43; H, 6.62; N, 7.50; S, 8.36.

MS m/z 376 (M$^+$), 349, 332, 235, 234, 221, 193 and 141.

IR (mull) 3201, 3140, 3121, 1631, 1608, 1599, 1446, 1431, 1310, 1280, 1271, 1163, and 1151 cm$^{-1}$.

NMR (CDCl$_3$) δ 1.75 (m, 6, CH$_2$), 2.34 (m, 2, CH$_2$), 2.65 (m, 2, CH$_2$), 2.80–3.15 (m, 3, CH$_2$), 3.28 (m, 1, CH$_2$), 4.90 (t, 1, CH), 7.05 (S, 1, CH), 7.3–7.5 (m, 3, ArH), 7.64 (S, 1, ArH), 7.78 (m, 3, ArH).

PREPARATION 65

3-(2-Furanyl)-1-(6,7,8,9-tetrahydro-5H-cyclohept[d]imidazo[2,1-b]thiazol-3-yl)-2-propene-1-one (Formula P-2, X=0). Refer to Chart P.

3-(3-Furanyl)-1-(6,7,8,9-tetrahydro-5H-cyclohept[d]imidazo[2,1-b]thiazol-3-yl)-ethanone (Formula P-1), 3.51 g, was condensed with 2-Furaldehyde (1.99 g) by non-critical variations of PREPARATION 15 to give 3-(2-Furanyl)-1-(6,7,8,9-tetrahydro-5H-cyclohept[d]imidazo[2,1-b]thiazol-3-yl)-2-propene-1-one (Formula P-2, X=0), m.p. 161–162°.

Anal. Calcd for $C_{17}H_{16}N_2O_2S$. C, 65.36; H, 5.16; N, 8.97; S, 10.26. Found: C, 65.26; H, 5.17; N, 8.98; S, 10.20.

MS m/z 312, 295, 284, 283, 269, 255, 231, 218, 203, and 190.

IR (mull) 3126, 3114, 3011, 1653, 1598, 1557, 1551, 1497, 1354, 1349, 1303, 1292, 1267, 1203, and 1018 cm$^-$.

NMR (CDCl$_3$) 1.86 (m, 6, CH$_2$), 2.78 (m, 2, CH$_2$), 3.46 (m, 2, CH$_2$), 6.51 (q, 1, CH), 5.67 (d, J=3.5 Hz, 1, CH), 7.23 (d, J=15 Hz, 1, CH), 7.53 (d, 1, CH), 7.55 (d, J=15 Hz, 1, CH).

EXAMPLE 38

α-[2-(2-Furanyl)ethenyl]-6,7,8,9-tetrahydro-5H-cyclohept[d]imidazo[2,1-b]thiazol-3-methanol (Formula P-4, X=0). Refer to Chart P.

3-(2-Furanyl)-1-(6,7,8,9-tetrahydro-5H-cyclohept[d]imidazo[2,1-b]thiazol-3-yl-2-propene-1-one (Formula P-2, X=0), 0.20 g, was reduced by non-critical variations of EXAMPLE 22 to yield a α-[2-(2-Furanyl)ethenyl]-6,7,8,9-tetrahydro-5H-cyclohept[d]imidazo[2,1-b]thiazol-3-methanol (Formula P-4, X=0), 0.15 g, m.p. 177–180° after crystallization from isopropanol solution.

Anal. Calcd for $C_{17}H_{18}N_2O_2S$. C, 64.94; H, 5.77; N, 8.91; S, 10.20. Found: C, 64.89; H, 5.94; N, 8.88; S, 10.99.

MS m/z 314 (M$^+$), 297, 285, 269, 257, 233, 221, 219, 193, 192, 179, and 147.

IR (mull) 3112, 3099, 1610, 1543, 1489, 1446, 1439, 1322, 1311, 1276, 1147, 1097, and 1012 cm$^{-1}$.

NMR (CDCl$_3$) δ 1.79 (m, 6, CH$_2$), 2.68 (m, 2, CH$_2$), 3.07 (m, 1, CH$_2$), 3.35 (m, 1, CH$_2$), 3.62 (b, 1, OH), 5.63 (d, J–4.4 Hz, 1, CH), 6.27 (d, J=3.3 Hz, 1, CH), 6.39 (q, 1, CH), 6.44 (q, J=4.4 Hz, J=16 Hz, 1, CH), 6.57 (d, J=16 Hz, 1, CH), 6.95 (S, 1, CH), 7.38 (d, 1, CH).

EXAMPLE 39

α-[2-(2-Furanyl)ethyl]-6,7,8,9-tetrahydro-5H-cyclohept[d]imidazo[2,1-b]thiazol-3-methanol (Formula P-5, X=0). Refer to Chart P.

3-(2-Furanyl)-1-(6,7,8,9-tetrahydro-5H-cyclohept[d]imidazo[2,1-b]thiazol-3-yl)-propene-1-one (Formula P-2, X=0), 0.94 g, was reduced with LiAlH$_4$ by non-critical variations of EXAMPLE 23 to provide α-[2-(2-Furanyl)ethyl]-6,7,8,9-tetrahydro-5H-cyclohept[d]imidazo[2,1-b]thiazol-3-methanol (Formula P-5, X=0), after two crystallizations from ethanol.

Anal. Calcd for $C_{17}H_{20}N_2O_2S$. C, 64.53; H, 6.37; N, 8.85; S, 10.13. Found: C, 64.56; H, 6.20; N, 8.81; S, 10.14.

MS m/z 316 (M$^+$), 299, 297, 287, 285, 269, 221, 205, and 193.

IR (mull) 3186, 3139, 3118, 1610, 1599, 1506, 1434, 1316, 1277, and 1160 cm$^{-1}$.

NMR (CDCl$_3$) δ 1.80 (m, 6, CH$_2$), 2.28 (M, 2, CH$_2$), 2.50–2.80 (m, 4, CH$_2$), 2.75–3.05 (m, 3, CH$_2$), 3.30 (m, 1, CH$_2$), 4.90 (m, 1, CH), 6.05 (m, 1, CH), 6.29 (m, 1, CH), 7.40 (S, 1, CH), 7.26 (d, 1, CH).

PREPARATION 66

3-(3-Furanyl)-1-(6,7,8,9-tetrahydro-5H-cyclohept[d]imidazo[2,1-b]thiazol-3-yl)-2-propene-1-one (Formula P-2, X=0). Refer to Chart P.

1-(6,7,8,9-Tetrahydro-5H-cyclohept[d]imidazo[2,1-b]thiazol-3-yl)-ethanone (Formula P-1), 1.87 g, was reacted with 3-furaldehyde (0.73 mL) by non-critical variations of PREPARATION 15 to give 3-(3-Furanyl)ethyl]-6,7,8,9-tetrahydro-5H-cyclohept[d]imidazo[2,1-b]thiazol-3-yl)-propene-1-one (Formula P-2, X=O), 1.74 g, m.p. 168–170°, after crystallization from acetonitrile solution.

Anal. Calcd for $C_{17}H_{16}N_2O_2S$. C, 65.36; H, 5.16; N, 8.97; S, 10.26. Found: C, 65.19; H, 5.21; N, 9.03; S, 10.17.

MS m/z 312 (M+), 295, 283, 269, 267, 255, 231, 193, and 121.

IR (mull) 3445, 3142, 3108, 3096, 1654, 1600, 1506, 1448, 1422, 1359, 1304, 1271, 1203, and 1161 cm$^{-1}$.

NMR (CDCl$_3$) δ 1.86 (m, 6, CH$_2$), 2.78 (m, 2, CH$_2$), 3.44 (m, 2, CH$_2$), 6.71 (d, 1, CH), 7.02 (d, J=16 Hz, 1, CH), 7.48 (d, 1, CH), 7.66 (d, J=16 Hz, 1, CH), 7.71 (S, 1, CH), 8.06 (S, 1, CH).

PREPARATION 67

3-(3-Furanyl)ethyl]-6,7,8,9-tetrahydro-5H-cyclohept[d]imidazo[2,1-b]thiazol-3-yl)-1-propanone (Formula P-3, X=O). Refer to Chart P.

3-(3-Furanyl)ethyl]-6,7,8,9-tetrahydro-5H-cyclohept[d]imidazo[2,1-b]thiazol-3-yl)-2-propene-1-one (Formula P-2, X=O), (0.31 g) was reduced by non-critical variations of PREPARATION 49 to produce 3-(3-Furanyl)ethyl]-6,7,8,9-tetrahydro-5H-cyclohept[d]imidazo[2,1-b]thiazol-3-yl)-1-propanone (Formula P-3, X=O), 0.24 g, m.p. 111–114°.

Anal. Calcd for $C_{17}H_{18}N_2O_2S$. C, 64.94; H, 5.77; N, 8.91; S, 10.20. Found: C, 64.98; H, 5.82; N, 8.89; S, 10.12.

MS m/z 314 (M+), 297, 286, 285, 271, 257, 219, 205, and 192.

IR (mull) 3308, 3176, 3139, 3121, 3098, 1665, 1509, 1446, 1424, 1410, 1305, 1204, 1199, and 1026 cm$^{-1}$.

NMR (CDCl$_3$) δ 1.81 (m, 6, CH$_2$), 2.72 (m, 2, CH$_2$), 2.90 (m, 2, CH$_2$), 3.06 (m, 2, CH$_2$), 3.40 (m, 2, CH$_2$, 6.30 (d, 1, CH), 7.26 (d, 1, CH), 7.35 (S, 1, CH), 8.00 (S, 1, CH).

EXAMPLE 40

α-[2-(3-Furanyl)ethyl]-6,7,8,9-tetrahydro-5H-cyclohept[d]imidazo[2,1-b]thiazol-3-methanol (Formula P-5, X=O). Refer to Chart P.

3-(3-Furanyl)-1-(6,7,8,9-tetrahydro-5H-cyclohept[d]imidazo[2,1-b]thiazol-3-yl-1-propanone (Formula P-3, X=O), 0.115 g, was reduced with NaBH$_4$ by non-critical variations in EXAMPLE 12 to yield α-[2-(3-Furanyl)ethyl]-6,7,8,9-tetrahydro-5H-cyclohept[d]imidazo[2,1-b]thiazol-3-methanol (Formula P-5, X=O), m.p. 153–155°.

Anal. Calcd for $C_{17}H_{20}N_2O_2S$. C, 64.53; H, 6.37; N, 8.85; S, 10.13. Found: C, 64.22; H, 6.44; N, 8.80; S, 9.93.

MS m/z 316 (M+), 299, 298, 297, 287, 245, 234, 221, 205, 203, and 193.

IR (mull) 3190, 3134, 1501, 1445, 1367, 1315, 1278, 1162, 1155, 1070, and 1021 cm$^{-1}$.

NMR (CDCl$_3$) δ 1.82 (m, 6, CH$_2$), 2.20 (m, 2, CH$_2$), 2.67 (m, 4, CH$_2$), 3.0 (m, 1, CH$_2$), 3.30 (m, 1, CH$_2$), 4.90 (t, 1, CH), 6.30 (d, 1, CH), 7.12 (d, 1, CH), 7.26 (S, 1, CH), 7.40 (S, 1, CH).

PREPARATION 68

3-[2-Furanyl]-2,3-dimethylimidazo[2,1-b]thiazol-3-yl]-2-propene-1-one (Formula Q-2, X=O). Refer to Chart Q.

1-(2,3-Dimethylimidazo[2,1-b]thiazol-5-yl]ethanone (Formula Q-1), 2.92 g, was condensed with 2-furaldehyde (2.0 mL) by non-critical variations of PREPARATION 15 to produce 3-[(2-Furanyl)-2,3-dimethylimidazo[2,1-b]thiazol-3-yl]-2-propene-1-one (Formula Q-2, X=O).

NMR (CDCl$_3$) δ 2.37 (S, 3, CH$_3$), 2.67 (S, 3, CH$_3$), 6.51 (m, 1, CH), 6.67 (m, 1, CH), 7.22 (d, J=16 Hz, 1, CH), 7.52 (m, 3, CH), 8.07 (S, 1, CH).

EXAMPLE 41

α-[2-(2-Furanyl)ethenyl]2,3-dimethylimidazo[2,1-b]thiazol-3-methanol (Formula Q-3, X=O). Refer to Chart Q.

3-[(2-Furanyl)-2,3-dimethylimidazo[2,1-b]thiazol-5-yl] 2-propene-1-one (0.20 g), Formula Q-2, X=O), was reduced with NaBH$_4$ by non-critical variations in EXAMPLE 22 to yield α-[2-(2-Furanyl)ethenyl]2,3-dimethylimidazo[2,1-b]thiazol-3-methanol (Formula Q-3, X=O), 0.15 g, m.p. 149–150°.

Anal. Calcd for $C_{14}H_{14}N_2O_2S$. C, 61.29; H, 5.14; N, 10.21; S, 11.69. Found: C, 61.19; H, 5.26; N, 10.20, S, 11.62.

MS m/z 274 (M+), 257, 245, 229, 217, 193, 181, 179, 165, and 152.

IR (mull) 3145, 3115, 3033, 1546, 1451, 1432, 1323, 1298, 1249, 1143, 1096, and 1015 cm$^{-1}$.

NMR (CDCl$_3$) δ 2.29 (S, 3, CH$_3$), 2.56 (S, 3, CH$_3$, 5.65 (d, 1, CH), 6.28 (m, 1, CH), 6.39 (m, 1, CH), 6.45 (q, 1, CH), 6.53 (d, J=16, 1, CH), 6.98 (S, 1, CH), 7.38 (d, 1, CH).

EXAMPLE 42

α-[2-(2-Furanyl)ethyl]2,3-dimethylimidazo[2,1-b]thiazol-3-methanol (Formula Q-4, X=O). Refer to Chart Q.

3-[(2-Furanyl)-2,3-dimethylimidazo[2,1-b]thiazol-3-yl]-2-propene-1-one, Formula Q-2, X=O), 0.272 g, was reduced with LiAlH by non-critical variations of EXAMPLE 22 to provide pure α-[2-(2-Furanyl)ethyl]2,3-dimethylimidazo[2,1-b]thiazol-3-methanol (Formula Q-4, X=O), 0.02 g, m.p. 144–145°.

PREPARATION 69

G1-(2,3-Dimethylimidazo[2,1-b]thiazol-5-yl)-3-hydroxy-3-phenyl-1-propanone (Formula R-3, X=H).

(2,3-Dimethylimidazo[2,1-b]thiazol-5-yl) ethanone, 0.94 g, (Formula R-1) was converted to the t-butyl-dimethylenol silane using dimethyl-tertbutyl chlorosilane (1.10 g) in the procedure described by P. Cazeau et al. (Tetrahedron, 43, 2075 (1987)). The crude enol silane product was purified by silica gel chromatography to yield pure enol silane, 1.0 g, (Formula R-2). Benzaldehyde (0.34 g) in methylene chloride (10 mL) at −78° was treated with BF$_3$ ethereate (0.461 g) in CH$_2$Cl$_2$ (15 mL). After 20 minutes, a solution of enol silane (Formula R-2, 1.0 g) in CH$_2$Cl$_2$ (10 mL) was added dropwise during 30 minutes. After 3 hours reaction, the solution was brought to −10° to −15° and maintained for 18 hours. The reaction solution was quenched into 5% NaHCO$_3$ solution and the residue (0.94 g) from evaporation of the extraction solvent was purified by silica gel chromatography to yield pure 1-(2,3-Dimethylimidazo[2,1-b]thiazol-5-yl)-3-hydroxy-3-phenyl-1-propanone (Formula R-3, X=H), m.p. 113°.

NMR (CDCl$_3$) δ 2.37 (S, 3, CH$_3$), 2.65 (S, 3, CH$_3$), 3.20 (m, 2, CH), 5.40 (m, 1, CH), 7.27–7.50 (m, 5, ArH), 7.96 (S, 1, CH).

EXAMPLE 43

1-(2,3-Dimethylimidazo[2,1-b]thiazol-5-yl)-3-phenyl-1,3-propanediol (Formula R-4, X=H).

1-(2,3-Dimethylimidazo[2,1-b]thiazol-5-yl)-3-hydroxy-3-phenyl-1-propanone (Formula R-3, X=H), 0.08 g, in toluene (10 mL) was treated with 1M diisobutylaluminum hydride (1.0 mL) and reacted for 1.25 hours. The solution was quenched into 5% citric acid, the mixture was extracted with ethyl acetate and the citric acid solution was neutralized with NaOH. Extraction of product from the neutralized solution gave pure 1-(2,3-Dimethylimidazo[2,1-b]thiazol-5-yl)-3-phenyl-1,3-propanediol (Formula R-4, X=H), 0.04 g, m.p. 152–153° after crystallization from $CH_2Cl_2/CH_3CN$ solution.

MS m/z 302 ($M^+$), 284, 267, 207, 195, 181, 165, and 153.

NMR ($CDCl_3$) 2.27 (S, 3, $CH_3$), 2.46 (S, 3, $CH_3$), 5.03–5.35 (m, 2, CH), 7.0 (S, 1, CH), 7.20–7.45 (m, 5, ArH).

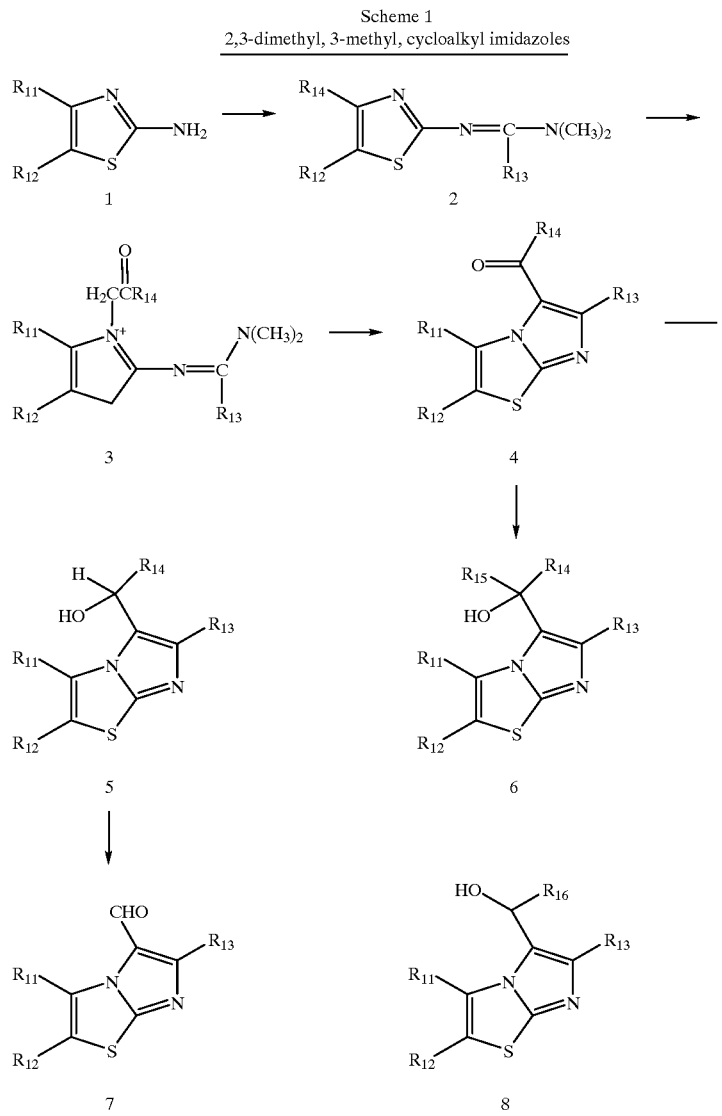

Scheme 1
2,3-dimethyl, 3-methyl, cycloalkyl imidazoles

Substituent Definitions

1: (a) $R_{11} = CH_3$, $R_{12} = H$
   (b) $R_{11}R_{12} = CH_3$
   (c) $R_{11}R_{12} = CH_2CH_2CH_2$—
   (d) $R_{11}R_{12} = CH_2CH_2CH_2CH_2$—
   (e) $R_{11}R_{12} = (CH_2)_5$
   (f) $R_{11}R_{12} = (CH_2)_6$
   (g) $R_{11}R_{12} = H$

2a–2g: $R_{13} = H$, $CH_3$;

3a–3g: $R_{13} = H$, $CH_3$; $R_{14} = OCH_3$, $OCH_2CH_3$, $CH_3$;

4a–4g: $R_{13} = H$, $CH_3$; $R_{14} = OCH_3$, $OCH_2CH_3$, $CH_3$;

-continued 5a-5g: $R_{13}$ = H, $CH_3$; $R_{14}$ = H, $CH_3$;

6a-6g: $R_{13}$ = H, $CH_3$; $R_{14}$ = $CH_3$;
$R_{15}$ = $(CH_2)_n C_6 H_4 X$ (n = 1–4)
X = H, Cl, Br, F, $OCH_3$ and occupy either ortho, meta, or parapositions 7a-7g: $R_{13}$ = H, $CH_3$;

8a-8g: $R_{13}$ = H, $CH_3$; $R_{16}$ = $(CH_2)_n C_6 H_5$ (n = 1–4)

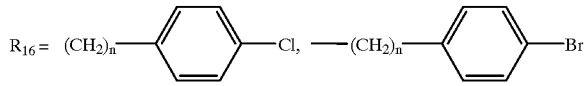

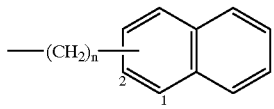

(where the —$(CH_2)_n$— sidechain is attached at the 1- or 2-position of the naphthalene ring)

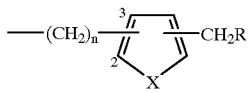

(X = O, S, NH, $NCH_3$), R = H, $CH_3$, n = 0–3, and where the —$(CH_2)_n$— sidechain is attached at the 2- or 3-position of the heterocyclic ring)

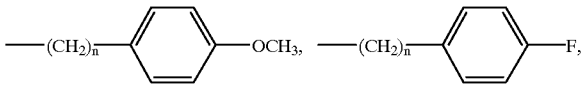

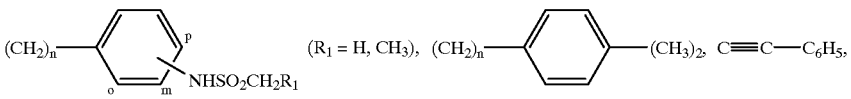

($R_1$ = H, $CH_3$), 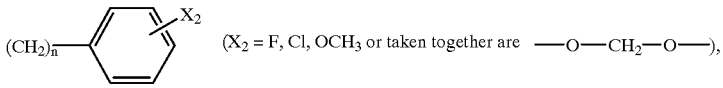

($X_2$ = F, Cl, $OCH_3$ or taken together are —O—$CH_2$—O—),

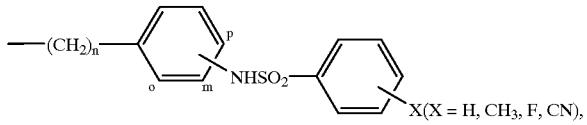

X(X = H, $CH_3$, F, CN),

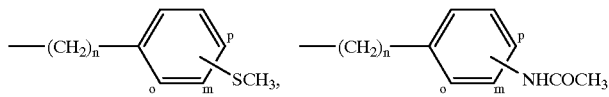

Scheme 2
Elaboration of α-phenylethyl carbinol side chains and allyl sustituents

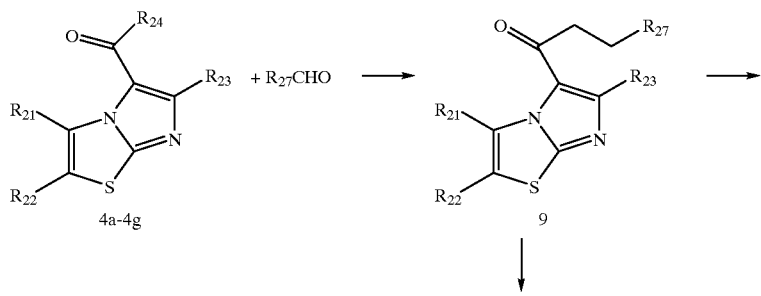

-continued
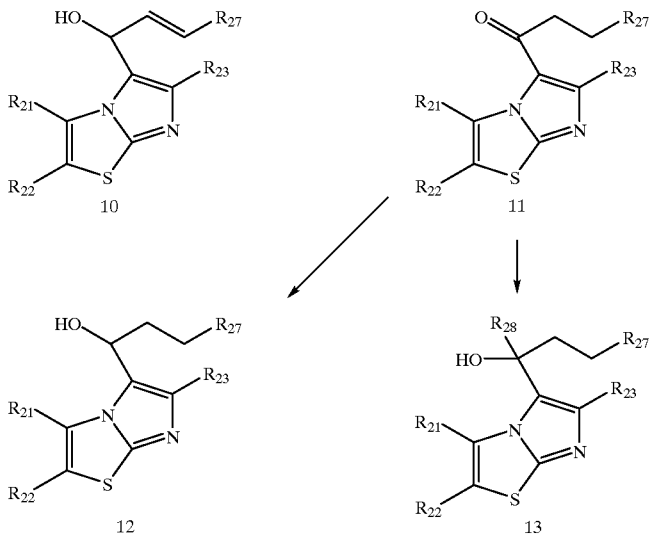
4: (a) $R_{21} = CH_3$, $R_{22} = H$
   (b) $R_{21}R_{22} = CH_3$
   (c) $R_{21}R_{22} = CH_2CH_2CH_2$—
   (d) $R_{21}R_{22} = CH_2CH_2CH_2CH_2$—
   (e) $R_{21}R_{22} = (CH_2)_5$
   (f) $R_{21}R_{22} = (CH_2)_6$
   (g) $R_{21}R_{22} = H$
9a-9g; 10a-10g; 11a-11g; 12a-12g:   $R_{23} = H$, $CH_3$; $R_{27} = C_6H_5$,
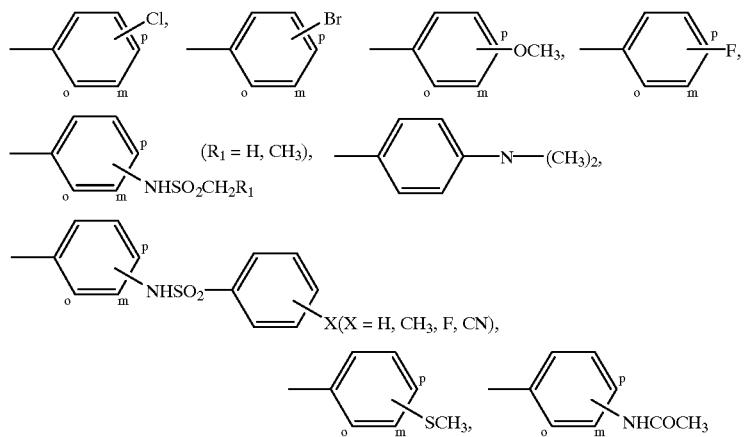
where the aryl substituents occupy the ortho, meta, or para positions.
13a-13g:   $R_{23} = H$, $CH_3$; $R_{28} = CH_3$; $R_{27} = C_6H_5$,
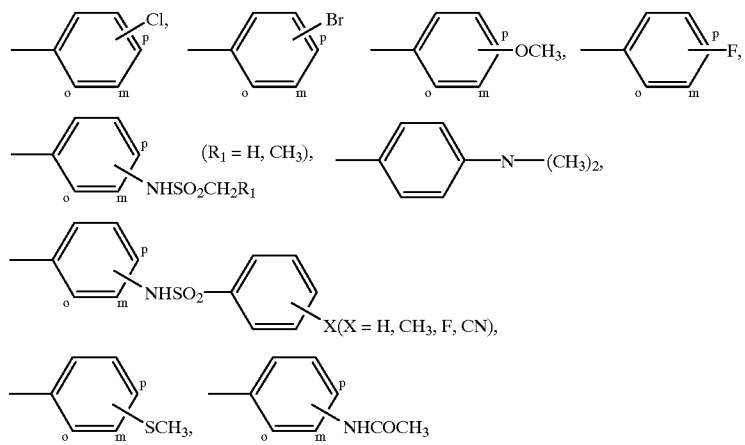

-continued
where the aryl substituents occupy the ortho, meta, or para positions.
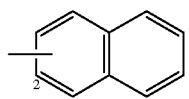
where the ethyl sidechain is attached to the 1- or 2-position of the naphthalene ring.
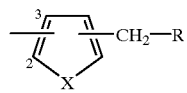
(X = O S, NH, NCH$_3$, R = H, CH$_3$ and the ethyl sidechain is attached at the 2- or 3-position of the heterocyclic ring.
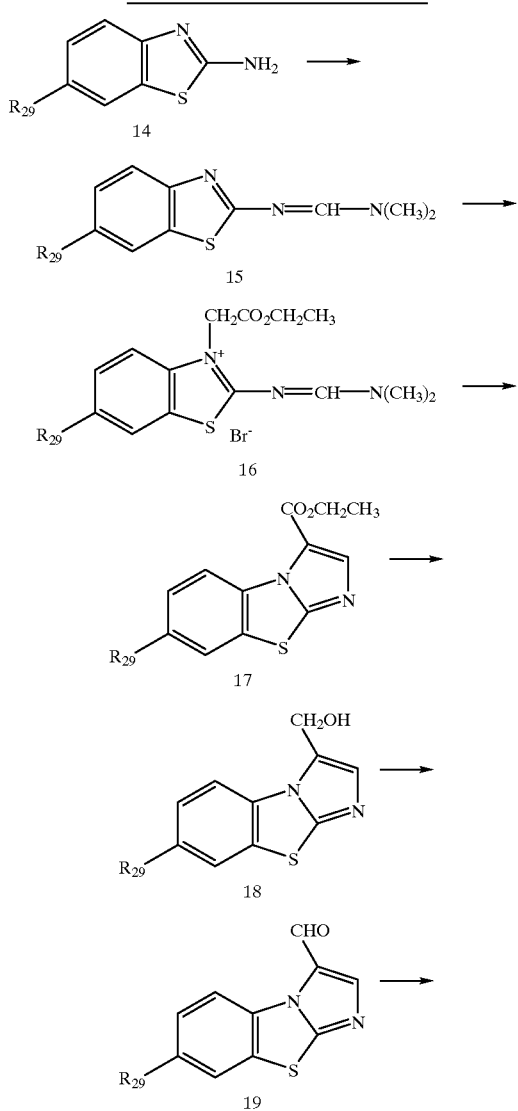
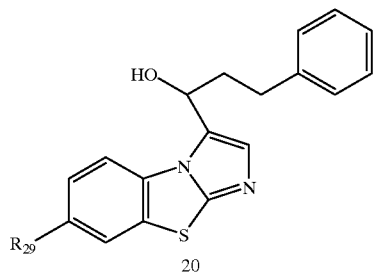
$R_{29}$ = H, CH$_3$, F, OCH$_3$
FORMULA CHART
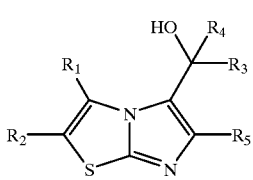
I
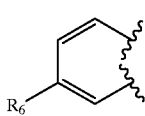
II
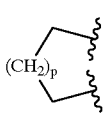
III

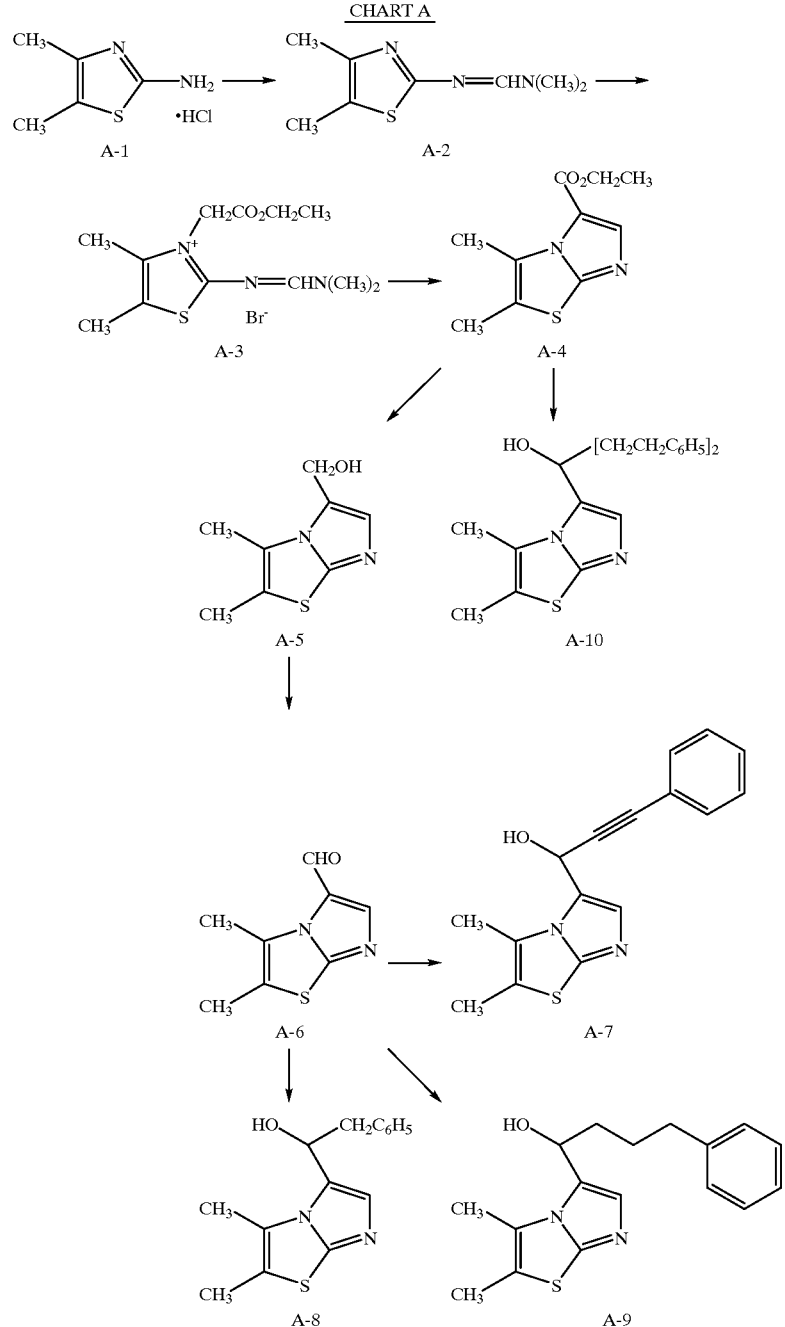
CHART A

CHART B
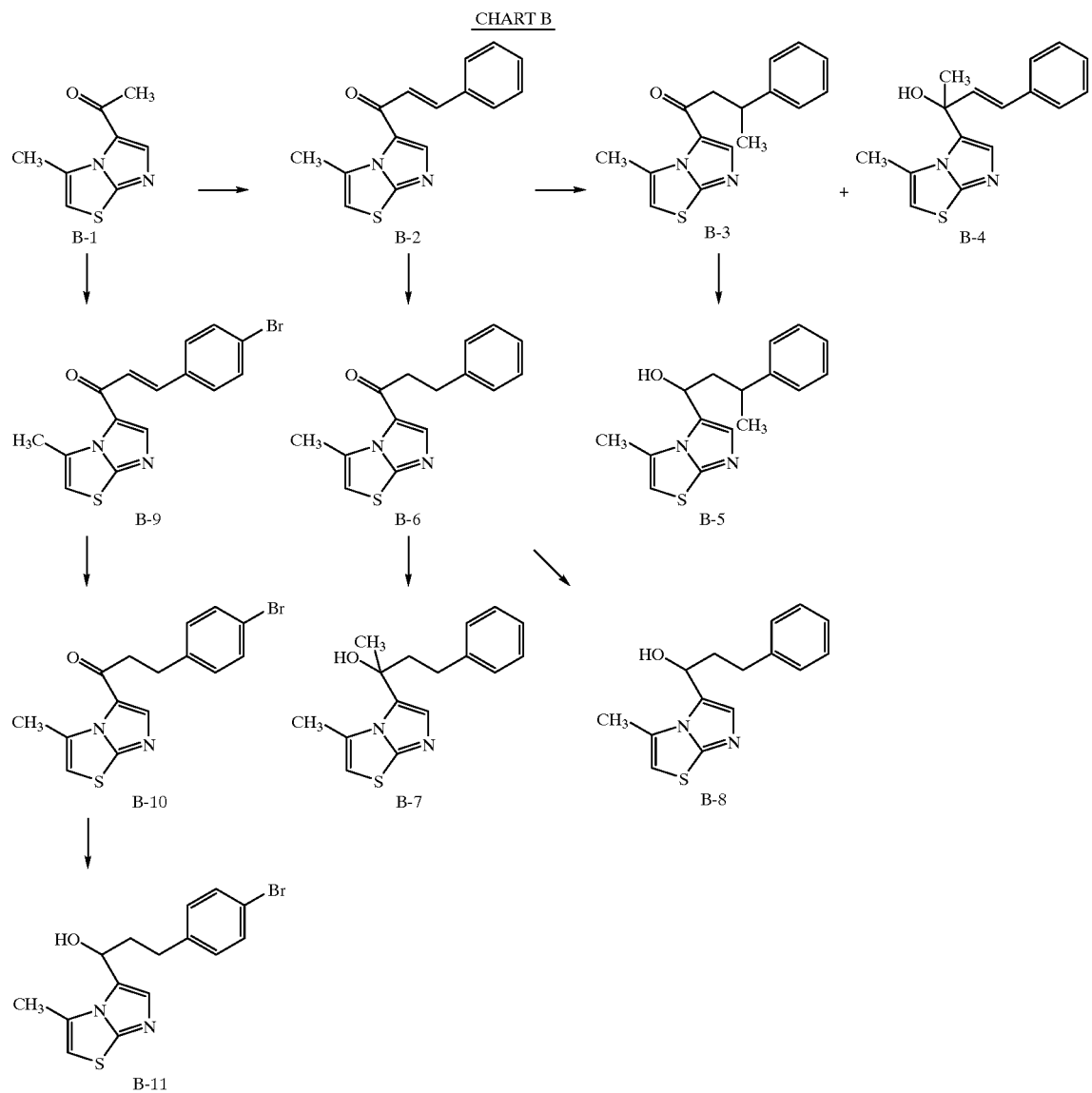
CHART C
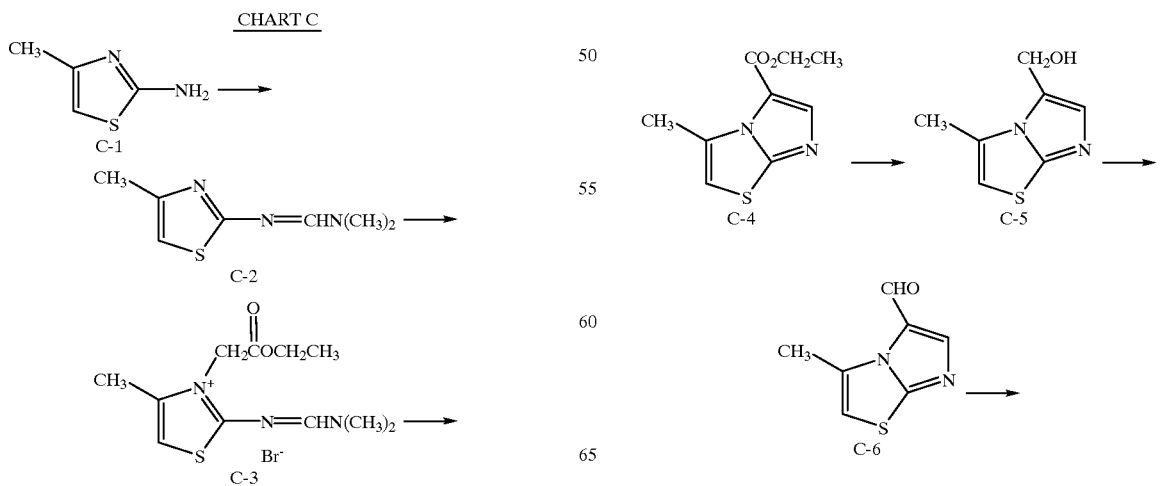

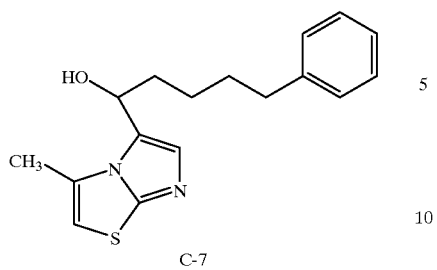
CHART D
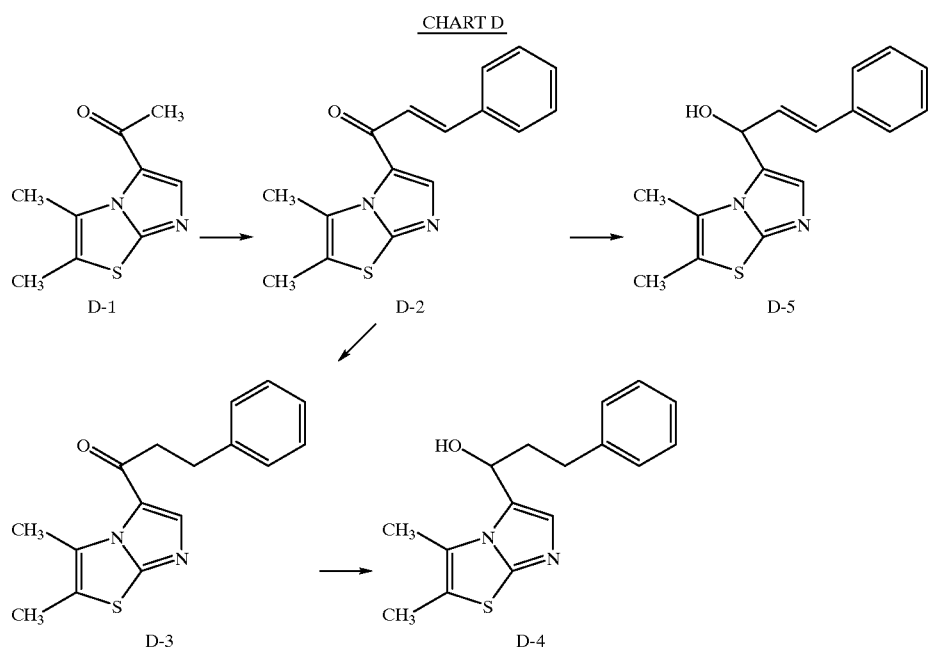
CHART E
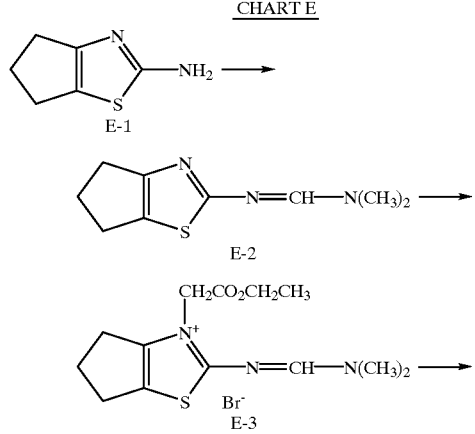
-continued
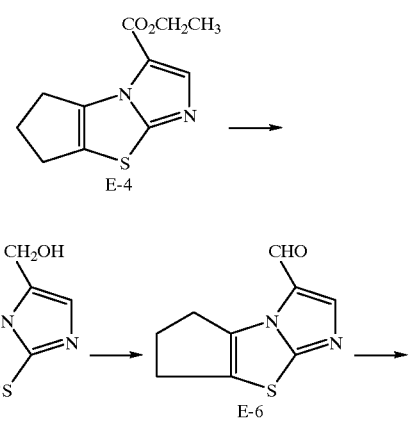

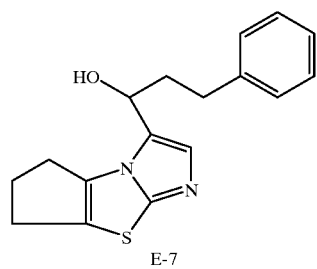
E-7
CHART F
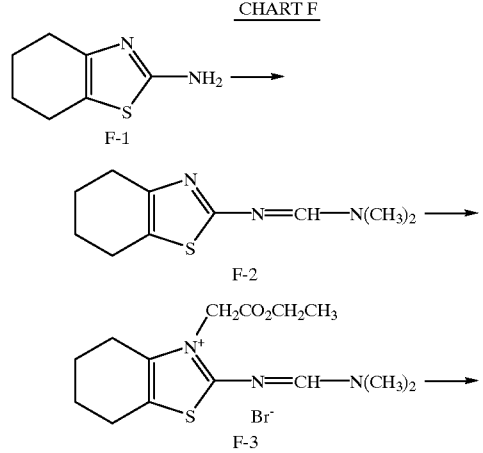
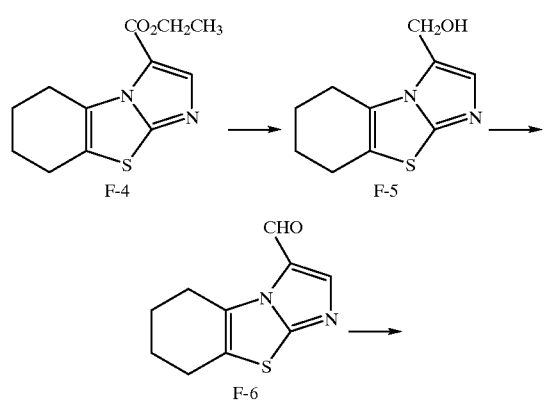
CHART G
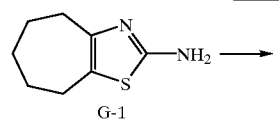
G-1
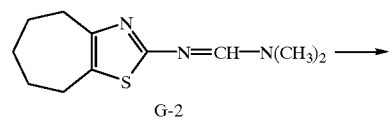
G-2
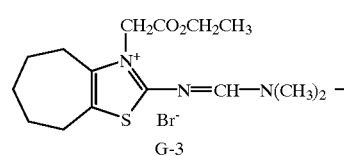
G-3
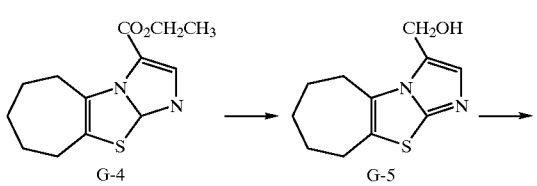
G-4  G-5
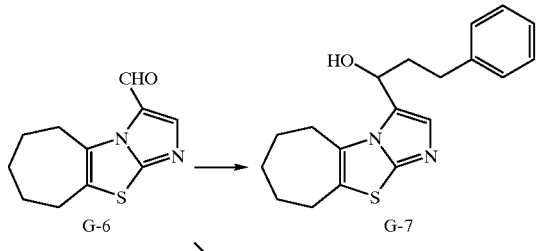
G-6  G-7
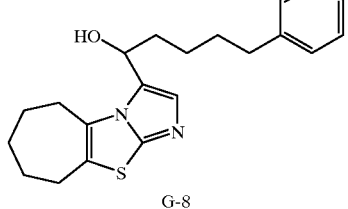
G-8
CHART H
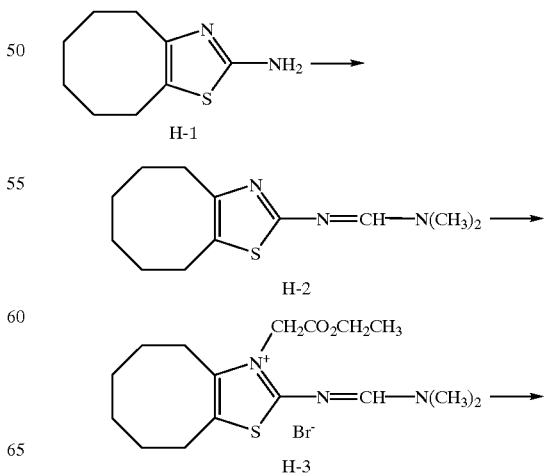

-continued
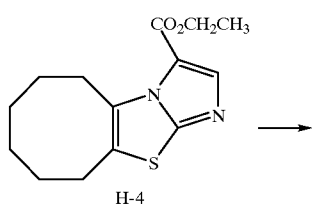
H-4
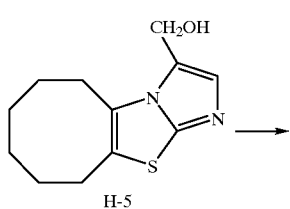
H-5
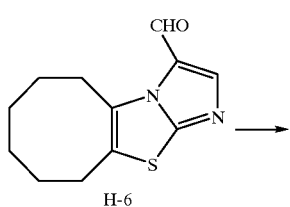
H-6
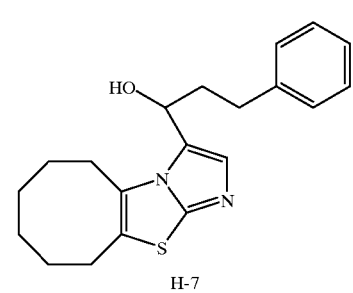
H-7
CHART J
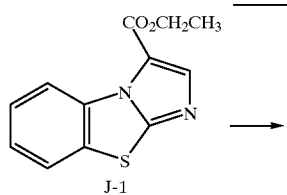
J-1
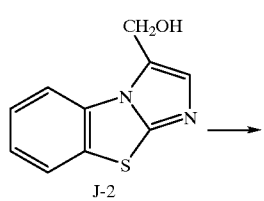
J-2
-continued
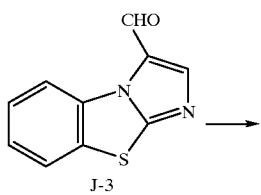
J-3
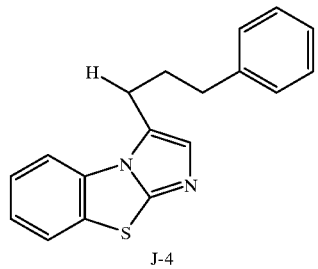
J-4
CHART K
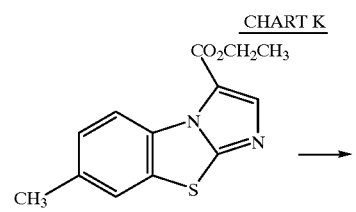
K-1
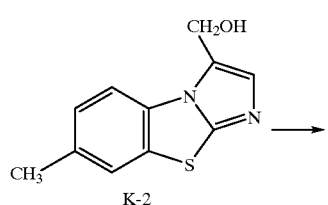
K-2
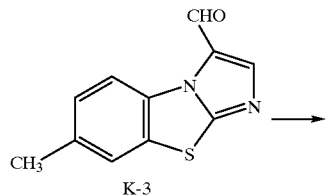
K-3
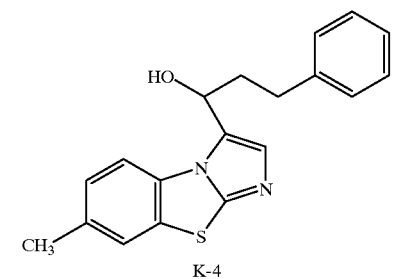
K-4

CHART L
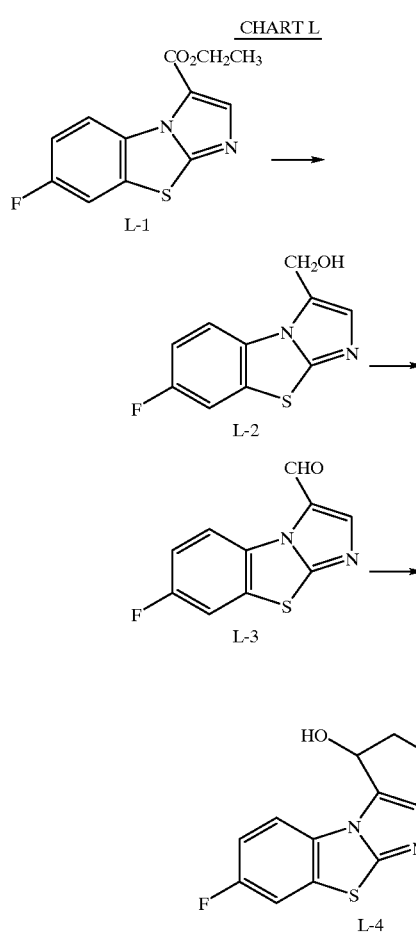
CHART M
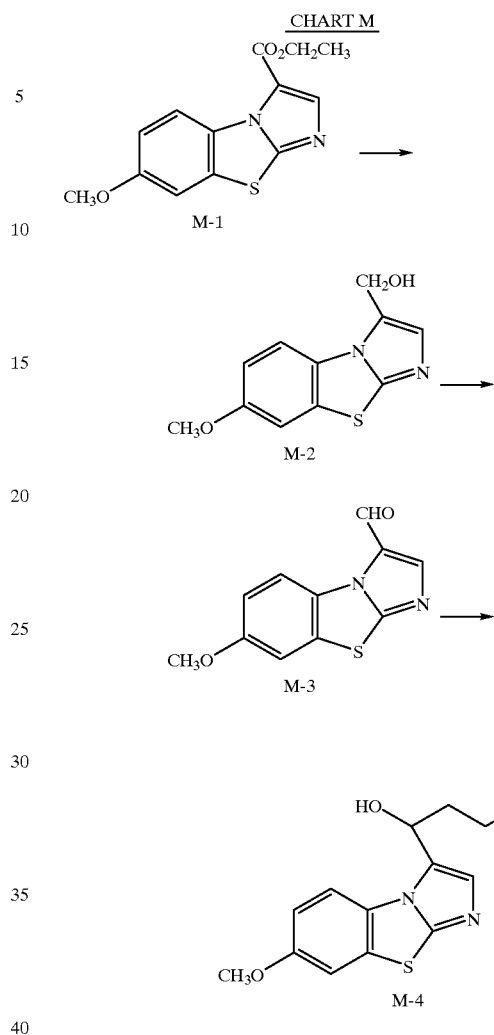
CHART N
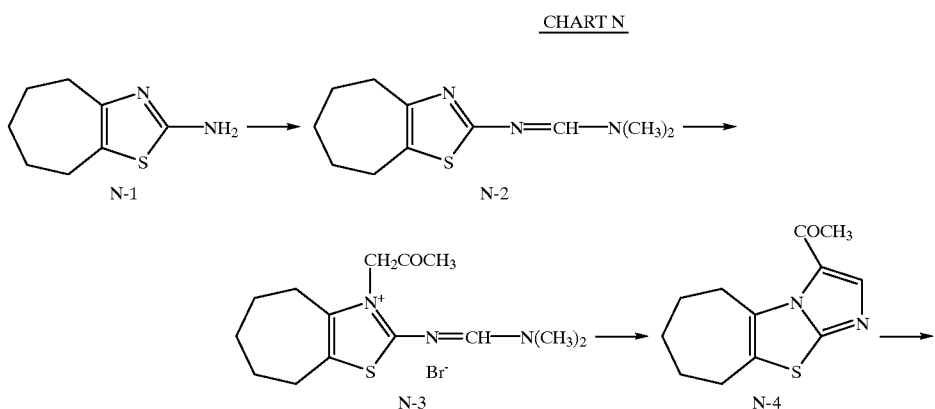

-continued
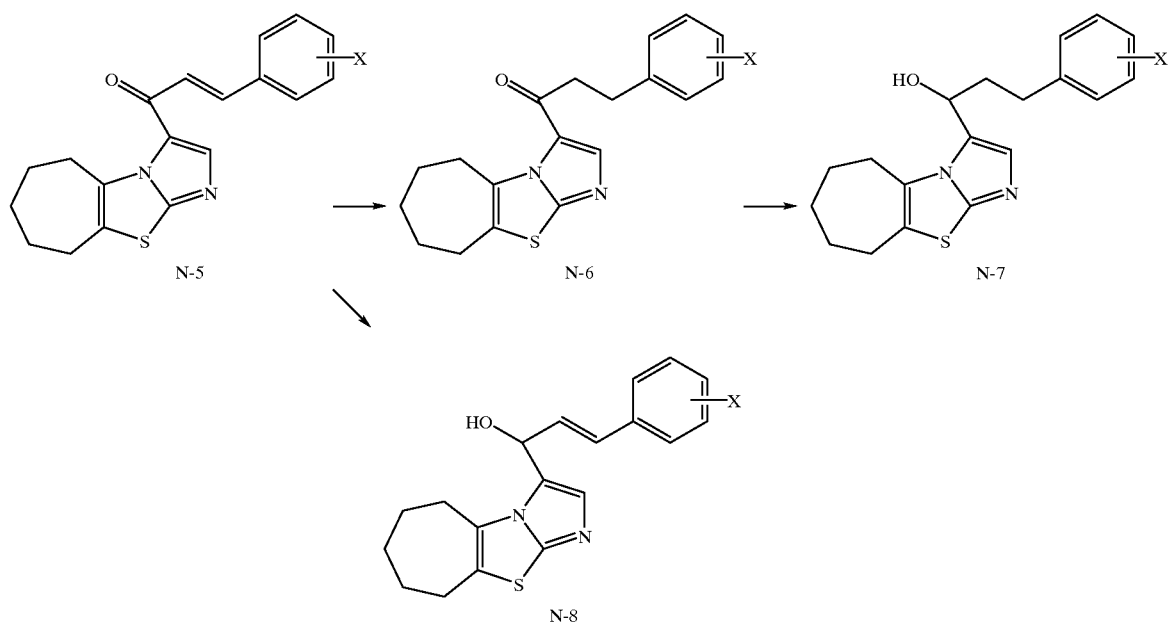
Chart N Substituent Definitions
X = 4-dimethylamino
X = 3,5-difluoro
X = 2,3-difluoro
X = 3-bromo
X = 3-chloro
X = 3-fluoro
X = 4-fluoro
X = 4-methoxy
CHART N'
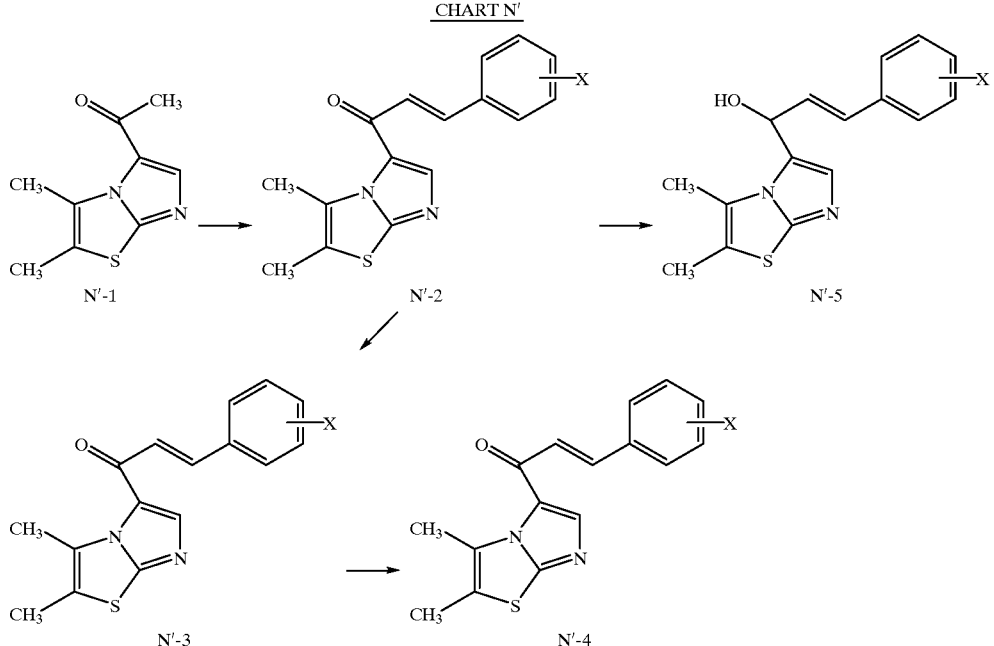
Chart N' Substituent Definitions
X = 2-toluenesulfonamide
X = 3-toluenesulfonamide CHART O
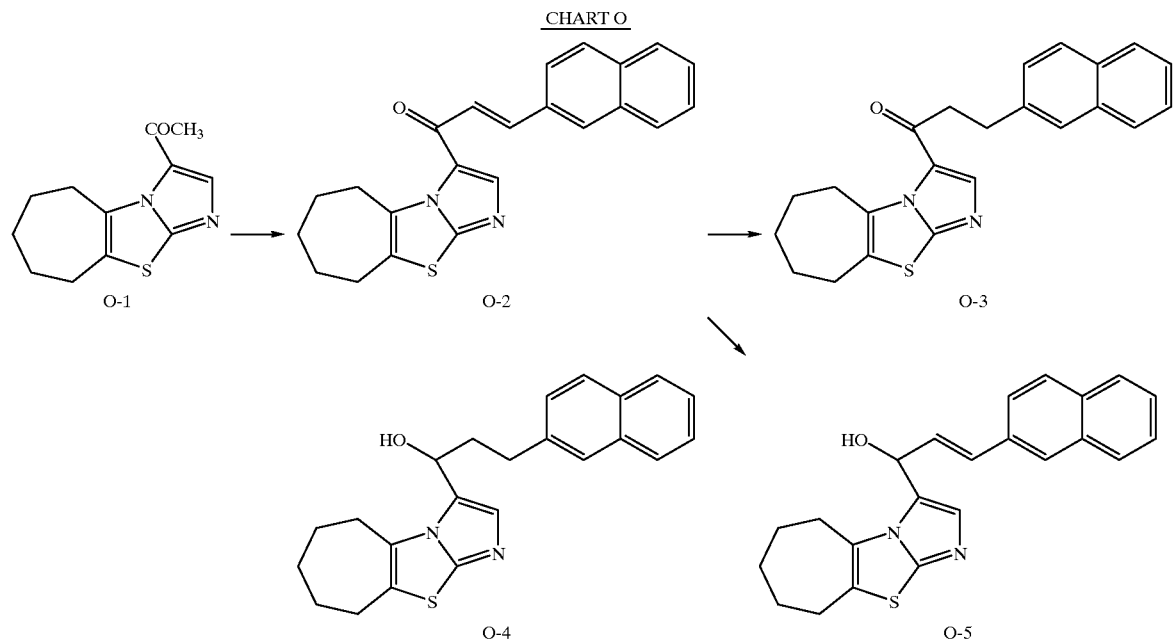
CHART P
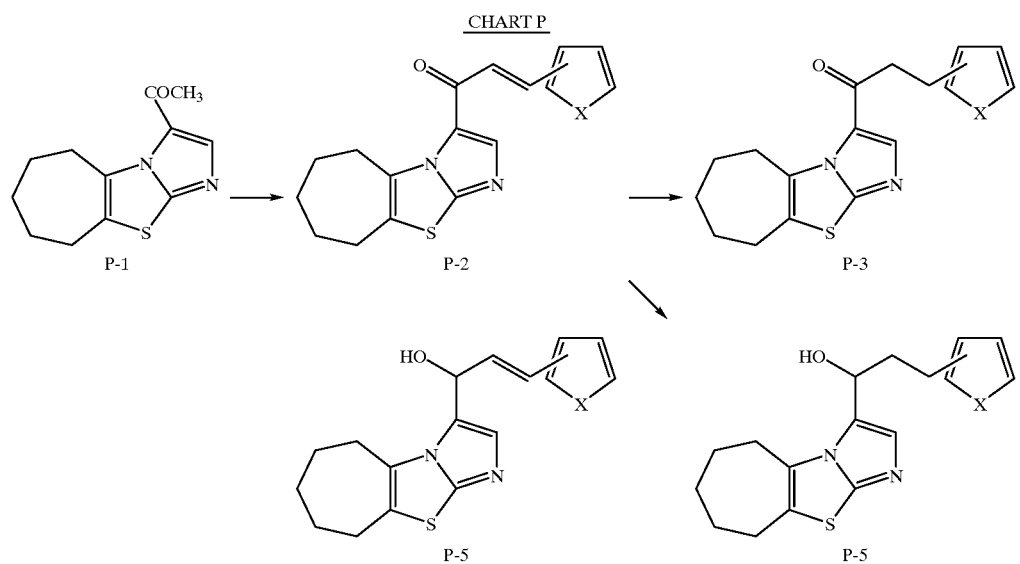
X = O, S, NH, NCH₃

CHART Q
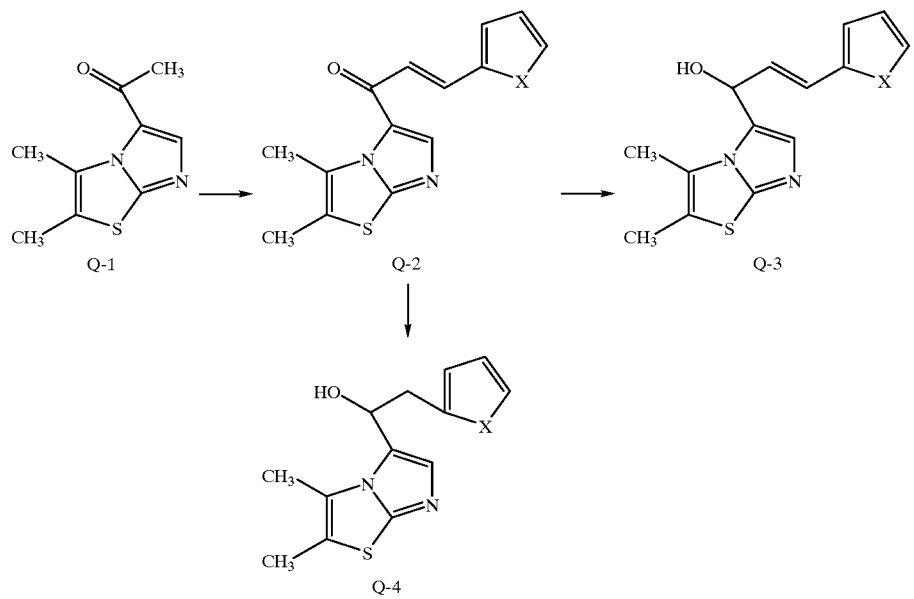
Chart Q Substituent Definitions
X = O
X = S
X = NH
X = NCH₃
CHART R
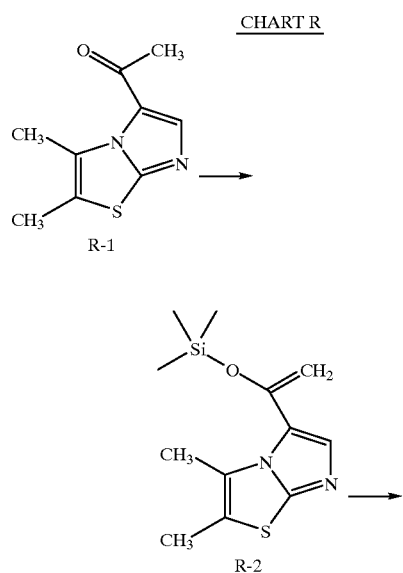
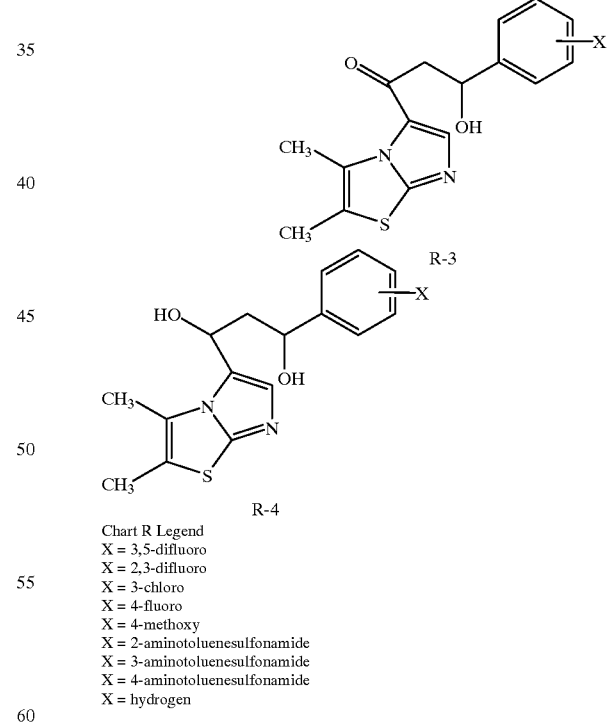
Chart R Legend
X = 3,5-difluoro
X = 2,3-difluoro
X = 3-chloro
X = 4-fluoro
X = 4-methoxy
X = 2-aminotoluenesulfonamide
X = 3-aminotoluenesulfonamide
X = 4-aminotoluenesulfonamide
X = hydrogen

TABLE 1

Protease Inhibition by 2,3-Dimethylimidazo[2,1-b]Thiazole 5-Methanol Derivatives

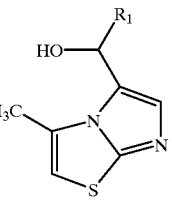

| Compound of | R | % Protease Inhibition 10 μM | 3.3–3.7 μM | 1.1–1.3 μM | Ki (nM) |
|---|---|---|---|---|---|
| Ex. 11 | $CH_2CH_2C_6H_5$ | 112 | 109 | 96 | 120 |
| Ex. 12 | $CH{=}CHC_6H_5$ | 110 | 103 | 63 | 567 ± 282 |
| Ex. 1 | $C{\equiv}C{-}C_6H_5$ | 16 | <10 | — | — |
| Ex. 2 | $CH_2C_6H_5$ | 86 | 27 | <10 | — |
| Ex. 3 | $CH_2CH_2CH_2C_6H_5$ | 115 | 72 | 16 | 246 ± 73 |

TABLE 2

Protease Inhibition by 3-Methylimidazothiazole-5-Methanol Derivatives

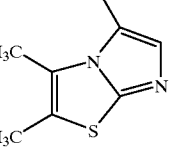

| Compound of | R | X | % Protease Inhibition 10 μM | 3.3–3.7 μM | 1.1–1.3 μM |
|---|---|---|---|---|---|
| Ex. 8 | $CH_2CH_2C_6H_5$ | H | 79 | 32 | <10 |
| Ex. 6 | $CH_2CH(CH_3)C_6H_5$ | H | 51 | <10 | <10 |
| Ex. 9 | $CH_2CH_2C_6H_4Br$ | H | 83 | 22 | <10 |
| Ex. 10 | $(CH_2)_4C_6H_5$ | H | 58 | 12 | <10 |

TABLE 3

Protease Inhibition by Imidazothiazole Tertiary Carbinols

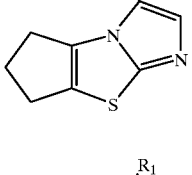

| Compound of | $R_1$ | $R_2$ | $R_3$ | % Protease Inhibition 10 μM | 3.3–3.7 μM | 1–1.2 μM |
|---|---|---|---|---|---|---|
| Ex. 7 | H | $CH_3$ | $CH_2CH_2C_6H_5$ | 14.5 | <10 | <10 |
| Ex. 5 | H | $CH_3$ | $CH{=}CHC_6H_5$ | <10 * | <10 | <10 |

*48.93% inhibition at 30 μM

TABLE 4

In Vitro Protease Activities of Imidazo[2,1-b]thiazoles

| | | Protease Inhibition | |
|---|---|---|---|
| | | % Inhibition (μM) | Ki (nM) |

A. $R_1 = CH_2CH_2C_6H_5$

| | | | | |
|---|---|---|---|---|
| Ex. 8 | 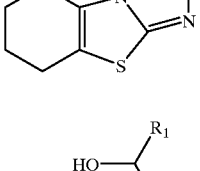 | 32 (3.3) | <10 (1.1) | — |
| Ex. 11 | (structure) | 94 (3.3) | 92 (1.2) | 120 |
| Ex. 13 | 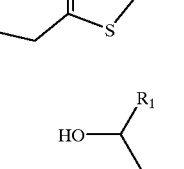 | 85 (3.3) | 39 (1.1) | — |
| Ex. 14 | (structure) | 102 (3.3) | 73 (1.1) | 68 ± 14 |
| Ex. 15 | (structure) | 94 (3.3) | 57 (1.1) | 57 ± 14 |
| Ex. 17 | 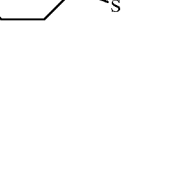 | 88 (3.3) | 62 (1.1) | 72 ± 26 |

TABLE 4-continued

In Vitro Protease Activities of Imidazo[2,1-b]thiazoles

| | | Protease Inhibition | |
|---|---|---|---|
| | | % Inhibition (μM) | Ki (nM) |
| Ex. 18 | 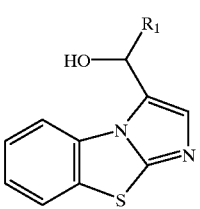 | 28 (3.3) | <10 (1.1) | — |

B. R$_2$ = CH$_2$CH$_2$CH$_2$CH$_2$C$_6$H$_5$

| | | | | |
|---|---|---|---|---|
| Ex. 10 | 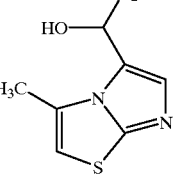 | 12 (3.3) | <10 (1.1) | — |
| Ex. 16 | 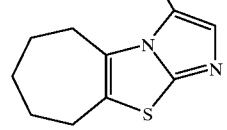 | 98 (3.3) | 54 (1.1) | 227 ± 42 |

TABLE 5

HIV-1 Protease Inhibition by Imidazo[2,1-b]benzothiazole-α-(2-phenylethyl)-methanol Derivatives

| Compound of | Structures R = CH$_2$CH$_2$C$_6$H$_5$ | % HIV Protease Inhibition | |
|---|---|---|---|
| | | 10 μM | 3.3 μM |
| Ex. 18 | 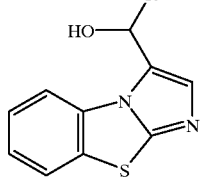 | 94 | 28 |
| Ex. 19 | 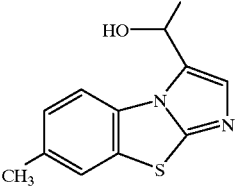 | 92 | 59 |

TABLE 5-continued

HIV-1 Protease Inhibition by Imidazo[2,1-b]benzothiazole-α-(2-phenylethyl)-methanol Derivatives

| Compound of | Structures R = CH$_2$CH$_2$C$_6$H$_5$ | % HIV Protease Inhibition | |
|---|---|---|---|
| | | 10 μM | 3.3 μM |
| Ex. 20 | 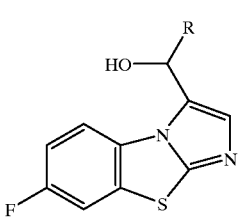 | 88 | 43 |
| Ex. 21 | 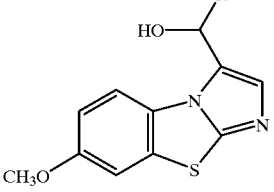 | 93 | 80 |

TABLE 6

HIV Protease Inhibition by Substituted Aryl- and Heteroaryl, Imidazo[2,1-b]thiazole-α-(2-phenylethyl) methanol Derivatives

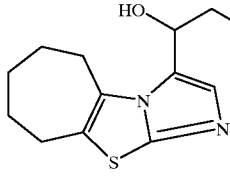

| COMPOUND OF EXAMPLE | R | PROTEASE INHIBITION | | | |
|---|---|---|---|---|---|
| | | 10 μM | 3.3 μM | 1.1 μM | Ki (nM) |
| 23 | 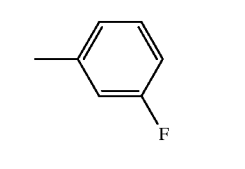 | 75 | 64 | 35 | 33 |
| 24 | 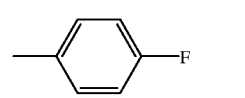 | 84 | 77 | 53 | 89 |

TABLE 6-continued

HIV Protease Inhibition by Substituted Aryl- and Heteroaryl, Imidazo[2,1-b]thiazole-α-(2-phenylethyl) methanol Derivatives

| COMPOUND OF EXAMPLE | R | PROTEASE INHIBITION | | | |
|---|---|---|---|---|---|
| | | 10 μM | 3.3 μM | 1.1 μM | Ki (nM) |
| 26 |  | 89 | 80 | 4.8 | — |
| 27 | 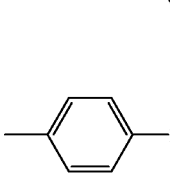 | 96 | 98 | 55 | — |
| 28 | 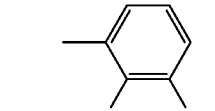 | 99 | 88 | 64 | — |
| 29 | 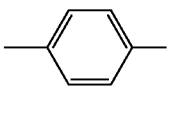 | 94 | 70 | 24 | — |
| 34 |  | 100 | 99 | 58 | — |
| 35 | 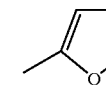 | 92 | 81 | 63 | — |
| 37 | 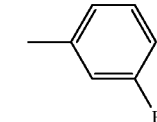 | 94 | 80 | 51 | — |

TABLE 6-continued

HIV Protease Inhibition by Substituted Aryl- and Heteroaryl, Imidazo[2,1-b]thiazole-α-(2-phenylethyl) methanol Derivatives

| COMPOUND OF EXAMPLE | R | PROTEASE INHIBITION | | | |
|---|---|---|---|---|---|
| | | 10 μM | 3.3 μM | 1.1 μM | Ki (nM) |
| 39 | 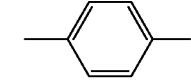 | 92 | 85 | 54 | — |

TABLE 7

HIV Protease Inhibition by Substituted Aryl- and Heteroaryl Imidazo[2,1-b]thiazole-α-(2-phenylethenyl)Methanol Derivatives

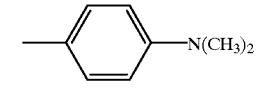

| COMPOUND OF EXAMPLE | R | PROTEASE INHIBITION | | |
|---|---|---|---|---|
| | | 10 μM | 3.3 μM | 1.1 μM |
| 22 | | 66 | 57 | 24 |
| 25 | | 21 | 33 | 23 |
| 30 | | 24 | <10 | — |

TABLE 7-continued

HIV Protease Inhibition by Substituted Aryl- and Heteroaryl Imidazo[2,1-b]thiazole-α-(2-phenylethenyl)Methanol Derivatives

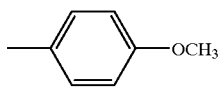

| COMPOUND OF EXAMPLE | R | PROTEASE INHIBITION | | |
|---|---|---|---|---|
| | | 10 μM | 3.3 μM | 1.1 μM |
| 36 | 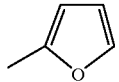 -OCH₃ | 42 | 52 | 15 |
| 38 | 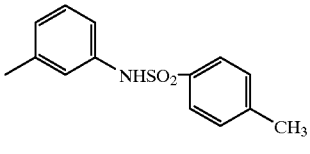 | 98 | 60 | 12 |

TABLE 8

HIV Protease Inhibition by Substituted Aryl- and Heteroaryl 2,3-dimethylimidazo[2,1-b]thiazole-α-(2-phenylethyl) methanol Derivatives

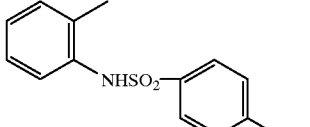

| COMPOUND OF EXAMPLE | R | PROTEASE INHIBITION | | |
|---|---|---|---|---|
| | | 10 μM | 3.3 μM | 1.1 μM |
| 31 | 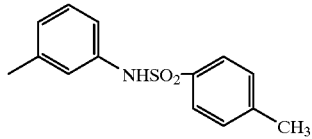 NHSO₂-⟨⟩-CH₃ | 98 | 68 | 15 |
| 33 | 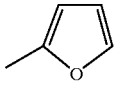 NHSO₂-⟨⟩-CH₃ | 97 | 52 | <10 |

TABLE 8-continued

HIV Protease Inhibition by Substituted Aryl- and Heteroaryl 2,3-dimethylimidazo[2,1-b]thiazole-α-(2-phenylethyl) methanol Derivatives

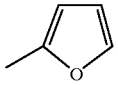

| COMPOUND OF EXAMPLE | R | PROTEASE INHIBITION | | |
|---|---|---|---|---|
| | | 10 μM | 3.3 μM | 1.1 μM |
| 42 | furyl | 92 | 46 | <10 |

TABLE 9

HIV Protease Inhibition by Substituted Aryl- and Heteroaryl 2,3-dimethylimidazo[2,1-b]thiazole-α-(2-phenylethenyl) methanol Derivatives

| COMPOUND OF EXAMPLE | R | PROTEASE INHIBITION | | |
|---|---|---|---|---|
| | | 10 μM | 3.3 μM | 1.1 μM |
| 32 | NHSO₂-⟨⟩-CH₃ | 15 | <10 | — |
| 41 | furyl | 81 | 19 | — |

I claim:
1. A compound of the formula I

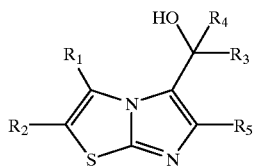

wherein $R_1$ is —H or —$CH_3$;
wherein $R_2$ is —H or —$CH_3$; or
wherein $R_1$ and $R_2$ taken together are

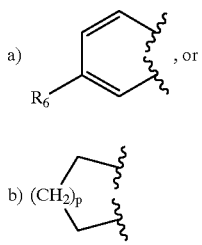

wherein p is 1 to 4 inclusive; or
wherein $R_6$ is
  a) —H,
  b) —$CH_3$,
  c) —F, or
  d) —$OCH_3$;
wherein $R_3$ is
  a) —$CH_2C_6H_5$,
  b) —$CH_2CH_2C_6H_5$,
  c) —$CH_2CH_2CH_2C_6H_5$,
  d) —$CH_2CH_2CH_2CH_2C_6H_5$,
  e) —$CH_2CH(CH_3)C_6H_5$,
  f) —$CH_2CH_2C_6H_4X$,
  wherein X may occupy either the ortho, meta or para-positions and is
    i) F
    ii) Cl,
    iii) Br,
    iv) $OCH_2R_1$,
    v) $N(CH_3)_2$,
    vi) $NHSO_2CH_2R_1$,
    vii) $SCH_3$
    viii) $NHCOCH_2R_1$, or
    ix) $NHSO_2C_6H_4X_1$,
    wherein $X_1$ is
      a. H,
      b. $CH_3$,
      c. F, or
      d. CN;
  g) —CH=CH—$C_6H_5$, (cis or trans);
  h) —C≡C—$C_6H_5$);
  i) CH=CH—$C_6H_3X_2$
    wherein $X_2$ is
      a. F,
      b. Cl,
      c. $OCH_3$, or
      d. $OCH_2O$;

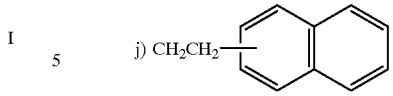

wherein $CH_2CH_2$ is appended to the 1- or 2-positions; or

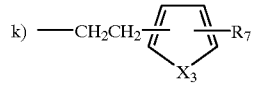

wherein
  i) —$CH_2CH_2$— appended to the 2- or 3-positions,
  ii) $X_3$ is
    a. O,
    b. S,
    c. NH,
    d. $NCH_3$, and
  iii) $R_7$ is
    a. $CH_3$, or
    b. $CH_3CH_2$;
wherein $R_4$ is —H or —$CH_3$; and
wherein $R_5$ is —H or —$CH_3$;
provided that when $R_1$ is —$CH_3$ and $R_2$ is —H or —$CH_3$, $R_4$ is not —H.

2. The compound of claim 1
wherein $R_1$ is —H or —$CH_3$;
wherein $R_2$ is —H or —$CH_3$;
wherein $R_3$ is
  a) —$CH_2C_6H_5$,
  b) —$CH_2CH_2C_6H_5$,
  c) —$CH_2CH_2CH_2C_6H_5$,
  d) —$CH_2CH_2CH_2CH_2C_6H_5$,
  e) —$CH_2CH(CH_3)C_6H_5$,
  f) —$CH_2CH_2C_6H_4X$,
  wherein X is
    i) F,
    ii) Cl, or
    iii) Br,
  g) —CH=CH—$C_6H_5$, (cis or trans) or
  h) —C≡C—$C_6H_5$;
wherein $R_4$ is —H or —$CH_3$; and
wherein $R_5$ is —H or —$CH_3$;
provided that when $R_1$ is —$CH_3$ and $R_2$ is —H or —$CH_3$, $R_4$ is not —H.

3. The compound of claim 1 of the formula I wherein $R_1$ and $R_2$ taken together are

wherein $R_6$ is
  a) —H
  b) —$CH_3$,
  c) —F, or
  d) —$OCH_3$.

4. The compound of claim 1 of the formula I wherein $R_1$ and $R_2$ taken together are

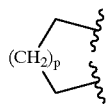

III wherein p is 1 to 4 inclusive.

5. The compound of claim 1 selected from the group consisting of:
2,3-Dimethyl-α-(2-phenylethynyl)imidazo-[2,1-b]thiazole-5-methanol,
2,3-Dimethyl-α-(2-phenylmethyl)imidazo-[2,1-b]thiazole-5-methanol,
2,3-Dimethyl-α-(3-phenylpropyl)imidazo-[2,1b]thiazole-5-methanol,
2,3-Dimethyl-α-Di(2-phenylethyl)imidazo-[2,1-b]thiazole-5-methanol,
α,3-Dimethyl-α-(E-2-phenyl-E-ethenyl)imidazo[2,1-b]thiazole-5-methanol,
3-Methyl-α-(2-phenylpropyl)imidazo[2,1-b]thiazole-5-methanol,
α,3-Dimethyl-α-(2-phenylethyl)imidazo[2,1-b]thiazole-5-methanol,
3-Methyl-α-(2-phenylethyl)imidazo[2,1-b]thiazole-5-methanol,
3-Methyl-α-(4-bromophenylethyl)imidazo[2,1-b]thiazole-5-methanol,
3-Methyl-α-(4-phenylbutyl)imidazo-[2,1-b]thiazole-5-methanol,
2,3-Dimethyl-α-(2-phenylethyl)imidazo[2,1-b]thiazole-5-methanol,
2,3-Dimethyl-α-(2-phenylethenyl)imidazo[2,1-b]thiazole-5-methanol,
6,7-Dihydro-α-(2-phenylethyl)-5H-cyclopent[d]imidazo[2,1-b]thiazole-3-methanol,
5,6,7,8-Tetrahydro-α-(2-phenylethyl)imidazo[2,1-b]benzothiazole-3-methanol,
6,7,8,9-Tetrahydro-α-(2-phenylethyl)-5H-cyclohept[d]imidazo[2,1-b]thiazole-3-methanol,
6,7,8,9-Tetrahydro-α-(4-phenylbutyl)-5H-cyclohept[d]imidazo[2,1-b]thiazole-3-methanol,
5,6,7,8,9,10-Hexahydro-α-(2-phenylethyl)cyclooct[d]imidazo-[2,1-b]thiazole-3-methanol,
α-(2-phenylethyl)-imidazo[2,1-b]benzothiazole-3-methanol,
7-Methyl-α-(2-phenylethyl)imidazo[2,1-b]benzothiazole-3-methanol,
7-Fluoro-α-(2-phenylethyl)imidazo[2,1-b]benzothiazole-3-methanol,
7-Methoxy-α-(2-phenylethyl)imidazo[2,1-b]benzothiazole-3-methanol,
α-[2-(3-Flurophenyl)ethenyl]-6,7,8,9-tetrahydro-5H-imidazo[2,1-b]thiazole-3-methanol
α-[2-(3-Fluorophenyl)ethyl]-6,7,8,9-tetrahydro-5H-cyclohept[d]imidazo[2, 1-b]thiazol-3-methanol,
α-[2-(4-Flurophenyl)ethyl]-6,7,8,9-tetrahydro-5H-cyclohept[d]imidazo[2, 1-b]thiazol-3-methanol,
[α-[2-(4-Flurophenyl)ethenyl]-6,7,8,9-tetrahydro-5H-cyclohept[d]imidazo[2,1-b]thiazol-3-methanol,]
α-[2-(3-Bromophenyl)ethyl]-6,7,8,9-tetrahydro-5H-cyclohept[d]imidazo-2,1-b]thiazol-3-methanol,
α-[2-(3-Chlorophenyl)ethyl]-6,7,8,9-tetrahydro-5H-cyclohept[d]imidazo[2,1-b]thiazol-3-methanol,
[α-[2-(3,5-Difluorophenyl)ethyl]-1-6,7,8,9-tetrahydro-5H-cyclohept[d]-imidazothiazol-3-methanol,]
α-[2-(4-dimethylaminophenyl)ethyl-6,7,8,9-tetrahydro-5H-cyclohept[d]imidazo-2,1-b]thiazol-3-methanol,
α-[2-(4-Dimethylaminophenyl)ethenyl]-6,7,8,9-tetrahydro-5H-cyclohept[d]-imidazo[2,1-b]thiazol-3-methanol,
N-[3-[3-(2,3-Dimethylimidazo[2, 1-b]thiazol-5-yl)-3-hydroxypropyl]phenyl-4-methylbenzenesulfonamide,
N-[2-[3-(2,3-Dimethylimidazo[2, 1-b]thiazol-5-yl)-3-hydroxy-propyl]phenyl-4-methylbenzensulfonamide,
[α-[2-(2,3-Difluorophenyl)ethyl]-6,7,8,9-tetrahydro-5H-cyclohept[d]imidazo-thiazol-3-methanol,]
α-[2-(4-methoxyphenyl)ethyl]6,7,8,9-tetrahydro-5H-cyclohept-[d]imidazo[2,1b]thiazol-3-methanol, and
[α-[2-(4-methoxyphenyl)ethenyl]-6,7,8,9-tetrahydro-5H-cyclohept-[d]imidazo[2, 1-]thiazol-3-methanol,]
α-[2-(2-Naphthalenyl)ethyl]-6,7,8,9-tetrahydro-5H-cyclohept[d]imidazo[2,1-b]thiazol-3-methanol],
α-[2-(2-Furanyl)ethenyl]-6,7,8,9-tetrahydro-5H-cyclohept[d]imidazo[2,1-b]thiazol-3-methanol,
α-[2-(2-Furanyl)ethyl]-6,7,8,9-tetrahydro-5H-cyclohept[d]imidazo[2,1-b]thiazol-3-methanol,
α-[2-(3-Furanyl)ethyl]-6,7,8,9-tetrahydro-5H-cyclohept[d]imidazo[2,1-b]thiazol-3-methanol,
α-[2-(2-Furanyl)ethenyl]2,3-dimethylimidazo[2,1-b]thiazol-3-methanol, and
α-[2-(2-Furanyl)ethyl]2,3-dimethylimidazo[2,1-b]thiazol-3-methanol].

6. The compound of claim 2 selected from the group consisting of:
2,3-Dimethyl-α-(2-phenylethynl)imidazo-[2,1-b]thiazole-5-methanol,
2,3-Dimethyl-α-(2-phenylmethyl)imidazo-[2,1-b]thiazole-5-methanol,
2,3-Dimethyl-α-(3-phenylpropyl)imidazo-[2,1-b]thiazole-5-methanol,
2,3-Dimethyl-α-Di(2-phenylethyl)imidazo-[2,1-b]thiazole-5-methanol,
α,3-Dimethyl-α-(E-2-phenyl-E-ethenyl)imidazo[2,1-b]thiazole-5-methanol,
3-Methyl-α-(2-phenylpropyl)imidazo[2,1-b]thiazole-5-methanol,
α,3-Dimethyl-α-(2-phenylethyl)imidazo[2,1-b]thiazole-5-methanol, and
3-Methyl-α-(2-phenylethyl)imidazo[2,1-b]thiazole-5-methanol,
3-Methyl-α-(4-bromophenylethyl)imidazo[2,1-b]thiazole-5-methanol,
3-Methyl-α-(4-phenylbutyl)imidazo-[2,1b]thiazole-5-methanol,
2,3-Dimethyl-α-(2-phenylethyl)imidazo[2,1-b]thiazole-5-methanol,
2,3-Dimethyl-α-(2-phenylethenyl)imidazo[2,1-b]thiazole-5-methanol,
N-[3-[3-(2,3-Dimethylimidazo[2, 1-b]thiazol-5-yl)-3-hydroxypropyl]phenyl-4-methylbenzenesulfonamide, and
N-[2-[3-(2,3-Dimethylimidazo[2, 1-b]thiazol-5-yl)-3-hydroxy-propyl]phenyl-4-methylbenzensulfonamide,
[α-[2-(2-Furanyl)ethenyl]2,3-dimethylimidazo[2,1-b]thiazol-3-methanol, and
α-[2-(2-Furanyl)ethyl]2,3-dimethylimidazo[2,1-b]thiazol-3-methanol].

7. The compound of claim 3 selected from the group consisting of:
α- (2phenylethyl)-imidazo[2,1-b]benzothiazole-3-methanol,
7-Methyl-α-(2-phenylethyl)imidazo[2,1-b]benzothiazole-3-methanol, 7-Fluoro-α-(2-phenylethyl)imidazo[2,1-b]benzothiazole-3-methanol, and 7Methoxy-α-(2-phenylethyl)imidazo[2,1-b]benzothiazole-3-methanol.

8. The compound of claim 4 selected from the group consisting of:

6,7-Dihydro-α-(2-phenylethyl)-5H-cyclopent[d]imidazo[2,1-b]thiazole-3-methanol, 5,6,7,8-Tetrahydro-α-(2-phenylethyl)imidazo[2,1-b]benzothiazole-3-methanol, 6,7,8,9-Tetrahydro-α-(2-phenylethyl)-5H-cyclohept[d]imidazo[2,1-b]thiazole-3-methanol, 6,7,8,9-Tetrahydro-α-(4-phenylbutyl)-5H-cyclohept[d]imidazo[2,1-b]thiazole-3-methanol, 5,6,7,8,9,10-Hexahydro-α-(2-phenylethyl)cyclooct[d]imidazo-[2,1-b]thiazole-3-methanol, α-[2-(3-Fluorophenyl)ethenyl]-6,7,8,9-tetrahydro-5H-imidazo]2,1-b]thiazole-3-methanol α-[2-(3-Fluorophenyl)ethyl]-6,7,8,9-tetrahydro-5H-cyclohept[d]imidazo[2, 1-b]thiazol-3-methanol, α-[2-(4-Fluorophenyl)ethyl]-6,7,8,9-tetrahydro-5H-cyclohept[d]imidazo[2, 1-b]thiazol-3-methanol,

[α-[2-(4-Fluorophenyl)ethenyl]-6,7,8,9-tetrahydro-5H-cyclohept[d]imidazo[2,1-b]thiazol-3-methanol,]

α-[2-(3-Bromophenyl)ethyl]-6,7,8,9-tetrahydro-5H-cyclohept[d]imidazo-2,1-b]thiazol-3-methanol, α-[2-(3-Chlorophenyl)ethyl]-6,7,8,9-tetrahydro-5H-cyclohept[d]imidazo[2,1-b]thiazol-3-methanol,

[α-[2-(3,5-Difluorophenyl)ethyl]-1-6,7,8,9-tetrahydro-5H-cyclohept[d]-imidazothiazol-3-methanol,]

α-[2-(4-dimethylaminophenyl)ethyl-6,7,8,9-tetrahydro-5H-cyclohept[d]imidazo-[2,1-b]thiazol-3-methanol, α-[2-(4-Dimethylaminophenyl)ethenyl]-6,7,8,9-tetrahydro-5H-cyclohept[d]-imidazo[2,1-b]thiazol-3-methanol, α-[2-(2,3-Difluorophenyl)ethyl]-6,7,8,9-tetrahydro-5H-cyclohept[d]imidazo-thiazol-3-methanol,]

α-[2-(4-methoxyphenyl)ethyl]-6,7,8,9-tetrahydro-5H-cyclohept-[d]imidazo[2,1b]thiazol-3-methanol, and

[α-[2-(4-methoxyphenyl)ethenyl]-6,7,8,9-tetrahydro-5H-cyclohept-[d]imidazo[2, 1-b]thiazol-3-methanol,]

α-[2-(2-Naphthalenyl)ethyl]-6,7,8,9-tetrahydro-5H-cyclohept[d]imidazo[2,1-b]thiazol-3-methanol[, α-[2-(2-Furanyl)ethenyl]-6,7,8,9-tetrahydro-5H-cyclohept[d]imidazo[2,1-b]thiazol-3-methanol, α-[2-(2-Furanyl)ethyl]-6,7,8,9-tetrahydro-5H-cyclohept[d]imidazo[2,1-b]thiazol-3-methanol, α-[2-(3-Furanyl)ethyl]-6,7,8,9-tetrahydro-5H-cyclohept[d]imidazo[2,1-b]thiazol-3-methanol.

9. A method for treatment of mammals infected with a retrovirus, said method comprising administering to a mammal infected with said retrovirus a therapeutically effective amount of a compound of the formula I

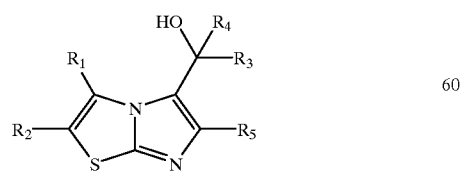

I wherein $R_1$ is —H or —CH$_3$;
wherein $R_2$ is —H or —CH$_3$; or wherein $R_1$ and $R_2$ taken together are a)

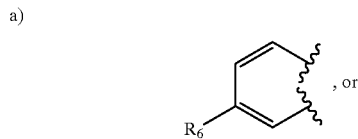

, or

II b)

III wherein p is 1 to 4 inclusive; or wherein $R_6$ is
  a) —H
  b) —CH$_3$,
  c) —F, or
  d) —OCH$_3$;

wherein $R_3$ is
  a) —CH$_2$C$_6$H$_5$,
  b) —CH$_2$CH$_2$C$_6$H$_5$,
  c) —CH$_2$CH$_2$CH$_2$C$_6$H$_5$,
  d) —CH$_2$CH$_2$CH$_2$CH$_2$C$_6$H$_5$,
  e) —CH$_2$CH(CH$_3$)C$_6$H$_5$,
  f) —CH$_2$CH$_2$C$_6$H$_4$X, wherein X may occupy either the ortho, meta or para-positions and is
  i) F,
  ii) Cl,
  iii) Br,
  iv) OCH$_2$R$_1$,
  v) N(CH$_3$)$_2$,
  vi) NHSO$_2$CH$_2$R$_1$,
  vii) SCH$_3$
  viii) NHCOCH$_2$R$_1$, or
  ix) NHSO$_2$C$_6$H$_4$X$_1$,
    wherein X$_1$ is
      a. H,
      b. CH$_3$,
      c. F, or
      d. CN;

g) —CH=CH—C$_6$H$_5$, (cis or trans);
  h) —CH≡C—C$_6$H$_5$);
  i) —CH=CH—C$_6$H$_3$X$_2$
    wherein X$_2$ is
      a. F,
      b. Cl,
      c. OCH$_3$, or
      d. —O—CH$_2$O;

j) CH$_2$CH$_2$— 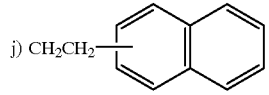

wherein CH$_2$CH$_2$ is appended to the 1- or 2-positions;
or k) 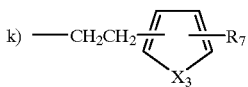

wherein
- i) —CH$_2$CH$_2$— appended to the 2- or 3- positions,
- ii) X$_3$ is
  - a. O,
  - b. S,
  - c. NH, and
  - d. —NCH$_3$;
- iii) R$_7$ is
  - a. CH$_3$, or
  - b. CH$_3$CH$_2$;

wherein R$_4$ is —H or —CH$_3$; and
wherein R$_5$ is —H or —CH$_3$;
provided that when R$_1$ is —CH$_3$ and R$_2$ is —H or —CH$_3$, R$_4$ is not —H.

10. The method of claim 9 wherein the compound is selected from the group consisting of:
2,3-Dimethyl-α-(2-phenylethynyl)imidazo-[2,1-b]thiazole-5-methanol,
2,3-Dimethyl-α-(2-phenylmethyl)imidazo-[2,1-b]thiazole-5-methanol,
2,3-Dimethyl-α-(3-phenylpropyl)imidazo-[2,1-b]thiazole-5-methanol,
2,3-Dimethyl-α-(2-phenylethyl)imidazo-[2,1-b]thiazole-5-methanol,
α,3-Dimethyl-α-(E-2-phenyl-E-ethenyl)imidazo[2,1-b]thiazole-5-methanol,
3-Methyl-α-(2-phenylpropyl)imidazo[2,1-b]thiazole-5-methanol,
α,3-Dimethyl-α-(2-phenylethyl)imidazo[2,1-b]thiazole-5-methanol,
3-Methyl-α-(2-phenylethyl)imidazo[2,1-b]thiazole-5-methanol,
3-Methyl-α-(4-bromophenylethyl)imidazo[2,1-b]thiazole-5-methanol,
3-Methyl-α-(4-phenylbutyl)imidazo-[2,1-b]thiazole-5-methanol,
2,3-Dimethyl-α-(2-phenylethyl)imidazo[2,1-b]thiazole-5-methanol,
2,3-Dimethyl-α-(2-phenylethenyl)imidazo[2,1-b]thiazole-5-methanol,
6,7-Dihydro-α-(2-phenylethyl)-5H-cyclopent[d]imidazo[2,1-b]thiazole-3-methanol,
5,6,7,8-Tetrahydro-α-(2-phenylethyl)imidazo[2,1-b]benzothiazole-3-methanol,
6,7,8,9-Tetrahydro-α-(2-phenylethyl)-5H-cyclohept[d]imidazo[2,1-b]thiazole-3-methanol,
6,7,8,9-Tetrahydro-α-(4-phenylbutyl)-5H-cyclohept[d]imidazo[2,1-b]thiazole-3-methanol,
5,6,7,8,9,10-Hexahydro-α-(2-phenylethyl)cyclooct[d]imidazo-[2,1-b]thiazole-3-methanol,
α-(2-phenylethyl)-imidazo[2,1-b]benzothiazole-3-methanol,
7-Methyl-α-(2-phenylethyl)imidazo[2,1-b]benzothiazole-3-methanol,
7-Fluoro-α-(2-phenylethyl)imidazo[2,1-b]benzothiazole-3-methanol,
7-Methoxy-α-(2-phenylethyl)imidazo[2,1-b]benzothiazole-3-methanol,
α[2-(3-Fluorophenyl)ethenyl]-6,7,8,9-tetrahydro-5H-imidazo[2,1-b]thiazole-3-methanol
α[2-(3-Fluorophenyl)ethyl]-6,7,8,9-tetrahydro-5H-cyclohept[d]imidazo[2, 1-b]thiazol-3-methanol,
α-[2-(4-Fluorophenyl)ethyl]-6,7,8,9-tetrahydro-5H-cyclohept[d]imidazo[2, 1-b]thiazol-3-methanol,
[α-[2-(4-Fluorophenyl)ethenyl]-6,7,8,9-tetrahydro-5H-cyclohept[d]imidazo[2,1-b]thiazol-3-methanol,]
α-[2-(3-Bromophenyl)ethyl]-6,7,8,9-tetrahydro-5H-cyclohept[d]imidazo-2,1-b]thiazol-3-methanol,
α-[2-(3-Chlorophenyl)ethyl]-6,7,8,9-tetrahydro-5H-cyclohept[d]imidazo[2,1-b]thiazol-3-methanol,
[α[2-(3,5-Difluorophenyl)ethyl]-6,7,8,9-tetrahydro-5H-cyclohept[d]-imidazothiazol-3-methanol,]
α-[2-(4-dimethylaminophenyl)ethyl-6,7,8,9-tetrahydro-5H-cyclohept[d]imidazo-[2,1-b]thiazol-3-methanol,
α-[2-(4-Dimethylaminophenyl)ethenyl]-6,7,8,9-tetrahydro-5H-cyclohept[d]-imidazo[2,1-b]thiazol-3-methanol,
N-[3-[3-(2,3-Dimethylimidazo[2, 1-b]thiazol-5-yl)-3-hydroxypropyl]phenyl-4-methylbenzenesulfonamide,
N-[2-[3-(2,3-Dimethylimidazo[2, 1-b]thiazol-5-yl)-3-hydroxy-propyl]phenyl-4-methylbenzensulfonamide,
[α-[2-(2,3-Difluorophenyl)ethyl]-6,7,8,9-tetrahydro-5H-cyclohept[d]imidazo-thiazol-3-methanol,]
α-[2-(4-methoxyphenyl)ethyl]-6,7,8,9-tetrahydro-5H-cyclohept-[d]imidazo[2,1-b]thiazol-3-methanol, and
[α-[2-(4-methoxyphenyl)ethenyl]-6,7,8,9-tetrahydro-5H-cyclohept-[d]imidazo[2, 1-b]thiazol-3-methanol,]
α-[2-(2-Naphthalenyl)ethyl]-6,7,8,9-tetrahydro-5H-cyclohept[d]imidazo[2,1-b]thiazol-3-methanol],
α-[2-(2-Furanyl)ethenyl]-6,7,8,9-tetrahydro-5H-cyclohept[d]imidazo[2,1-b]thiazol-3-methanol,
α-[2-(2-Furanyl)ethyl]-6,7,8,9-tetrahydro-5H-cyclohept[d]imidazo[2,1-b]thiazol-3-methanol,
α-[2-(3-Furanyl)ethyl]-6,7,8,9-tetrahydro-5H-cyclohept[d]imidazo[2,1-b]thiazol-3-methanol,
α-[2-(2-Furanyl)ethenyl]2,3-dimethylimidazo[2,1-b]thiazol-3-methanol, and
α-[2-(2-Furanyl)ethyl]2,3-dimethylimidazo[2,1-b]thiazol-3-methanol].

11. A pharmaceutical composition for use in treatment of a mammal infected with a retrovirus, said composition comprising a pharmaceutically acceptable solvent, diluent, adjuvant or carrier and, as the active ingredient, from about 0.1 mg to 100 mg per kg of body weight per day of a compound of the formula I

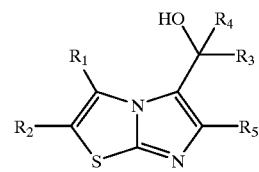

I wherein R$_1$ is —H or —CH$_3$;
wherein R$_2$ is —H or —CH$_3$; or
wherein R$_1$ and R$_2$ taken together are a)

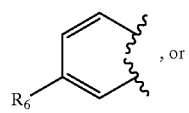

II

, or b)

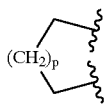
III wherein p is 1 to 4 inclusive; or
wherein $R_6$ is
 a) —H
 b) —$CH_3$,
 c) —F, or
 d) —$OCH_3$;
wherein $R_3$ is
 a) —$CH_2C_6H_5$,
 b) —$CH_2CH_2C_6H_5$,
 c) —$CH_2CH_2CH_2C_6H_5$,
 d) —$CH_2CH_2CH_2CH_2C_6H_5$,
 e) —$CH_2CH(CH_3)C_6H_5$,
 f) —$CH_2CH_2C_6H_4X$,
 wherein X may occupy either the ortho, meta or para positions and is
  i) F,
  ii) Cl,
  iii) Br,
  iv) $OCH_2R_1$,
  v) $N(CH_3)_2$,
  vi) $NHSO_2CH_2R_1$,
  vii) $SCH_3$
  viii) $NHCOCH_2R_1$, or
  ix) $NHSO_2C_6H_4X_1$,
  wherein $X_1$ is
   a. H,
   b. $CH_3$,
   c. F, or
   d. CN;
 g) —CH═CH—$C_6H_5$, (cis or trans);
 h) —CH≡C—$C_6H_5$);
 i) CH═CH—$C_6H_3X_2$
  wherein $X_2$ is
   a. F,
   b. Cl,
   c. $OCH_3$, or
   d. —O—$CH_2$O;

j) $CH_2CH_2$—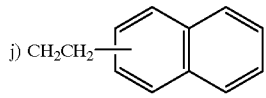

wherein $CH_2CH_2$ is appended to the 1- or 2-positions; or k) —$CH_2CH_2$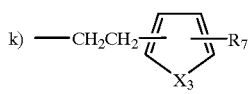—$R_7$ wherein
 i) —$CH_2CH_2$— appended to the 2- or 3-positions,
 ii) $X_3$ is
  a. O,
  b. S,
  c. NH,
  d. —$NCH_3$, and iii) $R_7$ is
 a. $CH_3$, or
 b. $CH_3CH_2$;
wherein $R_4$ is —H or —$CH_3$; and
wherein $R_5$ is —H or —$CH_3$;
 provided that when $R_1$ is —$CH_3$ and $R_2$ is —H or —$CH_3$, $R_4$ is not —H.

12. The composition of claim 11 wherein the compound is selected from the group consisting of:
2,3-Dimethyl-α-(2-phenylethynyl)imidazo-[2,1-b]thiazole-5-methanol,
2,3-Dimethyl-α-(2-phenylmethyl)imidazo-[2,1-b]thiazole-5-methanol,
2,3-Dimethyl-α-(3-phenylpropyl)imidazo-[2,1-b]thiazole-5-methanol,
2,3-Dimethyl-α-Di(2-phenylethyl)imidazo-[2,1-b]thiazole-5-methanol,
α,3-Dimethyl-α-(E-2-phenyl-E-ethenyl)imidazo[2,1-b]thiazole-5-methanol,
3-Methyl-α-(2-phenylpropyl)imidazo[2,1-b]thiazole-5-methanol,
α,3-Dimethyl-α-(2-phenylethyl)imidazo[2,1-b]thiazole-5-methanol,
3-Methyl-α-(2-phenylethyl)imidazo[2,1-b]thiazole-5-methanol,
3-Methyl-α-(4-bromophenylethyl)imidazo[2,1-b]thiazole-5-methanol,
3-Methyl-α-(4-phenylbutyl)imidazo-[2,1-b]thiazole-5-methanol,
2,3-Dimethyl-α-(2-phenylethyl)imidazo[2,1-b]thiazole-5-methanol,
2,3-Dimethyl-α-(2-phenylethenyl)imidazo[2,1-b]thiazole-5-methanol,
6,7-Dihydro-α-(2-phenylethyl)-5H-cyclopent[d]imidazo[2,1-b]thiazole-3-methanol,
5,6,7,8-Tetrahydro-α-(2-phenylethyl)imidazo[2,1-b]benzothiazole-3-methanol,
6,7,8,9-Tetrahydro-α-(2-phenylethyl)-5H-cyclohept[d]imidazo[2,1-b]thiazole-3-methanol,
6,7,8,9-Tetrahydro-α-(4-phenylbutyl)-5H-cyclohept[d]imidazo[2,1-b]thiazole-3-methanol,
5,6,7,8,9,10-Hexahydro-α-(2-phenylethyl)cyclooct[d]imidazo-[2,1-b]thiazole-3-methanol,
α-(2-phenylethyl)-imidazo[2,1-b]benzothiazole-3-methanol,
7-Methyl-α-(2-phenylethyl)imidazo[2,1-b]benzothiazole-3-methanol,
7-Fluoro-α-(2-phenylethyl)imidazo[2,1-b]benzothiazole-3-methanol,
7-Methoxy-α-(2-phenylethyl)imidazo[2,1-b]benzothiazole-3-methanol,
α-[2-(3-Fluorophenyl)ethenyl]-6,7,8,9-tetrahydro-5H-imidazo[2,1-b]thiazole-3-methanol
α-[2-(3-Fluorophenyl)ethyl]-6,7,8,9-tetrahydro-5H-cyclohept[d]imidazo[2, 1-b]thiazol-3-methanol,
α-[2-(4-Fluorophenyl)ethyl]-6,7,8,9-tetrahydro-5H-cyclohept[d]imidazo[2, 1-b]thiazol-3-methanol,
[α-[2-(4-Fluorophenyl)ethenyl]-6,7,8,9-tetrahydro-5H-cyclohept[d]imidazo[2,1-b]thiazol-3-methanol,
α-[2-(3-Bromophenyl)ethyl]-6,7,8,9-tetrahydro-5H-cyclohept[d]imidazo-2,1-b]thiazol-3-methanol,
α-[2-(3-Chlorophenyl)ethyl]-6,7,8,9-tetrahydro-5H-cyclohept[d]imidazo[2,1-b]thiazol-3-methanol,
α-[2-(3,5-Difluorophenyl)ethyl]-1 6,7,8,9-tetrahydro-5H-cyclohept[d]-imidazothiazol-3-methanol,]
α-[2-(4-dimethylaminophenyl)ethyl-6,7,8,9-tetrahydro-5H-cyclohept[d]imidazo-[2,1-b]thiazol-3methanol, α-[2-(4-Dimethylaminophenyl)ethenyl]-6,7,8,9-tetrahydro-5H-cyclohept[d]-imidazo[2,1-b]thiazol-3-methanol,
N-[3-[3-(2,3-Dimethylimidazo[2, 1-b]thiazol-5-yl)-3-hydroxypropyl]phenyl-4-methylbenzenesulfonamide,
N-[2-[3-(2,3-Dimethylimidazo[2, 1-b]thiazol-5-yl)-3-hydroxy-propyl]phenyl-4-methylbenzensulfonamide,
[α-[2-(2,3-Difluorophenyl)ethyl]-6,7,8,9-tetrahydro-5H-cyclohept[d]imidazo-thiazol-3-methanol,]
α-[2-(4-methoxyphenyl)ethyl]-6,7,8,9-tetrahydro-5H-cyclohept-[d]imidazo[2,1-b]thiazol-3-methanol, and
[α[2-(4-methoxyphenyl)ethenyl]-6,7,8,9-tetrahydro-5H-cyclohept-[d]imidazo[2, 1-b]thiazol-3-methanol,]
α-[2-(2-Naphthalenyl)ethyl]-6,7,8,9-tetrahydro-5H-cyclohept[d]imidazo[2,1-b]thiazol-3-methanol],
α-[2-(2-Furanyl)ethenyl]-6,7,8,9-tetrahydro-5H-cyclohept[d]imidazo[2,1-b]thiazol-3-methanol,
α-[2-(2-Furanyl)ethyl]-6,7,8,9-tetrahydro-5H-cyclohept[d]imidazo[2,1-b]thiazol-3-methanol,
α-[2-(3-Furanyl)ethyl]-6,7,8,9-tetrahydro-5H-cyclohept[d]imidazo[2,1-b]thiazol-3-methanol,
α-[2-(2-Furanyl)ethenyl]2,3-dimethylimidazo[2,1-b]thiazol-3-methanol, and
α-[2-(2-Furanyl)ethyl]2,3-dimethylimidazo[2,1-b]thiazol-3-methanol].

13. A compound selected from the group consisting of:
α-[2-(4-Fluorophenyl)ethenyl]-6,7,8,9-tetrahydro-5H-cyclohept[d]imidazo[2,1-b]thiazol-3-methanol,
α-[2-(3,5-Difluorophenyl)ethyl]-1-6,7,8,9-tetrahydro-5H-cyclohept[d]-imidazothiazol-3-methanol,
α-[2-(2,3-Difluorophenyl)ethyl]-6,7,8,9-tetrahydro-5H-cyclohept[d]imidazothiazol-3-methanol,
α-[2-(4-methoxyphenyl)ethenyl]-6,7,8,9-tetrahydro-5H-cyclohept-[d]imidazo[2, 1-b]thiazol-3-methanol,
α-[2-(2-Furanyl)ethenyl]-6,7,8,9-tetrahydro-5H-cyclohept[d]imidazo[2,1-b]thiazol-3-methanol,
α-[2-(2-Furanyl)ethyl]-6,7,8,9-tetrahydro-5H-cyclohept[d]imidazo[2,1-b]thiazol-3-methanol,
α-[2-(3-Furanyl)ethyl]-6,7,8,9-tetrahydro-5H-cyclohept[d]imidazo[2,1-b]thiazol-3-methanol,
α-[2-(2-Furanyl)ethenyl]2,3-dimethylimidazo[2,1-b]thiazol-3-methanol, and
α-[2-(2-Furanyl)ethyl]2,3-dimethylimidazo[2,1-b]thiazol-3-methanol.

14. A method for treatment of mammals infected with a retrovirus, said method comprising administering to a mammal infected with said retrovirus a therapeutically effective amount of a compound selected from the group consisting of:
α-[2-(4-Fluorophenyl)ethenyl]-6,7,8,9-tetrahydro-5H-cyclohept[d]imidazo[2,1-b]thiazol-3-methanol,
α-[2-(3,5-Difluorophenyl)ethyl]-1-6,7,8,9-tetrahydro-5H-cyclohept[d]-imidazothiazol-3-methanol,
α-[2-(2,3-Difluorophenyl)ethyl]-6,7,8,9-tetrahydro-5H-cyclohept[d]imidazothiazol-3-methanol,
α-[2-(4-methoxyphenyl)ethenyl]-6,7,8,9-tetrahydro-5H-cyclohept-[d]imidazo[2, 1-b]thiazol-3-methanol,
α-[2-(2-Furanyl)ethenyl]-6,7,8,9-tetrahydro-5H-cyclohept[d]imidazo[2,1-b]thiazol-3-methanol,
α-[2-(2-Furanyl)ethyl]-6,7,8,9-tetrahydro-5H-cyclohept[d]imidazo[2,1-b]thiazol-3-methanol,
α-[2-(3-Furanyl)ethyl]-6,7,8,9-tetrahydro-5H-cyclohept[d]imidazo[2,1-b]thiazol-3-methanol,
α-[2-(2-Furanyl)ethenyl]2,3-dimethylimidazo[2,1-b]thiazol-3-methanol, and
α-[2-(2-Furanyl)ethyl]2,3-dimethylimidazo[2,1-b]thiazol-3-methanol.

15. A pharmaceutical composition for use in treatment of a mammal infected with a retrovirus, said composition comprising a pharmaceutically acceptable solvent, diluent, adjuvant or carrier and, as the active ingredient, from about 0.1 mg to 100 mg per kg of body weight per day of a compound selected from the group consisting of:
α[2-(4-Fluorophenyl)ethenyl]-6,7,8,9-tetrahydro-5H-cyclohept[d]imidazo[2,1-b]thiazol-3-methanol,
α[2-(3,5-Difluorophenyl)ethyl]-6,7,8,9-tetrahydro-5H-cyclohept[d]-imidazothiazol-3-methanol,
α[2-(2,3-Difluorophenyl)ethyl]-6,7,8,9-tetrahydro-5H-cyclohept[d]-imidazothiazol-3-methanol,
α[2-(4-methoxyphenyl)ethenyl]-6,7,8,9-tetrahydro-5H-cyclohept-[d]imidazo[2, 1-b]thiazol-3-methanol,
α[2-(2-Furanyl)ethenyl]-6,7,8,9-tetrahydro-5H-cyclohept[d]imidazo[2,1-b]thiazol-3-methanol,
α[2-(2-Furanyl)ethyl]-6,7,8,9-tetrahydro-5H-cyclohept[d]imidazo[2,1-b]thiazol-3-methanol,
α[2-(3-Furanyl)ethyl]-6,7,8,9-tetrahydro-5H-cyclohept[d]imidazo[2,1-b]thiazol-3-methanol,
α[2-(2-Furanyl)ethenyl]2,3-dimethylimidazo[2,1-b]thiazol-3-methanol, and
α[2-(2-Furanyl)ethyl]2,3-dimethylimidazo[2,1-b]thiazol-3-methanol.

* * * * *